(12) United States Patent
Sun

(10) Patent No.: US 9,150,585 B2
(45) Date of Patent: Oct. 6, 2015

(54) ANALOGS OF CAMPTOTHECIN

(71) Applicant: FL Therapeutics, LLC, Princeton, NJ (US)

(72) Inventor: Qun Sun, Princeton, NJ (US)

(73) Assignee: FL Therapeutics LLC, Princeton, NJ (US)

( * ) Notice: Subject to any disclaimer, the term of this patent is extended or adjusted under 35 U.S.C. 154(b) by 0 days.

(21) Appl. No.: 14/076,310

(22) Filed: Nov. 11, 2013

(65) Prior Publication Data
US 2014/0135356 A1 May 15, 2014

Related U.S. Application Data

(60) Provisional application No. 61/725,778, filed on Nov. 13, 2012, provisional application No. 61/762,388, filed on Feb. 8, 2013.

(51) Int. Cl.
*A61K 31/4745* (2006.01)
*C07D 491/22* (2006.01)

(52) U.S. Cl.
CPC .................................. *C07D 491/22* (2013.01)

(58) Field of Classification Search
USPC ............................................ 514/283; 546/48
See application file for complete search history.

(56) References Cited

FOREIGN PATENT DOCUMENTS

EP      2007386 B1      8/2012

OTHER PUBLICATIONS

Kularatne, S. A. et al.: Synthesis and biological analysis of prostate-specific membrane antigen-targeted anticancer prodrugs. J. Medicin. Chem. ), vol. 53, pp. 7767-7777, 2010.*
Prijovich et al., "Stability of the new prodrug 9-aminocamptothecin glucuronide (9ACG) in the presence of human serum albumin," Biochem Pharmacol., 66(7):1181-1187, Oct. 1, 2003.

* cited by examiner

*Primary Examiner* — Charanjit Aulakh
(74) *Attorney, Agent, or Firm* — Fish & Richardson P.C.

(57) ABSTRACT

The present invention provides novel conjugates of camptothecin and camptothecin analogs with a linker and an HSA-binding moiety. The novel conjugates are prodrug forms of the camptothecin or camptothecin analogs and can be used to treat mammalian cell proliferative diseases, such as cancer.

28 Claims, No Drawings

ANALOGS OF CAMPTOTHECIN

FIELD OF THE INVENTION

The present invention relates to novel conjugate prodrugs of the camptothecin class of compounds, their methods of preparation and use as antitumor agents.

BACKGROUND OF THE INVENTION

Camptothecin is a well-known alkaloid that was first isolated in 1966 from *Camptotheca acuminate*. Camptothecin shows strong cytotoxic activity and anti-tumor activity. Due to its poor water solubility (2.5 ug/mL), the first clinical trials in the early seventies were performed using CPT as the sodium salt of the hydroxycarboxylate form, with an open E-ring. However, severe and unpredictable side effects hindered further clinical development.

A renewed interest in CPT and CPT derivatives came with the elucidation of their mechanism of action, i.e. the inhibition of the nuclear enzyme topoisomerase I. It was also discovered that the lactone ring of CPT is necessary for specific interaction with topoisomerase I and selective antitumor activity. Several derivatives of CPT with improved solubility and lactone ring stability have been synthesized, including irinotecan and topotecan (which have been FDA approved for clinical use in the therapy of colorectal, ovarian and lung cancer), as well as SN-38, 9-Aminocamptothecin, 9-Nitro-camptothecin, GI-147211, Exatecan and Karenitecin. See Table 1. The clinical application of these drugs is, however, limited by their toxic, dose-related side effects, such as myelosuppression, gastrointestinal disorders and stomatitis.

Experience with these CPT derivatives suggests that the behavior of CPT derivatives in the presence of human serum albumin (HSA) is one of the determining factors of their clinical efficacy. The equilibrium concentration of active 9-Aminocamptothecin in blood is less than 0.5% due to preferential binding of the inactive 9-AC open-ring carboxy to HSA which shifts the blood equilibrium between the active, closed-ring 9-AC lactone and the inactive open-ring carboxy form toward the inactive, open-ring 9-AC carboxy form. CPT displays similar behavior. In contrast, the clinically important CPT derivative irinotecan and topotecan display enhanced lactone stability in the presence of HSA.

TABLE 1

Well-known CPT derivatives.

| Compound | $R_2$ | $R_3$ | $R_4$ | $R_5$ | $R_6$ |
|---|---|---|---|---|---|
| Camptothecin | —H | —H | —H | —H | —H |
| Topotecan | —H | —CH$_2$N(CH$_3$)$_2$ | —OH | —H | —H |
| Irinotecan | —CH$_2$CH$_3$ | —H | —O—C(O)—N(piperidine)—N(piperidine) | | —H |
| -HSN-38 | —CH$_2$CH$_3$ | —H | —OH | —H | —H |
| 9-Aminocamptothecin | —H | —NH$_2$ | —H | —H | —H |
| 9-Nitrocamptothecin | —H | —NO$_2$ | —H | —H | —H |
| GI-147211 | | —CH$_2$—N(piperazine)N—CH$_3$ | —H | | —OCH$_2$CH$_2$O— |
| -HExatecan | | —CH(NH$_2$)—CH$_2$—CH$_2$ | —CH$_3$ | —F | —H |
| Karenitecin | —H | —CH$_2$CH$_2$Si(CH$_3$)$_3$ | —H | —H | —H |

Furthermore, attempts have been made to selectively bind a biologically active, lactone form of a CPT derivative to HSA, in order to prevent HSA from preferentially binding and stabilizing the inactive carboxy form of the CPT derivative, thereby driving the lactone ring/open-ring carboxy blood equilibrium toward the active lactone ring form. However, these attempts have been only partially successful. For instance, in Z. M. Prijovich et al., *Biochem. Pharm.* 66 (2003): 1181-1187, 9-Aminocamptothecin glucuronide (9AGC) shows improved stability of the active lactone ring form in blood, reaching equilibrium in blood of about 20% lactone ring form and a blood half-life increased to about 50 minutes.

Accordingly, there is a clear and continuing need to create more soluble forms of CPT and analogs which remain substantially in their clinically effective lactone ring form in blood, and particularly in the presence of HSA.

SUMMARY OF THE INVENTION

It is thus an object of the present invention to provide conjugate prodrugs of CPT and CPT analogs that remain substantially in their clinically effective lactone ring form in blood, and particularly in the presence of HSA. It is a further object of the present invention to provide methods of treating mammalian cell proliferative disorders using these conjugate prodrugs of CPT or CPT analogs. The present invention provides compounds comprising CPT or a known CPT analogs conjugated to a linker and HSA-binding moiety according to Formula I:

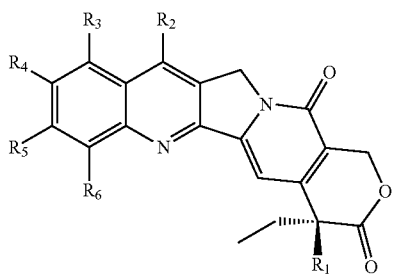

wherein
$R_1$ is OH or linker-HSA binding moiety;
$R_{2-6}$ are each, independently, H, halo, OH, $NO_2$, $NH_2$, lower alkyl, O-lower alkyl, NH-lower alkyl, N(lower alkyl)$_2$, lower alkyl-N(lower alkyl)$_2$, lower alkyl-Si(lower alkyl)$_3$,

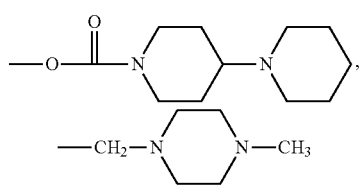

or linker-HSA binding moiety;
wherein
$R_4$ and $R_5$ optionally, together form —OCH$_2$CH$_2$O—,
$R_2$ and $R_3$ optionally, together form

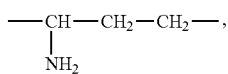

and
if $R_1$ is OH, then at least one of $R_{2-6}$ must be linker-HSA binding moiety;
linker-HSA binding moiety is:

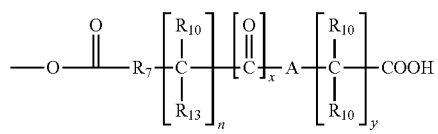

wherein
A is

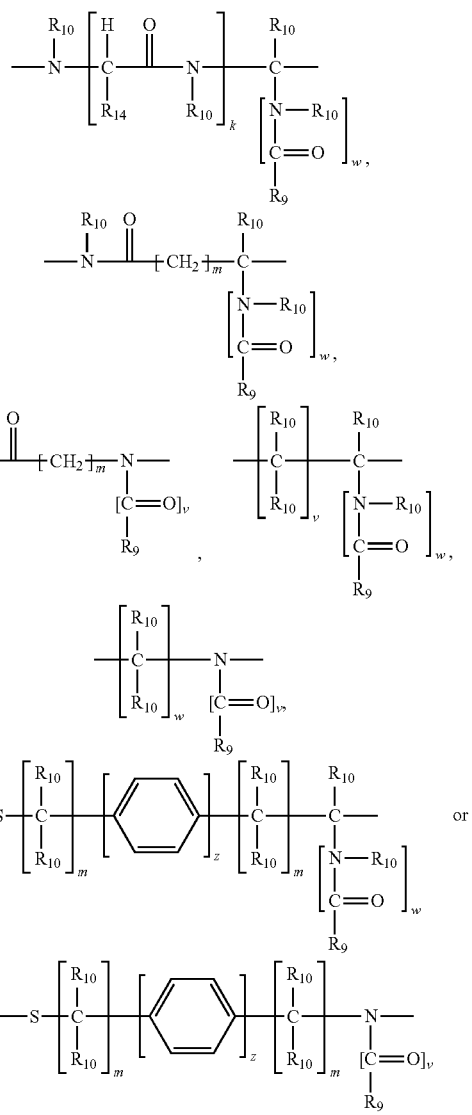

$R_7$ is O, NH or a covalent bond;
$R_9$ is an unbranched or branched alkyl, alkylene or alkyne of 2 to 30 carbon atoms optionally including one or more ring structures of 3 to 6 atoms when $R_9$ has at least 7 carbon atoms, and including heteroatoms of oxygen in an integer number from 0 to one fifth the total number of carbon atoms in $R_9$, with the proviso that there be no covalent bonds between oxygen atoms in $R_9$;
$R_{10}$ is, independently in each instance, H or lower alkyl;
$R_{13}$ is, independently in each instance, H, OH, $NO_2$, $NH_2$, $NH_3^+$, SH or a branched or unbranched alkyl, alkylene or alkyne of 1 to 8 carbon atoms, wherein the alkyl, alkylene or alkyne is optionally substituted with one or two substituents selected from the group consisting of halo, OH, $NO_2$, $NH_2$, $NH_3^+$, SH and =O, and optionally includes up to two heteroatoms independently selected from O, S and N, with the proviso that no O, S or N atom in the alkyl, alkylene or alkyne is covalently bonded to any other O, S or N atom;

$R_{14}$ is, independently in each instance, H, OH, $NO_2$, $NH_2$, $NH_3^+$, SH or a branched or unbranched alkyl, alkylene or alkyne of 1 to 10 carbon atoms, wherein the alkyl, alkylene or alkyne optionally includes one or more ring structures of 3 to 9 atoms, is optionally substituted with one or two substituents selected from the group consisting of halo, OH, $NO_2$, $NH_2$, $NH_3^+$, SH and =O, and optionally includes up to two heteroatoms independently selected from O, S and N, with the proviso that no O, S or N atom in the alkyl, alkylene or alkyne is covalently bonded to any other O, S or N atom;

k is 0, 1 or 2;

m, independently in each instance, is 0, 1, 2 or 3;

n is 1, 2 or 3;

v is 0 or 1;

w is 0 or 1;

x is 0 or 1, with the proviso that x is 0 when a di-sulfide bond is present in A;

y is 0, 1, 2 or 3; and z is 0 or 1 wherein the compound comprises no more than two linker-HSA binding moieties.

The present invention further provides pharmaceutically acceptable salts, isomers, enantiomers, diastereomers and corresponding mixtures of the compounds of Formula I. The present invention also provides therapeutic methods of administering compounds of Formula I for the treatment of proliferative disorders, such as cancer. The present invention further provides therapeutic methods of administering a compound of Formula I for the treatment of diseases responding to inhibition of Topoisomerase I, such as for example tumors, HIV infections and parasitic infections.

DETAILED DESCRIPTION

General Definitions

The following definitions refer to the various terms used above and throughout the disclosure.

The term "halo" refers to fluoro, chloro, bromo or iodo.

The term "alkyl" refers to a straight or branched chain alkyl group, having from 1-30 carbon atoms. Illustrative of the alkyl group include the methyl, ethyl, propyl, isopropyl, butyl, isobutyl, sec-butyl, t-butyl, pentyl, 3-methylbutyl, 2,2-dimethylpropyl, 1,1-dimethylpropyl, hexyl, 1-methylpentyl, 4-methylpentyl, heptyl, 1-methylhexyl, 2-methylhexyl, 5-methylhexyl, 3-ethylpentyl, octyl, 2-methylheptyl, 6-methylheptyl, 2-ethylhexyl, 2-ethyl-3-methylpentyl, 3-ethyl-2-methylpentyl, nonyl, 2-methyloctyl, 7-methyloctyl, 4-ethylheptyl, 3-ethyl-2-methylhexyl, 2-ethyl-1-methylhexyl, decyl, 2-methylnonyl, 8-methylnonyl, 5-ethyloctyl, 3-ethyl-2-methylheptyl, 3,3-diethylhexyl, undecyl, 2-methyldecyl, 9-methyldecyl, 4-ethylnonyl, 3,5-dimethylnonyl, 3-propyloctyl, 5-ethyl-4-methyloctyl, 1-pentylhexyl, dodecyl, 1-methylundecyl, 10-methylundecyl, 3-ethyldecyl, 5-propylnonyl, 3,5-diethyloctyl, tridecyl, 11-methyldodecyl, 7-ethylundecyl, 4-propyldecyl, 5-ethyl-3-methyldecyl, 3-pentyloctyl, tetradecyl, 12-methyltridecyl, 8-ethyldodecyl, 6-propylundecyl, 4-butyldecyl, 2-pentylnonyl, pentadecyl, 13-methyltetradecyl, 10-ethyltridecyl, 7-propyldodecyl, 5-ethyl-3-methyldodecyl, 4-pentyldecyl, 1-hexylnonyl, hexadecyl, 14-methylpentadecyl, 6-ethyltetradecyl, 4-propyltridecyl, 2-butyldodecyl, heptadecyl, 15-methylhexadecyl, 7-ethylpentadecyl, 3-propyltetradecyl, 5-pentyldodecyl, octadecyl, 16-methylheptadecyl, 5-propylpentadecyl, nonadecyl, 17-methyloctadecyl, 4-ethylheptadecyl, icosyl, 18-methylnonadecyl, 3-ethyloctadecyl, henicosyl, docosinyl, tricosinyl, tetracosinyl and pentacosinyl groups.

The term "alkylene" represents an alkenyl group, having from 2 to 30 carbon atoms, and may be a straight or branched chain group. It may have 1 or more, preferably from 2 to 6, double bonds. Examples of such groups include the vinyl, alkyl, 1-propenyl, isopropenyl, 2-methyl-1-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 1-octenyl, 8-nonenyl, 1-nonenyl, 1-decenyl, 9-decenyl, 8-tridecenyl, cis-8-pentadecenyl, trans-8-pentadecenyl, 8-heptadecenyl, 8-heptadecenyl, 8,11-heptadecadienyl, 8,11,14-heptadecatrienyl, 4,7,11,14-nonadecatetraenyl and 2,6-dimethyl-8-(2,6,6-trimethyl-1-cyclohexen-1-yl)-1,3,5,7-nonatetraen-1-yl, cis-10-nonadecaenyl, 10,13-nonadecadienyl, cis-7,10,13-nonadecatrienyl, 5,8,11,14-nonadecatetraenyl, nonadecapentaenyl, henecosatetraenyl, henecosapentaenyl, henecosahexaenyl, myristyl, and eicosyl groups.

The term "alkyne" represents and alkynyl group, having from 2 to 30 carbon atoms, and may be a straight or branched chain group. In addition to one or more triple bonds, the alkyne group may have one or more double bonds.

When specifically stated, alkyl, alkylene or alkyne groups may include ring structures of 3 to 8 carbon atoms.

When an alkyl, alkylene or alkyne group is described as a "lower" alkyl, alkylene or alkyne group, it has a maximum of 6 carbon atoms.

When specifically stated, alkyl, alkylene or alkyne groups may include heteroatoms of oxygen, sulfur, nitrogen and/or silicon. Where specifically stated, alkyl, alkylene or alkyne groups may be substituted with halo, hydroxyl, nitro, amine, amide, sulfhydryl and carboxy groups. Illustrative examples of the alkyl group substituted with oxygen or including a heteroatom of oxygen include methoxymethyl, ethoxymethyl, propoxymethyl, n-butoxymethyl, 2-methoxyethyl, 2-ethoxyethyl, 2-propoxyethyl, 3-methoxypropyl, 3-ethoxypropyl, 3-propoxypropyl, 4-methoxybutyl, 4-propoxybutyl, dimethoxymethyl, 2,2-dimethoxyethyl, diethoxymethyl, 2,2-diethoxyethyl, dipropoxymethyl and 2,2-dipropoxyethyl groups. Illustrative examples of the alkyl group substituted with sulfur are methylthiomethyl, ethylthiomethyl, propylthiomethyl, n-butylthiomethyl, 2-methylthiolethyl, 2-ethylthiolethyl, 2-propylthiolethyl, 3-methylthiopropyl, 3-ethylthiopropyl, 3-propylthiopropyl, 4-methylthiobutyl, and 4-propylthiobutyl groups. Illustrative examples of the alkyl group substituted with nitrogen are aminomethyl, dimethylaminomethyl, (N-acetyl)methylaminomethyl, diethylaminomethyl, dipropylaminomethyl, dibutylaminomethyl, dimethylaminoethyl, diethylaminoethyl, dipropylaminoethyl, and dibutylaminoethyl groups. Illustrative examples of the alkyl group substituted with silicon are trimethylsilyl, triethylsilyl, tributylsilyl, t-butyldimethylsilyl, t-butyldiethylsilyl and t-butyldiphenylsilyl.

The term "group of natural amino acid side chains" represents the set of chemical groups attached to the alpha carbon for each of the twenty naturally-occurring amino acids: Cysteine, Histidine, Isoleucine, Methionine, Serine, Valine, Alanine, Glycine, Leucine, Proline, Threonine, Phenylalanine, Arginine, Tyrosine, Tryptophan, Aspartic Acid, Asparagine, Glutamic Acid, Glutamine and Lysine.

A "pharmaceutically acceptable salt" includes a salt with an inorganic base, organic base, inorganic acid, organic acid, or basic or acidic amino acid. Salts of inorganic bases include, for example, alkali metals such as sodium or potassium; alkaline earth metals such as calcium and magnesium or aluminum; and ammonia. Salts of organic bases include, for example, trimethylamine, triethylamine, pyridine, picoline, ethanolamine, diethanolamine, and triethanolamine. Salts of inorganic acids include for example, hydrochloric acid, hydroboric acid, nitric acid, sulfuric acid, and phosphoric acid. Salts of organic acids include for example, formic acid, acetic acid, trifluoroacetic acid, fumaric acid, oxalic acid, tartaric acid, maleic acid, citric acid, succinic acid, malic acid, methanesulfonic acid, benzenesulfonic acid, and p-toluenesulfonic acid. Salts of basic amino acids include, for example, arginine, lysine and ornithine. Acidic amino acids include, for example, aspartic acid and glutamic acid.

As utilized herein the term "cancer" refers to all known forms of cancer including, solid forms of cancer (e.g., tumors), lymphomas, and leukemias.

As used herein "anti-neoplastic agent" or "anti-cancer agent" or "anti-tumor agent" refer to an agent that reduces, prevents, mitigates, limits, and/or, delays the deleterious physiological manifestations, the growth or metastases of neoplasms, or by killing neoplastic cells directly by necrosis or apoptosis of neoplasms or any other mechanism.

As used herein, an "effective amount" or a "pharmaceutically-effective amount" in reference to the compounds or compositions of the instant invention refers to the amount sufficient to induce a desired biological, pharmacological, or therapeutic outcome in a subject. That result can be reduction, prevention, mitigation, delay, shortening the time to resolution of, alleviation of the signs or symptoms of, or exert a medically-beneficial effect upon the underlying pathophysiology or pathogenesis of an expected or observed side-effect, toxicity, disorder or condition, or any other desired alteration of a biological system. In cancer treatment, the result will generally include the reduction, prevention, mitigation, limitation, and/or, delay of the deleterious physiological manifestations, growth or metastases of neoplasms.

In one aspect of the invention, novel analogs of camptothecin according to Formula I are provided.

In a particular embodiment of Formula I, the novel analog of camptothecin comprises one linker-HSA binding moiety.

In another particular embodiment of Formula I, the novel analog of camptothecin comprises two linker-HSA binding moieties.

In a further particular embodiment of Formula I, the linker-HSA binding moiety comprises:

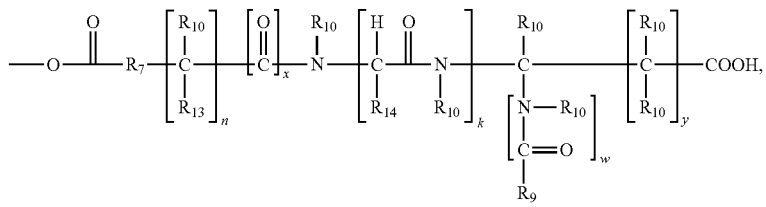

or more particularly:

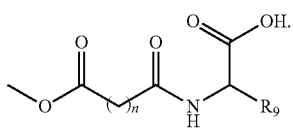

In another particular embodiment of Formula I, the linker-HSA binding moiety comprises:

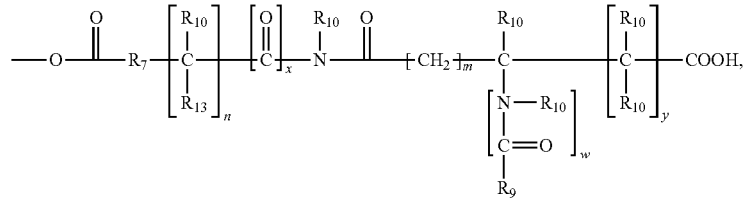

or more particularly,

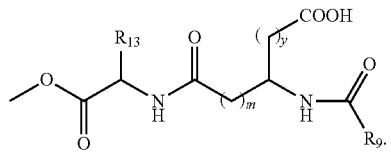

In a further particular embodiment of Formula I, the linker-HSA binding moiety comprises:

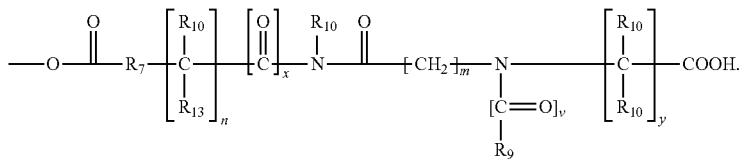

In another particular embodiment of Formula I, the linker-HSA binding moiety comprises:

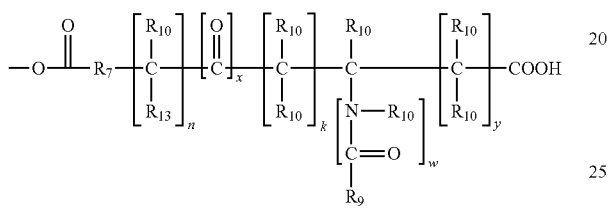

In a further particular embodiment of Formula I, the linker-HSA binding moiety comprises:

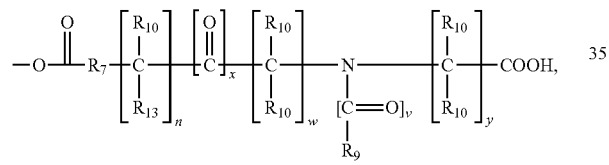

or more particularly,

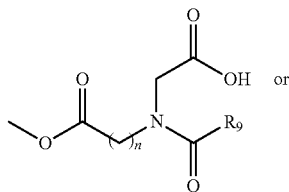

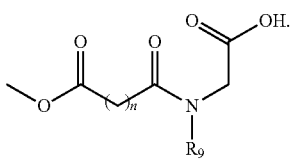

In another particular embodiment of Formula I, the linker-HSA binding moiety comprises:

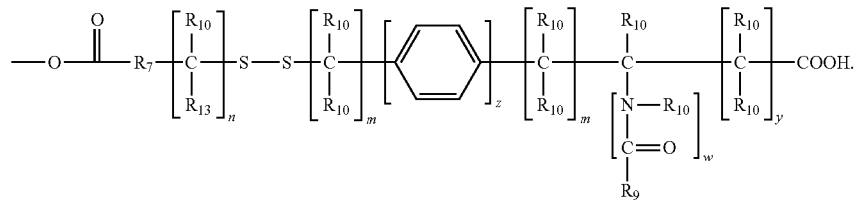

In a further particular embodiment of Formula I, the linker-HSA binding moiety comprises:

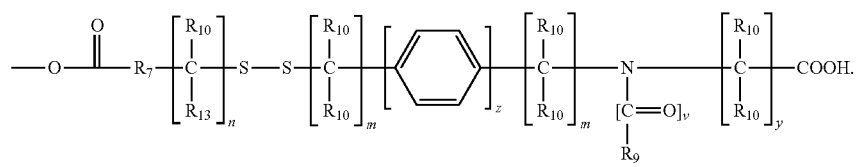

In another particular embodiment of Formula I, the linker-HSA binding moiety is defined as one of the other particular embodiments and $R_{13}$ is selected from the group of natural amino acid side chains.

In a further particular embodiment of Formula I, the linker-HSA binding moiety is defined as one of the other particular embodiments and $R_{14}$ is selected from the group of natural amino acid side chains.

In another particular embodiment of Formula I, the linker-HSA binding moiety is defined as one of the other particular embodiments and $R_7$ is a covalent bond.

In a further particular embodiment of Formula I, the linker-HSA binding moiety is defined as one of the other particular embodiments and $R_7$ is —O—.

In another particular embodiment of Formula I, the linker-HSA binding moiety is defined as one of the other particular embodiments and $R_7$ is —NH—.

In a further particular embodiment of Formula I, a compound selected from camptothecin, Irinotecan, Topotecan, SN-38, 9-Aminocamptothecin, 9-Nitrocamptothecin, GI-147211, Exatecan and Karenitecin is bound at the $R_1$ and/or $R_4$ site to the inker-HSA binding moiety as defined as one of the other particular embodiments.

In another particular embodiment of Formula I, Topotecan is bound at the $R_1$ and/or $R_4$ site to the inker-HSA binding moiety as defined as one of the other particular embodiments.

In a further particular embodiment of Formula I, Irinotecan is bound at the $R_1$ site to the inker-HSA binding moiety as defined as one of the other particular embodiments.

In another particular embodiment of Formula I, SN-38 is bound at the $R_1$ and/or $R_4$ site to the inker-HSA binding moiety as defined as one of the other particular embodiments.

In another particular embodiment of Formula I, the linker-HSA binding moiety is defined as one of the other particular embodiments and $R_9$ has from 4 to 30 carbon atoms.

In another particular embodiment of Formula I, the linker-HSA binding moiety is defined as one of the other particular embodiments and $R_9$ has from 6 to 30 carbon atoms.

In a further particular embodiment of Formula I, the linker-HSA binding moiety is defined as one of the other particular embodiments and $R_9$ has from 2 to 6 carbon atoms.

In another particular embodiment of Formula I, the linker-HSA binding moiety is defined as one of the other particular embodiments and $R_9$ has from 2 to 8 carbon atoms.

In a further particular embodiment of Formula I, the linker-HSA binding moiety is defined as one of the other particular embodiments and $R_9$ has from 2 to 10 carbon atoms.

In another particular embodiment of Formula I, the linker-HSA binding moiety is defined as one of the other particular embodiments and $R_9$ has from 2 to 12 carbon atoms.

In a further particular embodiment of Formula I, the linker-HSA binding moiety is defined as one of the other particular embodiments and $R_9$ has from 2 to 16 carbon atoms.

In another particular embodiment of Formula I, the linker-HSA binding moiety is defined as one of the other particular embodiments and $R_9$ has from 4 to 8 carbon atoms.

In a further particular embodiment of Formula I, the linker-HSA binding moiety is defined as one of the other particular embodiments and $R_9$ has from 4 to 10 carbon atoms.

In another particular embodiment of Formula I, the linker-HSA binding moiety is defined as one of the other particular embodiments and $R_9$ has from 4 to 12 carbon atoms.

In a further particular embodiment of Formula I, the linker-HSA binding moiety is defined as one of the other particular embodiments and $R_9$ has from 4 to 16 carbon atoms.

In another particular embodiment of Formula I, the linker-HSA binding moiety is defined as one of the other particular embodiments and $R_9$ has from 8 to 16 carbon atoms.

In a further particular embodiment of Formula I, the linker-HSA binding moiety is defined as one of the other particular embodiments and $R_9$ has from 16 to 30 carbon atoms.

In another aspect of the invention, novel analogs of camptothecin according to Formula I are provided which, when subject to the HSA binding assay described below, are bound at least 70% to HSA. In a particular embodiment, the novel analogs of camptothecin are bound at least 80% to HSA. In a further particular embodiment, the novel analogs of camptothecin are bound at least 85% to HSA. In yet another particular embodiment, the novel analogs of camptothecin are bound at least 90% to HSA. In yet another particular embodiment, the novel analogs of camptothecin are bound at least 95% to HSA. In yet another particular embodiment, the novel analogs of camptothecin are bound at least 97% to HSA.

In another aspect of the invention, novel analogs of camptothecin according to Formula I are provided which, when incubated at a concentration of 10 μM with human plasma at 37° C. for 60 minutes and quenched by addition of acetonitrile, have at least 30% of the lactone form of the novel analog of camptothecin remaining. In a particular embodiment, the novel analogs of camptothecin have at least 50% of the lactone form of the novel analog of camptothecin remaining. In a further particular embodiment, the novel analogs of camptothecin have at least 60% of the lactone form of the novel analog of camptothecin remaining. In yet another particular embodiment, the novel analogs of camptothecin have at least 70% of the lactone form of the novel analog of camptothecin remaining. In yet another particular embodiment, the novel analogs of camptothecin have at least 80% of the lactone form of the novel analog of camptothecin remaining. In yet another particular embodiment, the novel analogs of camptothecin have at least 85% of the lactone form of the novel analog of camptothecin remaining. In yet another particular embodiment, the novel analogs of camptothecin have at least 90% of the lactone form of the novel analog of camptothecin remaining. In yet another particular embodiment, the novel analogs of camptothecin have at least 95% of the lactone form of the novel analog of camptothecin remaining.

In another aspect of the invention, a method is provided to inhibit the enzyme topoisomerase I in an animal in need thereof, comprising administering to the animal an effective amount of a composition comprising one of the above particular embodiments of Formula I. More particularly, the administration of the composition may be orally, parenterally, intramuscularly, transdermally, intravenously or by an airborne delivery system.

In a further aspect of the invention, a method is provided to treat cancer in a patient comprising administering a composition comprising one of the above particular embodiments of Formula I to said patient in an effective amount to treat said cancer. More particularly, the cancer to be treated in this aspect of the invention may be a solid tumor or blood borne tumor, the cancer may be selected from lung cancer, breast cancer, colon cancer, prostate cancer, melanoma, pancreatic cancer, stomach cancer, liver cancer, brain cancer, kidney cancer, cancer of the uterus, cancer of the cervix, ovarian cancer, cancer of the urinary tract, gastrointestinal cancer and leukemia. More particularly, the administration of the composition may be orally, parenterally, intramuscularly, transdermally, intravenously or by an airborne delivery system.

Synthesis of camptothecin and camptothecin analogs, including Topotecan, Irinotecan, SN-38, 9-Aminocamptothecin, 9-Nitrocamptothecin, GI-147211, Exatecan and Karenitecin is well-documented in the literature and well-known to those of skill in the art of organic synthesis. Furthermore, camptothecin and several of the camptothecin analogs are commercially available. The following Schemes 1-4 are generic synthesis methods for making compounds of the present invention from camptothecin or camptothecin analogs. For conciseness, the Schemes are depicted for compounds of Formula I, wherein $R_7$ is a covalent bond. It is well within the ability of a skilled organic chemist to adapt these Schemes for synthesis of compounds of Formula I wherein $R_7$ is O or NH.

Scheme 1

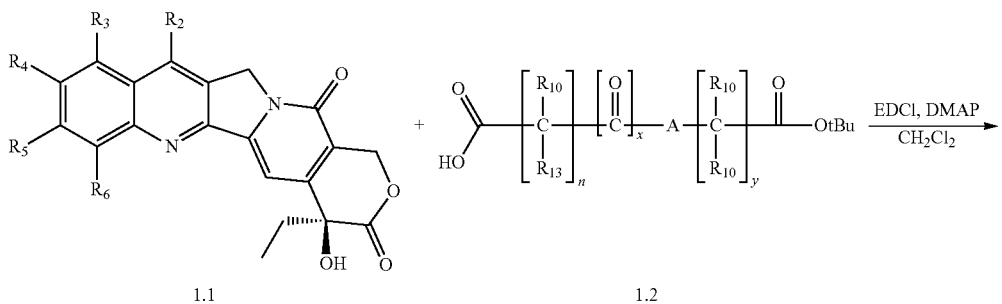

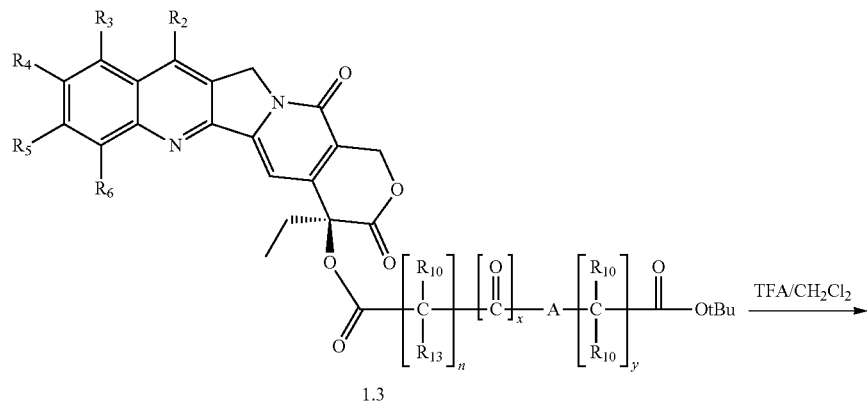

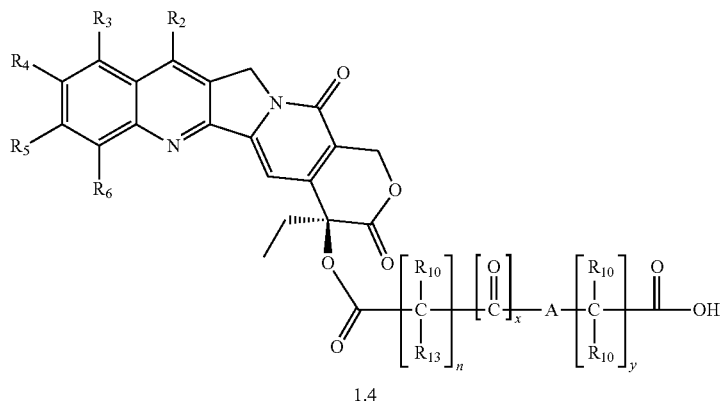

Scheme 2
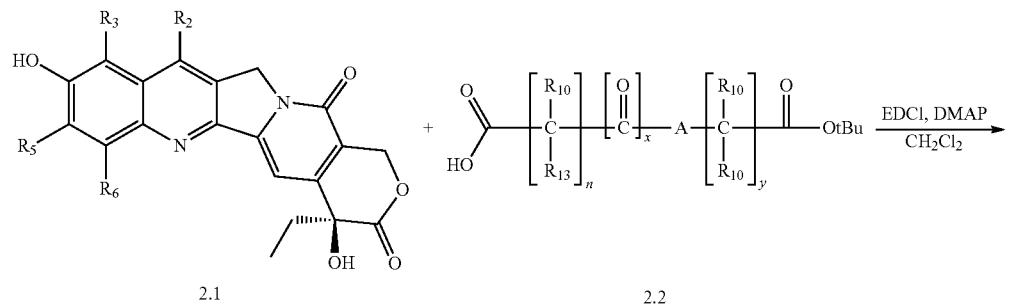
2.1       2.2
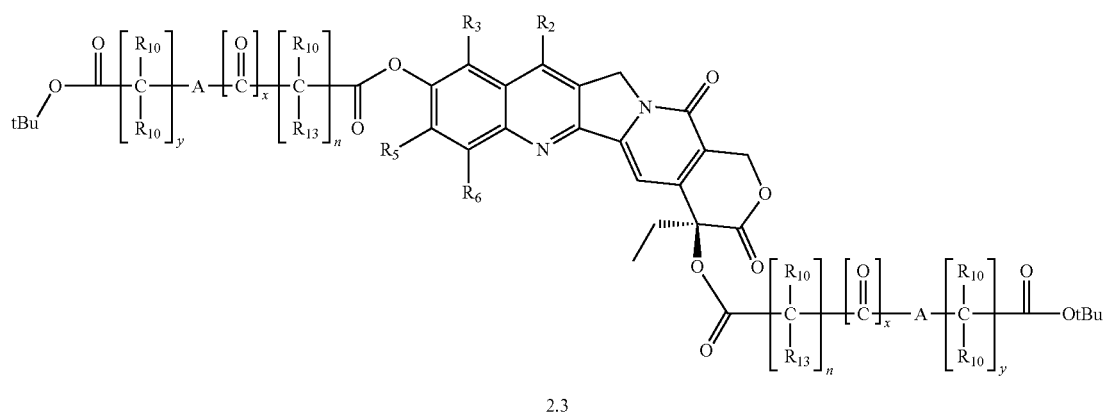
2.3
TFA/CH₂Cl₂ ↓
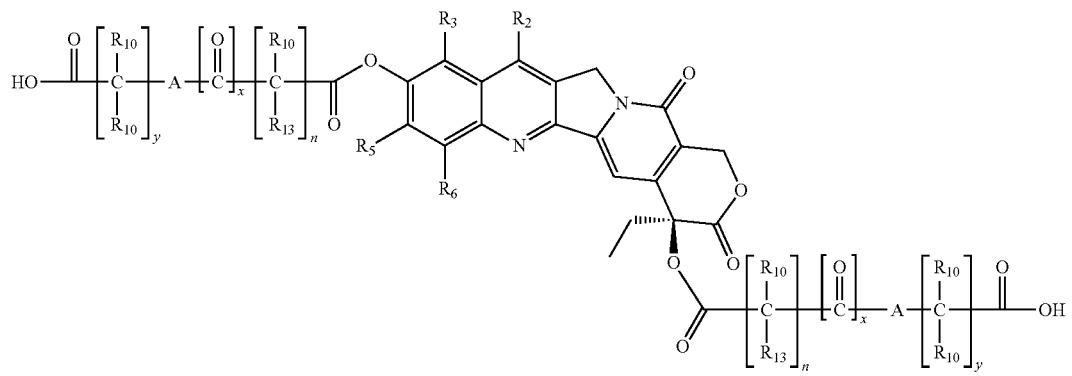
2.4

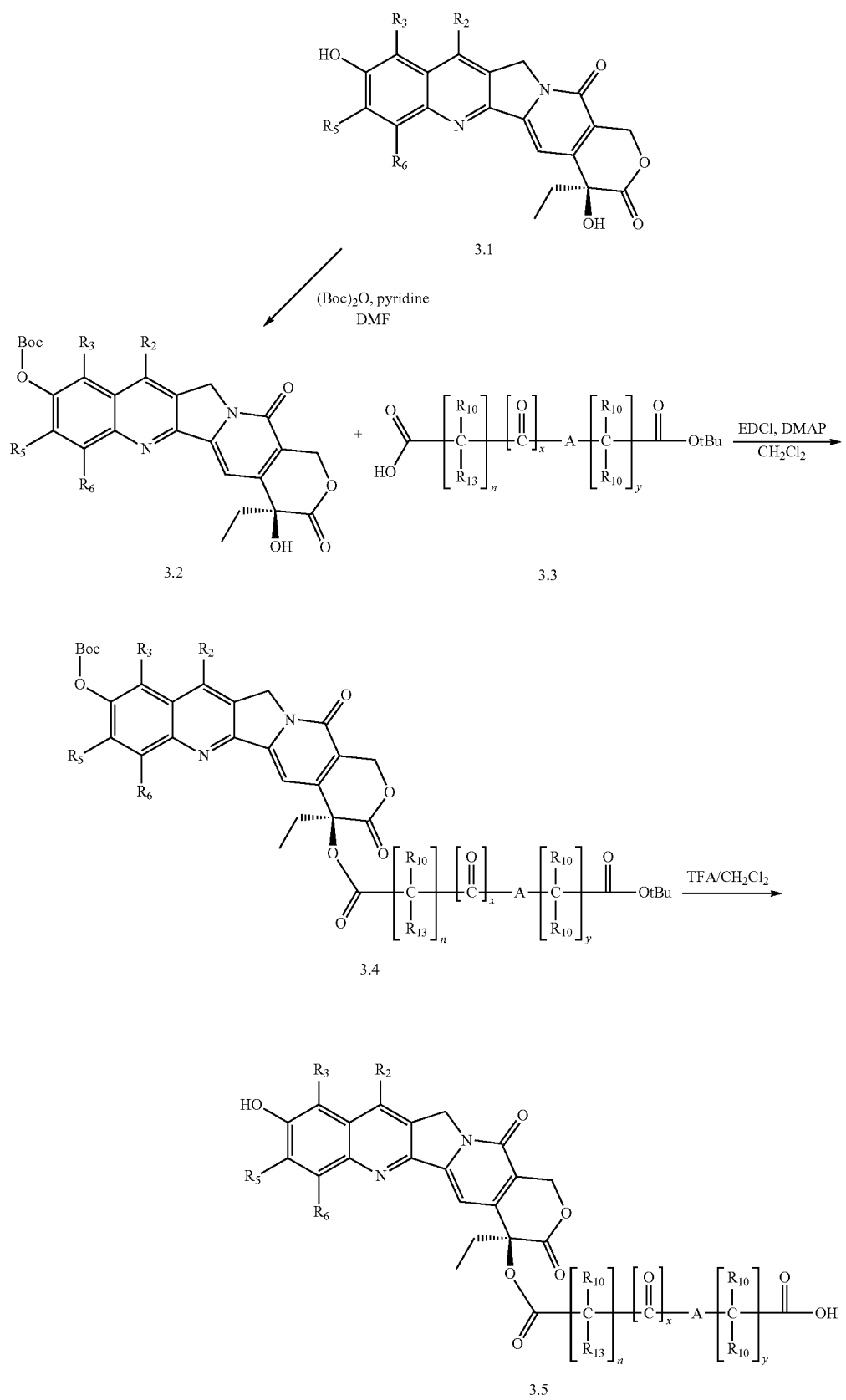

Scheme 4

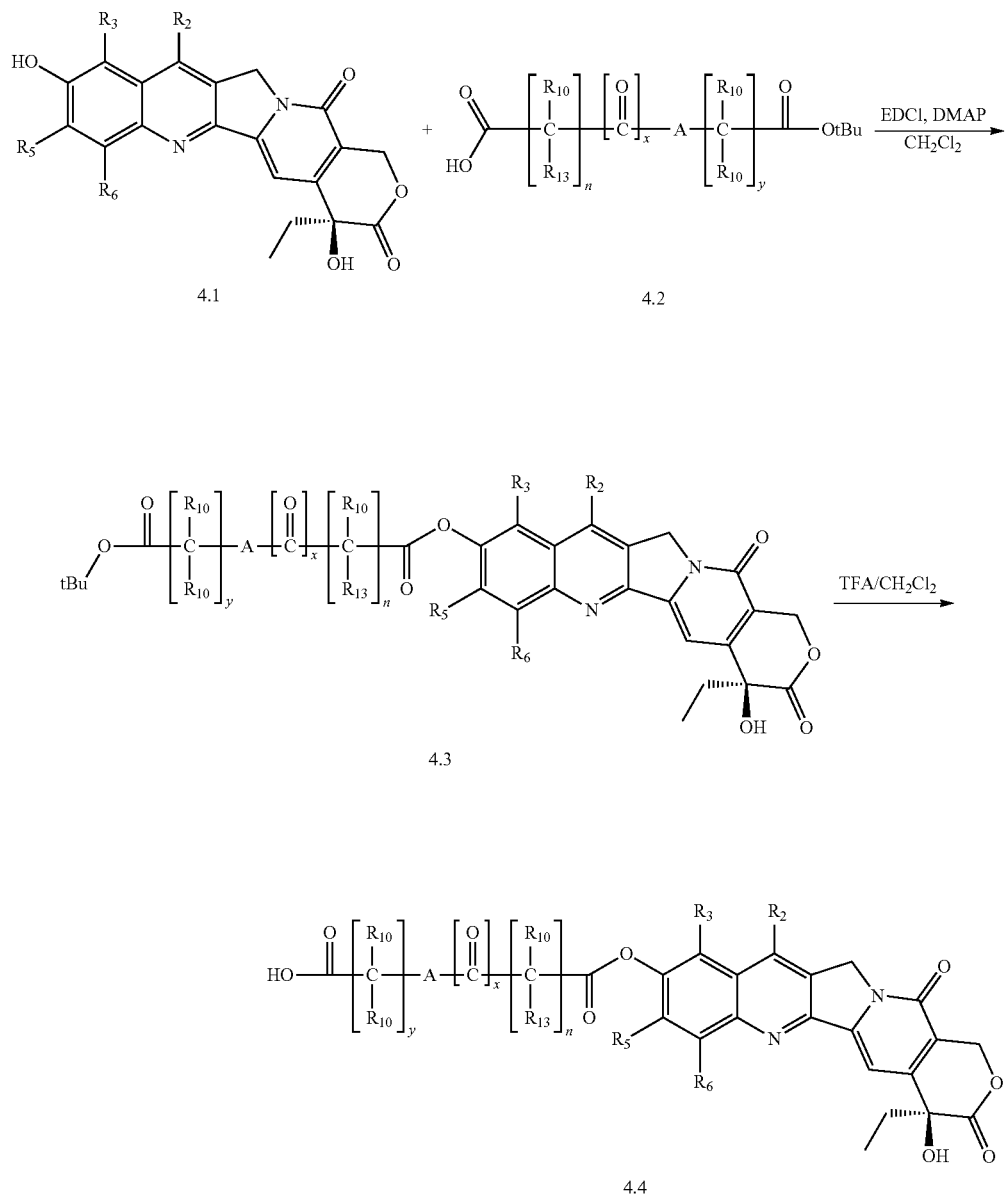

In a further aspect, the invention relates to pharmaceutical compositions containing a compound of Formula I together with pharmaceutically acceptable carriers and excipients. The pharmaceutical forms suitable to the oral or parenteral administration of the compounds of Formula I can be solid, preferably capsules, tablets and granules, or liquid, preferably injectable or infusion solutions.

The suitably formulated compounds of the invention can be used for the treatment of diseases responding to inhibition of Topoisomerase I, such as for example tumors, HIV infections and parasitic infections. In particular, the suitably formulated compounds of the invention can be used for the treatment of solid tumors and leukemias, including tumors of the lung, ovary, breast, stomach, liver, prostate, soft tissue sarcomas, head and neck, esophagus, pancreas, colon, rectum, glioblastoma, chronic and acute myelocytic leukemias. One of skill in the arts of pharmacology can prepare the compounds of Formula I into suitable forms and dosages for desired routes of administration based on the abundant knowledge in the art of other camptothecin analogs that have been used pharmacologically and/or clinically. For instance, European Patent 2007386 B1 by inventor Frederick H. Hausheer, entitled "CAMPTOTHECIN-ANALOG WITH A NOVEL, FLIPPED LACTONE-STABLE, E-RING AND METHODS FOR MAKING AND USING SAME", teaches the previous clinical and/or pharmacological use of more than a dozen camptothecin analogues, and is herein incorporated by reference.

EXAMPLES
Example 1
Synthesis of FL-001
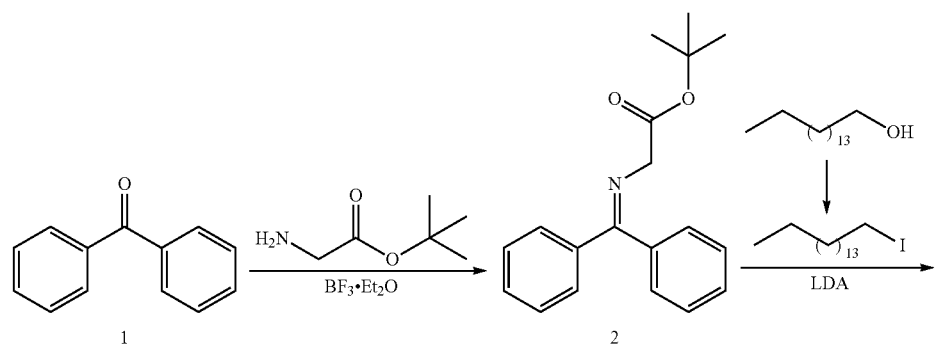
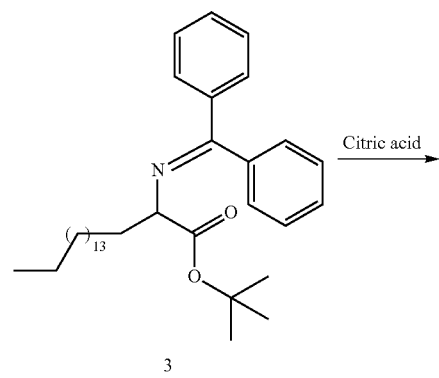
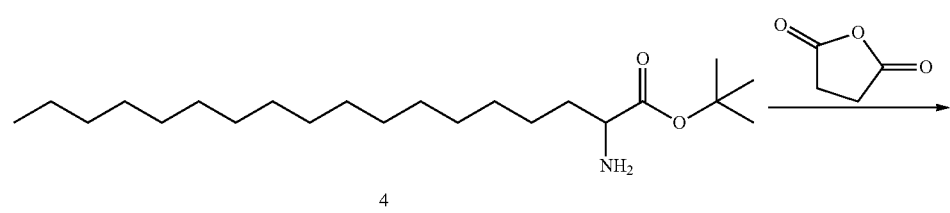

-continued
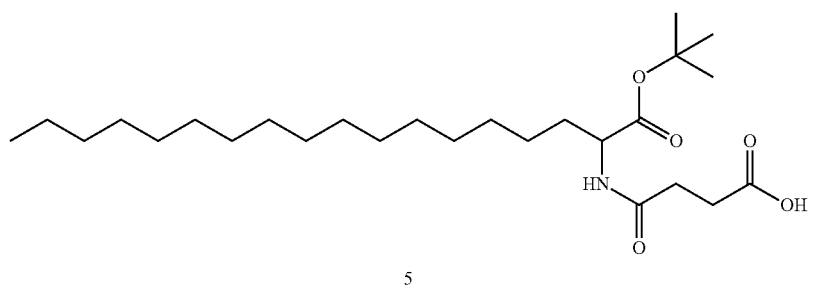
5
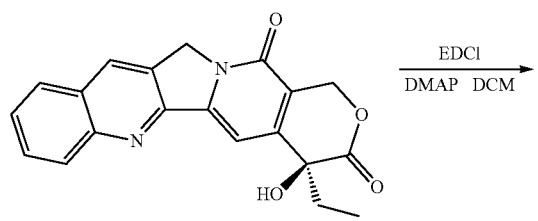
$\xrightarrow{\text{EDCl}}_{\text{DMAP DCM}}$
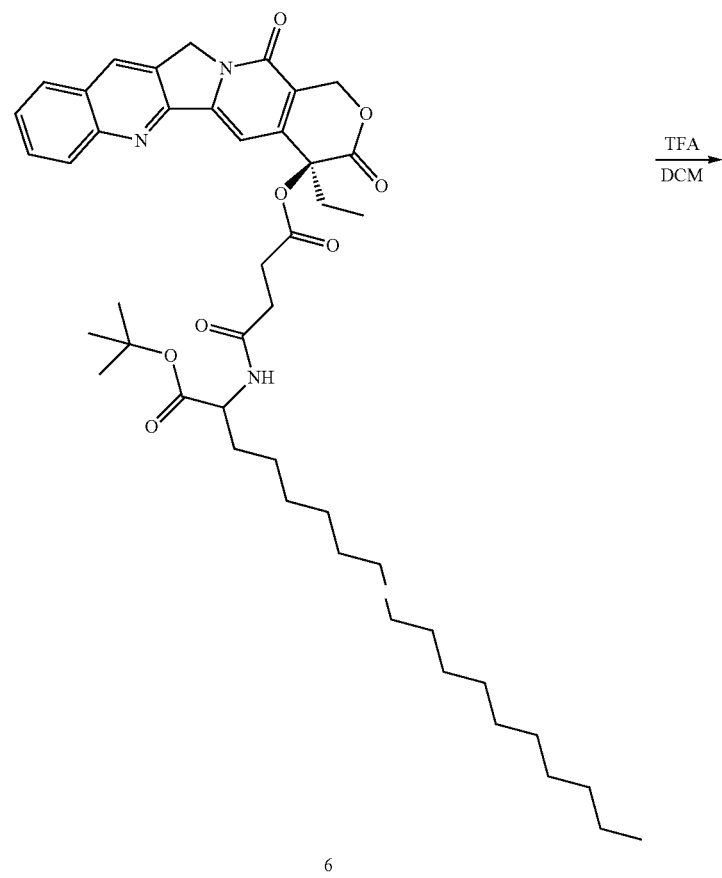
$\xrightarrow{\text{TFA}}_{\text{DCM}}$
6

-continued

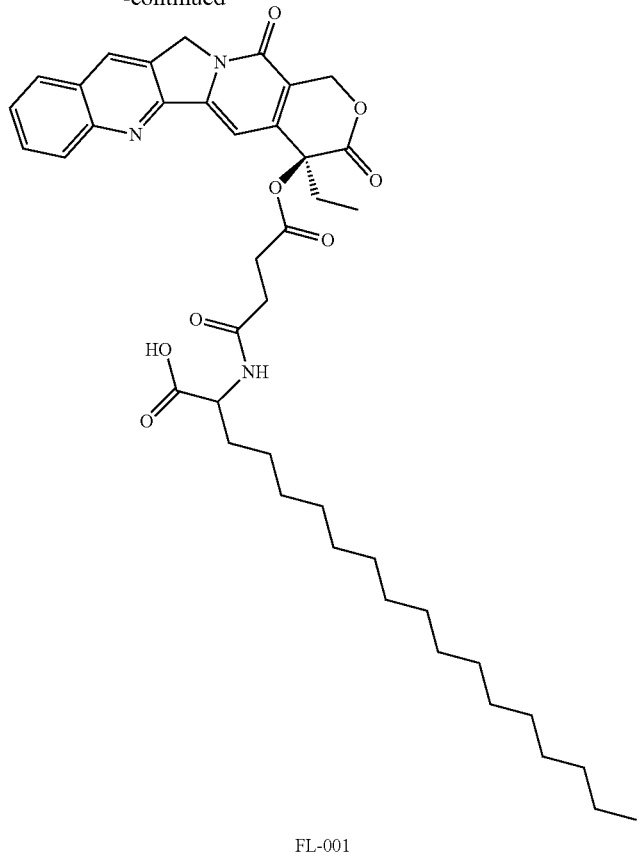

FL-001

1. Benzophenone (50 g) and glycine tert-butyl ester (30 g) were dissolved in 300 ml toluene and 2 ml of boron trifluoride etherate was added as a catalyst. The reaction mixture was refluxed for overnight. The solvent was removed on vacuum to give a crude product of as a white solid. The solid material obtained after evaporation was crystallized twice in hexane/diethyl ether (20:1.v/v) to give a pure product of 2 (28.5 g) as a white solid.

1H NMR (300 MHz, CDCl$_3$) 7.6-7.7 (m, 2H), 7.4-7.5 (m, 3H), 7.3-7.4 (m, 3H), 7.1-7.2 (m, 2H), 4.1-4.2 (m, 2H), 1.4-1.5 (m, 9H).

2. Compound 2 (28.5 g) in THF (150 ml) was added to LDA (2.2 eq) and kept at −78° C. in dry THF (150 ml) under nitrogen. After 30 min, 1-iodohexadecane (33 g) was added to the reaction mixture. After 2 h, the mixture was allowed to warm slowly to room temperature and stirred overnight. The reaction was quenched by addition of water (100 ml) to the mixture at 0° C. The mixture was then extracted with CH$_2$Cl$_2$ (200 ml*3), the product was purified by silica gel column and recrystallized by 5% EA/PE to give compound 3 (21 g) as a white solid.

1H NMR (300 MHz, CDCl$_3$) 7.6-7.7 (m, 2H), 7.4-7.5 (m, 3H), 7.3-7.4 (m, 3H), 7.1-7.2 (m, 2H), 3.8-4.0 (m, 1H), 1.4-1.5 (s, 9H), 1.2-1.4 (m, 30H), 0.8-1.0 (m, 3H).

3. To a solution of compound 3 (21 g) in 200 ml of THF at RT was added 210 ml of 10% aq. Citric acid. The mixture was stirred overnight. The reaction was quenched by addition of water (200 ml) to the mixture at 0° C. The pH value is adjusted to about 7 using NaHCO$_3$. The resulting mixture was extracted with CH$_2$Cl$_2$ (150 ml* *3). The organic phase was washed with saturated solution of sodium chloride and dried over Na$_2$SO$_4$. The solvent was removed on vacuum to give a crude product, which was purity by the silica gel column and recrystallized by 50% EA/PE to give compound 4 (9.5 g) as a white solid.

1H NMR (300 MHz, CDCl$_3$) 3.3-3.4 (1H), 1.4-1.5 (s, 9H), 1.2-1.4 (m, 30H), 0.8-1.0 (3H).

4. Compound 4 (3.41 g) was dissolved into 15 ml pyridine and cooled down in an ice bath. Dihydrofuran-2,5-dione (1.74 g) was added. The reaction was stirred at RT overnight. Volatiles were removed. The organic phase was separated and the aqueous phase was extracted with DCM, and washed with 2N HCl. The combined the organic phase was dried over Na$_2$SO$_4$ and concentrated to give compound 5 (3.2 g) as a white solid.

1H NMR (300 MHz, CDCl$_3$) 6.2-6.3 (bs, 1H), 4.4-4.5 (m, 1H), 2.7-2.8 (t, 2H), 2.5-2.6 (t, 2H), 1.8-1.9 (m, 1H), 1.4-1.5 (s, 9H), 1.2-1.4 (m, 29H), 0.8-0.9 (t, 3H).

5. Compound 5 (2.2 g) was dissolved into 30 ml DCM, and then EDCI (2.6 g), and DMAP (0.3 g) and camptothecin (1 g) were added. The reaction was maintained at 25° C. for 48 h, and TLC indicated reaction was completed. The organic phase was separated and the aqueous phase was extracted with DCM, and washed with NaHCO$_3$ (aq). The combined the organic phase was dried over Na$_2$SO$_4$ and concentrated, and the residue was purified by flash chromatography using 2% MeOH/CHCl$_3$ to give compound 6 (1.5 g) as a white solid.

1H NMR (300 MHz, CDCl$_3$) 8.4-8.5 (s, 1H), 8.2-8.3 (t, 1H), 7.9-8.0 (t, 1H), 7.8-7.9 (t, 1H), 7.6-7.7 (t, 1H), 7.3-7.4 (t, 1H), 6.0-6.2 (bs, 1H), 5.6-5.7 (d, 1H), 5.3-5.5 (d, 1H), 5.2-5.3 (s, 2H), 4.4-4.6 (m, 1H), 2.8-2.9 (t, 2H), 2.5-2.6 (t, 2H), 2.1-2.4 (m, 2H), 1.4-1.5 (s, 9H), 1.3-1.4 (m, 33H), 0.9-1.0 (t, 2H), 0.8-0.9 (m, 3H).

6. Compound 6 (0.3 g) was dissolved into 30 ml DCM, and TFA (1.5 ml) were added. The reaction was maintained at 25° C. for 12 h, and TLC indicated reaction was completed. The reaction mixture was concentrated, and the residue was purified by flash chromatography using 5% MeOH/CHCl$_3$ to give FL-001 (0.1 g) as a solid.
1H NMR (300 MHz, CDCl$_3$) 8.6-8.7 (s, 1H), 8.0-8.3 (m, 3H), 7.9-8.0 (t, 1H), 7.8-7.9 (t, 1H), 7.6-7.7 (t, 1H), 7.1-7.3 (d, 1H), 5.6-5.7 (s, 2H), 5.2-5.3 (d, 2H), 4.4-4.6 (m, 1H), 2.8-2.9 (t, 2H), 2.5-2.6 (t, 2H), 2.1-2.4 (m, 2H), 1.3-1.4 (m, 33H), 0.9-1.0 (t, 2H), 0.8-0.9 (m, 3H).
LCMS: 730.4 (M+1)$^+$
Example 2
Synthesis of FL-002
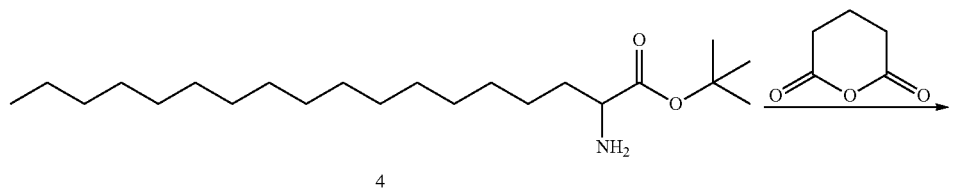
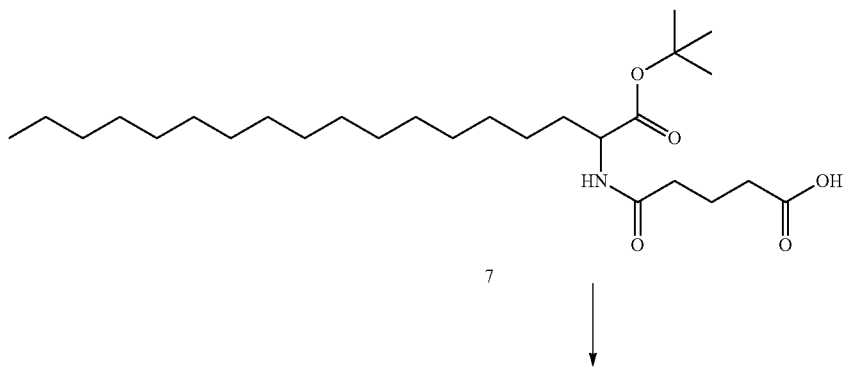
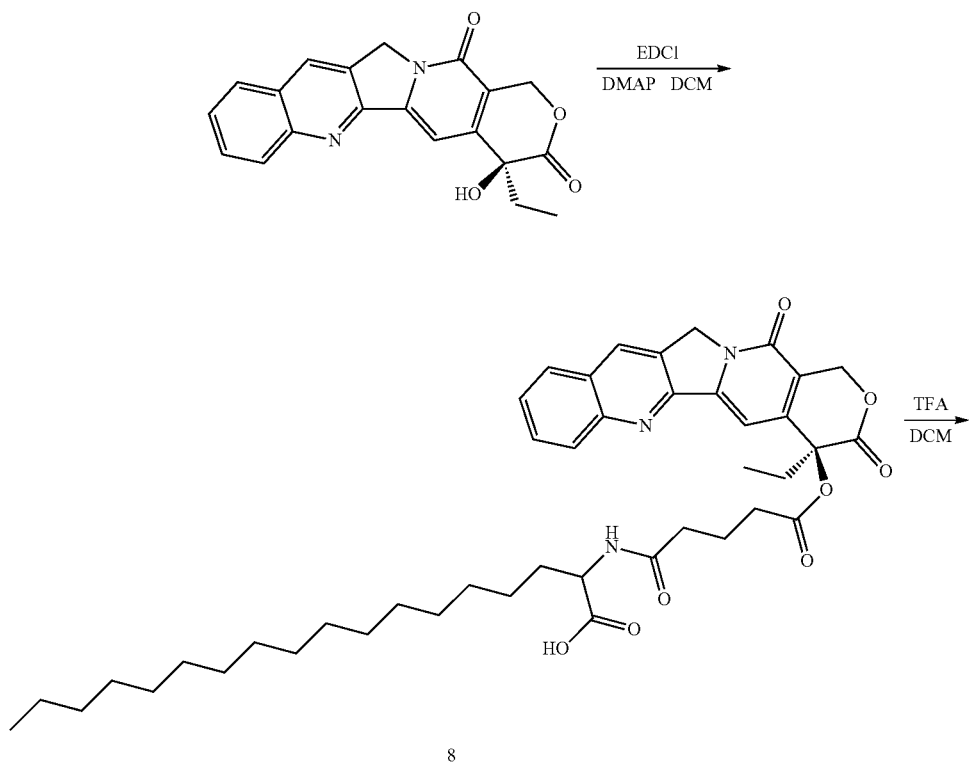

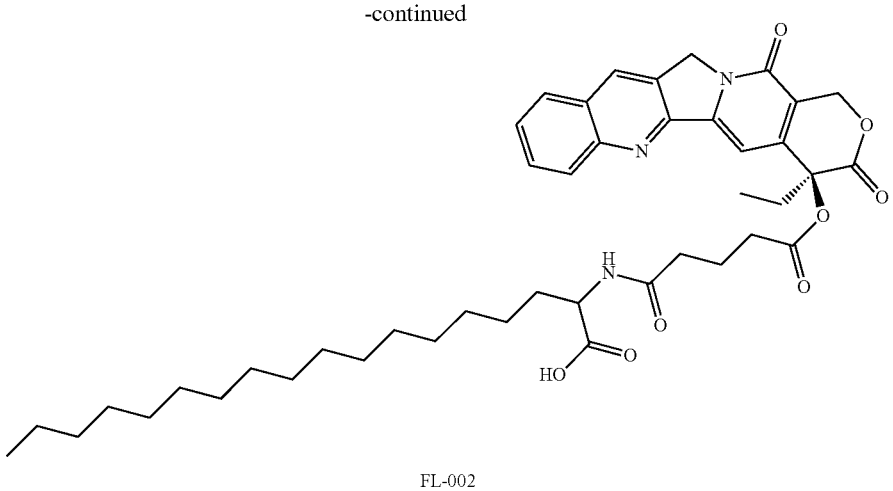

FL-002

1. Compound 4 (3.6 g) was dissolved into 15 ml pyridine and cooled down in an ice bath. Dihydro-2H-pyran-2,6(3H)-dione (1.8 g) was added. The reaction was stirred at RT overnight. Volatiles were removed. The organic phase was separated and the aqueous phase was extracted with DCM, and washed with 2N HCl. The combined the organic phase was dried over Na$_2$SO$_4$ and concentrated to give compound 7 (3.1 g) as a white solid.

1H NMR (300 MHz, CDCl$_3$) 6.2-6.3 (bs, 1H), 4.4-4.5 (m, 1H), 2.7-2.8 (t, 2H), 2.5-2.6 (t, 2H), 1.8-1.9 (m, 1H), 1.4-1.5 (s, 9H), 1.2-1.4 (m, 29H), 0.8-0.9 (t, 3H).

2. Compound 7 (2 g) was dissolved into 100 ml DCM, and then EDCI (1.3 g), and DMAP (0.15 g) and camptothecin (1 g) were added. The reaction was maintained at 25° C. for 48 h, and TLC indicated reaction was completed. The organic phase was separated and the aqueous phase was extracted with DCM, and washed with NaHCO$_3$ (aq). The combined the organic phase was dried over Na$_2$SO$_4$ and concentrated, and the residue was purified by flash chromatography using 2% MeOH/CHCl$_3$ to give compound 8 (0.6 g) as a white solid.

1H NMR (300 MHz, CDCl$_3$) 8.4-8.5 (s, 1H), 8.2-8.3 (t, 1H), 7.9-8.0 (t, 1H), 7.8-7.9 (t, 1H), 7.6-7.7 (t, 1H), 7.3-7.4 (t, 1H), 6.0-6.2 (bs, 1H), 5.6-5.7 (d, 1H), 5.3-5.5 (d, 1H), 5.2-5.3 (s, 2H), 4.4-4.6 (m, 1H), 2.8-2.9 (t, 2H), 2.5-2.6 (t, 2H), 2.1-2.4 (m, 2H), 1.4-1.5 (s, 9H), 1.3-1.4 (m, 33H), 0.9-1.0 (t, 2H), 0.8-0.9 (m, 3H).

3. Compound 8 (0.2 g) was dissolved into 30 ml DCM, and TFA (1.5 ml) were added. The reaction was maintained at 25° C. for 12 h, and TLC indicated reaction was completed. The mixture was concentrated, and the residue was purified by flash chromatography using 5% MeOH/CHCl$_3$ to give concentrated to give 0.15 g of FL-002 as a solid.

1H NMR (300 MHz, CDCl$_3$) 8.6-8.7 (s, 1H), 8.0-8.3 (m, 3H), 7.9-8.0 (t, 1H), 7.8-7.9 (t, 1H), 7.6-7.7 (t, 1H), 7.1-7.3 (d, 1H), 5.6-5.7 (s, 2H), 5.2-5.3 (d, 2H), 4.4-4.6 (m, 1H), 2.8-2.9 (t, 2H), 2.5-2.6 (t, 2H), 2.1-2.4 (m, 2H), 1.3-1.4 (m, 33H), 0.9-1.0 (t, 2H), 0.8-0.9 (m, 3H).

LCMS: 742.6 (M−1)$^-$

Example 3

Synthesis of FL-003

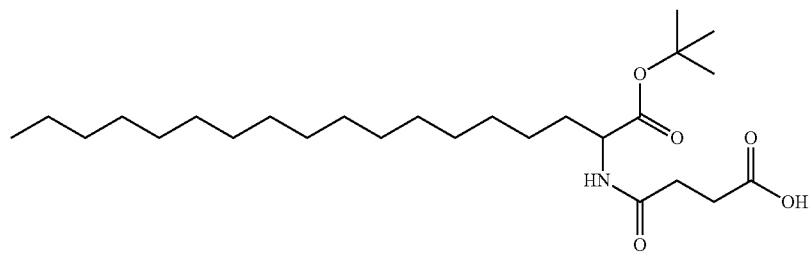

5

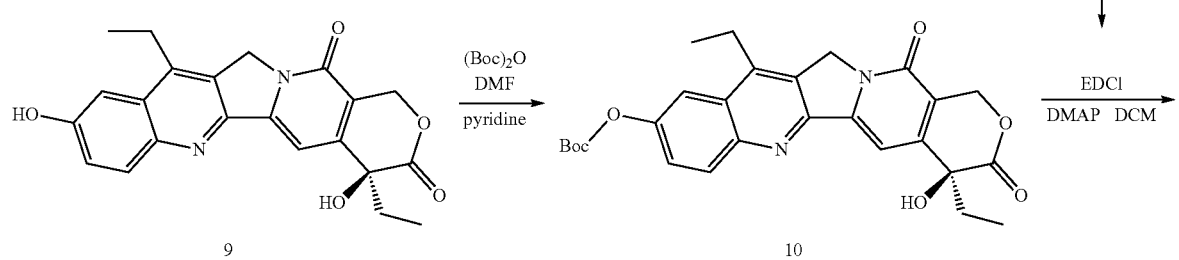

-continued
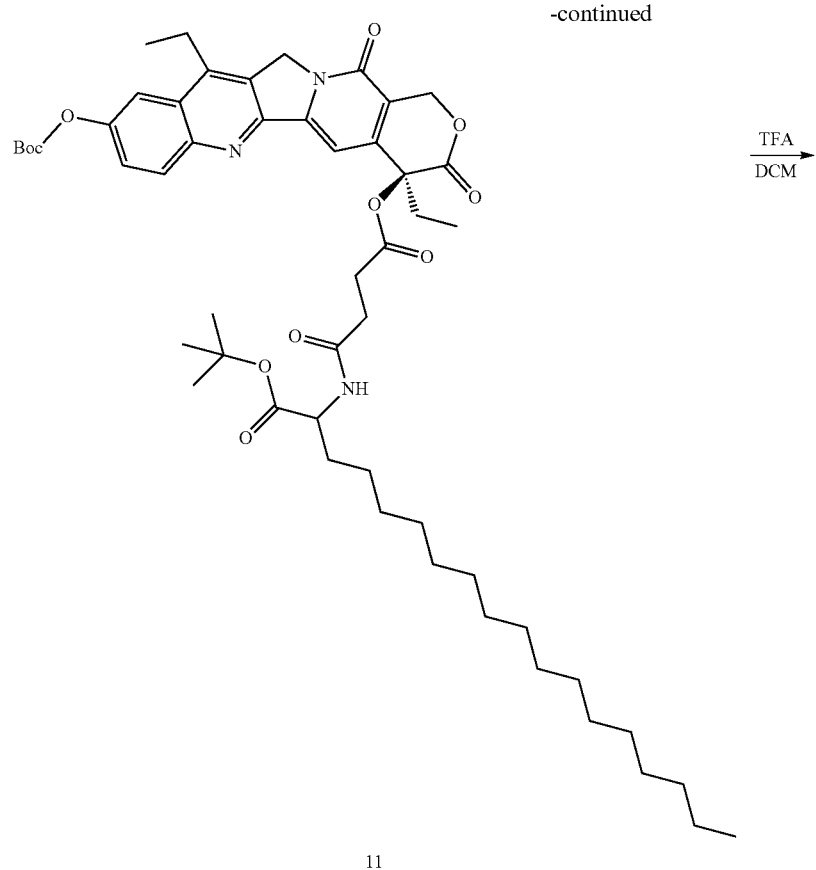
11
TFA / DCM
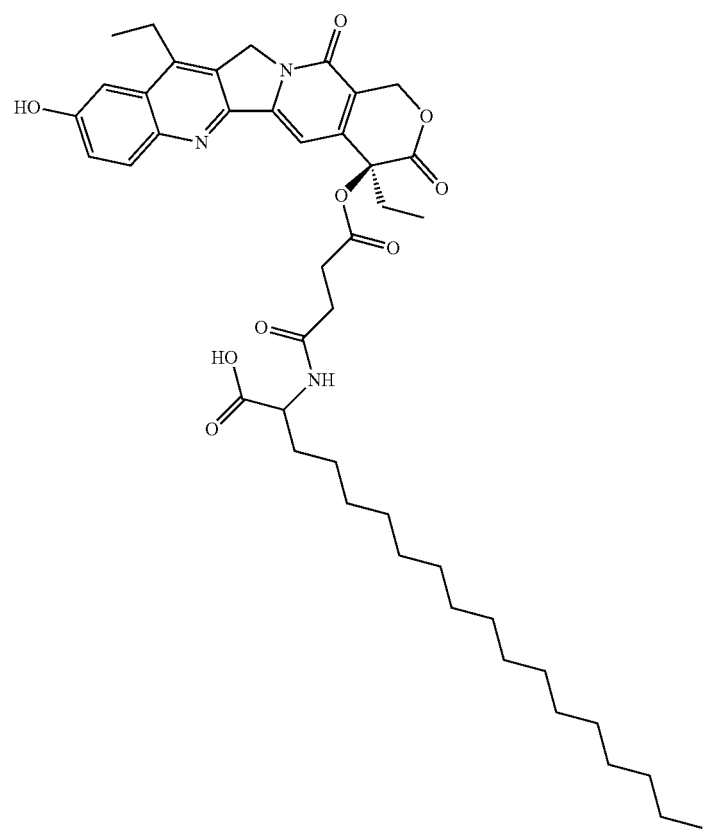
FL-003

1. Compound 9 (1.9 g) was dissolved into 15 ml pyridine and cooled down in an ice bath. (Boc)$_2$O (2.4 g) was added. The reaction was stirred at RT overnight. Volatiles were removed. The organic phase was separated and the aqueous phase was extracted with DCM, and washed with 1N HCl. The combined the organic phase was dried over Na$_2$SO$_4$ and concentrated to give compound 10 (2.0 g) as a white solid.

1H NMR (300 MHz, CDCl$_3$) 8.4-8.5 (s, 1H), 8.2-8.3 (t, 1H), 7.9-8.0 (t, 1H), 7.8-7.9 (t, 1H), 7.6-7.7 (t, 1H), 7.3-7.4 (t, 1H), 3.1-3.2 (t, 2H), 1.4-1.5 (s, 9H), 0.8-0.9 (m, 3H).

2. Compound 5 (2.2 g) was dissolved into 30 ml DCM, and then EDCI (1.2 g), and DMAP (0.16 g) and compound 10 (1 g) were added. The reaction was maintained at 25° C. for 48 h, and TLC indicated reaction was completed. The organic phase was separated and the aqueous phase was extracted with DCM, and washed with NaHCO$_3$ (aq). The combined the organic phase was dried over Na$_2$SO$_4$ and concentrated, and the residue was purified by flash chromatography using 2% MeOH/CHCl$_3$ to give compound 11 (0.6 g) as a white solid.

1H NMR (300 MHz, CDCl$_3$) 8.4-8.5 (s, 1H), 8.2-8.3 (D, 1H), 7.9-8.0 (s, 1H), 7.6-7.7 (d, 1H), 7.2-7.3 (t, 1H), 6.0-6.2 (bs, 1H), 5.6-5.7 (d, 1H), 5.3-5.5 (d, 1H), 5.2-5.3 (s, 2H), 4.4-4.6 (m, 1H), 3.1-3.2 (t, 2H), 2.8-2.9 (t, 2H), 2.5-2.6 (t, 2H), 2.1-2.4 (m, 2H), 1.4-1.5 (s, 9H), 1.3-1.4 (s, 9H), 1.2-1.3 (m, 33H), 0.9-1.0 (t, 2H), 0.8-0.9 (m, 3H), 0.7-0.8 (m, 3H).

3. Compound 11 (0.2 g) was dissolved into 30 ml DCM, and TFA (2 ml) were added. The reaction was maintained at 25° C. for 12 h, and TLC indicated reaction was completed. The reaction was concentrated, and the residue was purified by flash chromatography using 5% MeOH/CHCl$_3$ to give FL-003 (0.11 g) as a solid.

1H NMR (300 MHz, DMSO-d6) 10.2-10.6 (bs, 1H), 8.0-8.3 (m, 2H), 7.4-7.5 (t, 2H), 7.0-7.2 (d, 1H), 5.5-5.6 (s, 2H), 5.3-5.4 (s, 2H), 4.2-4.4 (m, 1H), 3.1-3.2 (t, 2H), 2.6-2.8 (m, 2H), 2.4-2.5 (t, 1H), 2.1-2.2 (m, 2H), 1.5-1.7 (m, 2H), 0.8-1.4 (m, 41H).

LCMS: 774.4 (M+1)$^+$

Example 4

Synthesis of FL-004

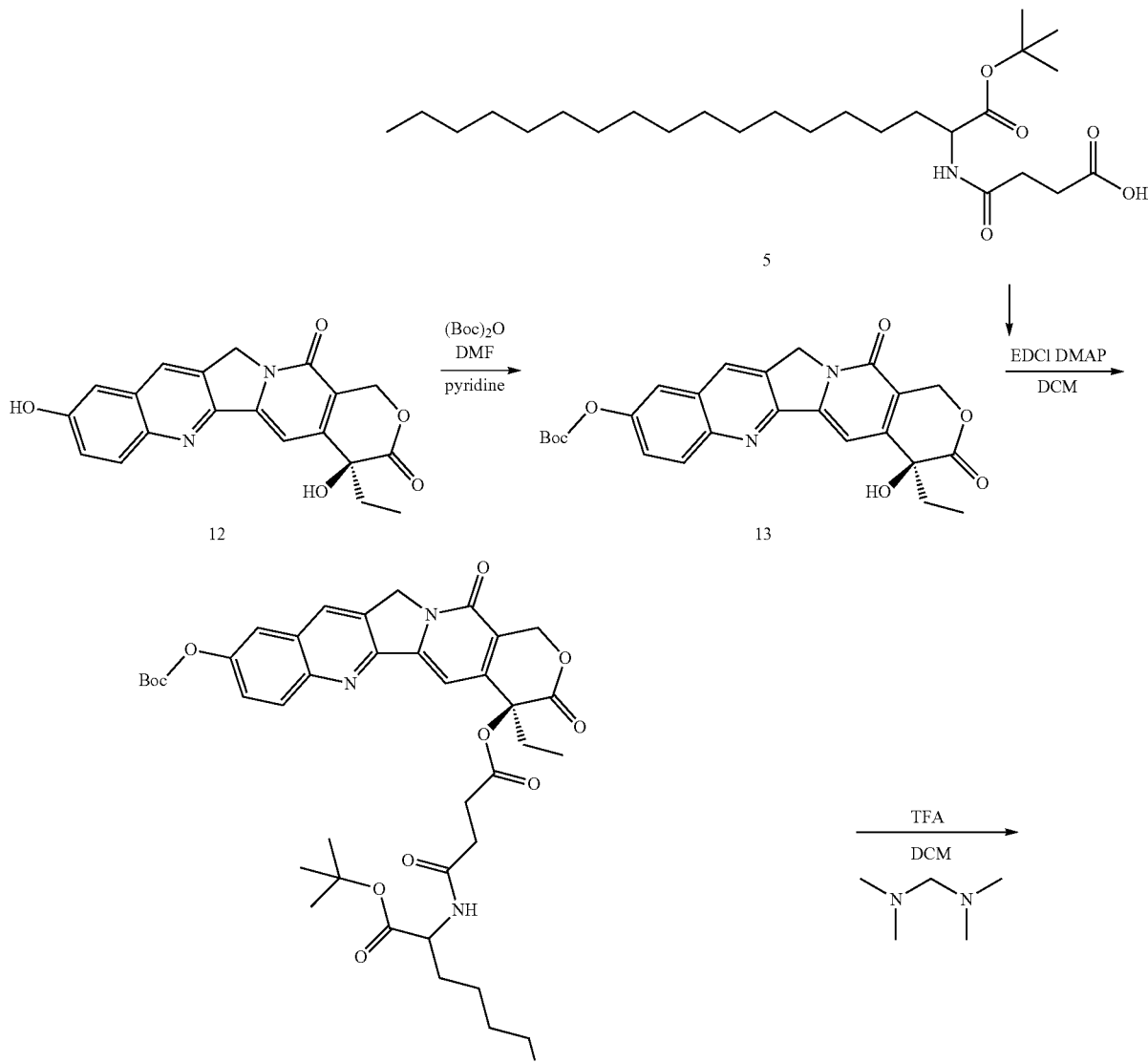

-continued

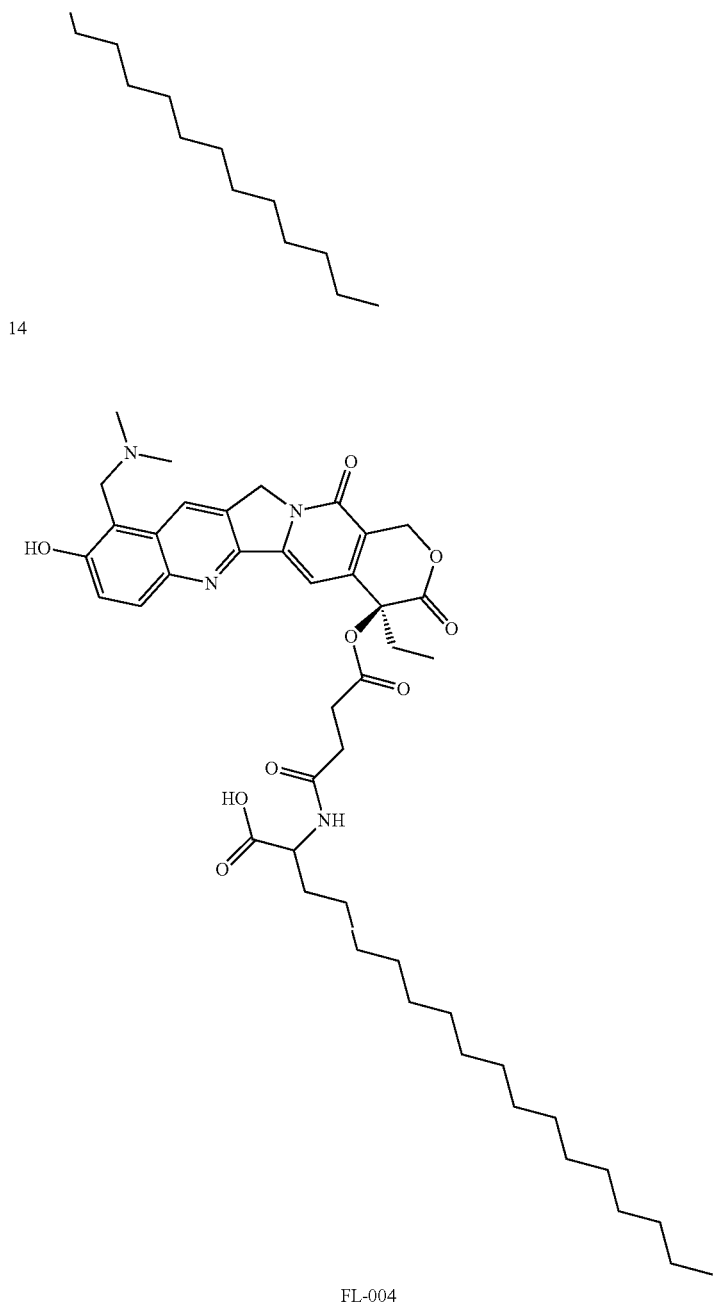

14

FL-004

1. Compound 12 (1.9 g) was dissolved into 15 ml pyridine and 30 ml DMF, and the mixture was cooled down in an ice bath. (Boc)₂O (2.4 g) was added. The reaction was stirred at RT overnight. Volatiles were removed. The organic phase was separated and the aqueous phase was extracted with DCM, and washed with 1N HCl. The combined organic phase was dried over Na₂SO₄ and concentrated to give compound 13 (2.1 g) as a white solid.

1H NMR (300 MHz, CDCl₃) 8.4-8.5 (s, 1H), 8.2-8.3 (t, 1H), 7.9-8.0 (t, 1H), 7.8-7.9 (t, 1H), 7.6-7.7 (t, 1H), 7.3-7.4 (t, 1H), 3.1-3.2 (t, 2H), 1.4-1.5 (s, 9H), 0.8-0.9 (m, 3H).

2. Compound 5 (1 g) was dissolved into 20 ml DCM, and then EDCI (1.2 g), and DMAP (0.1 g) and compound 13 (0.5 g) were added. The reaction was maintained at 25° C. for 48 h, and TLC indicated reaction was completed. The organic phase was separated and the aqueous phase was extracted with DCM, and washed with NaHCO₃ (aq). The combined the organic phase was dried over Na₂SO₄ and concentrated, and the residue was purified by flash chromatography using 2% MeOH/CHCl₃ to give compound 14 (0.25 g) as a white solid.

1H NMR (300 MHz, CDCl$_3$) 8.4-8.5 (s, 1H), 8.2-8.3 (D, 1H), 7.9-8.0 (s, 1H), 7.6-7.7 (d, 1H), 7.2-7.3 (t, 1H), 6.0-6.2 (bs, 1H), 5.6-5.7 (d, 1H), 5.3-5.5 (d, 1H), 5.2-5.3 (s, 2H), 4.4-4.6 (m, 1H), 3.1-3.2 (t, 2H), 2.8-2.9 (t, 2H), 2.5-2.6 (t, 2H), 2.1-2.4 (m, 2H), 1.4-1.5 (s, 9H), 1.3-1.4 (s, 9H), 1.2-1.3 (m, 33H), 0.9-1.0 (t, 2H), 0.8-0.9 (m, 3H), 0.7-0.8 (m, 3H).

3. Compound 14 (0.25 g) was dissolved into 10 ml DCM, and TFA (1.5 ml) were added. The reaction was maintained at 25° C. for 12 h, and TLC indicated reaction was completed. Bis-(dimethylamino)-methane (0.5 ml) was added slowly. The reaction was maintained at 25° C. for 12 h, and concentrated, and the residue was purified by reverse phase preparative HPLC using a gradient of water and MeOH with 0.1% trifluoroacetic acid to afford 100 mg of FL-004.

1H NMR (300 MHz, DMSO-d6) 10.2-10.6 (bs, 1H), 8.0-8.3 (m, 2H), 7.4-7.5 (t, 2H), 7.0-7.2 (d, 1H), 5.5-5.6 (s, 2H), 5.3-5.4 (s, 2H), 4.2-4.4 (m, 1H), 3.1-3.2 (t, 2H), 2.6-2.8 (m, 2H), 2.4-2.5 (t, 1H), 2.1-2.2 (m, 2H), 1.5-1.7 (m, 2H), 0.8-1.4 (m, 41H).

LCMS: 803.5 (M+1)$^+$

Example 5

Synthesis of FL-005

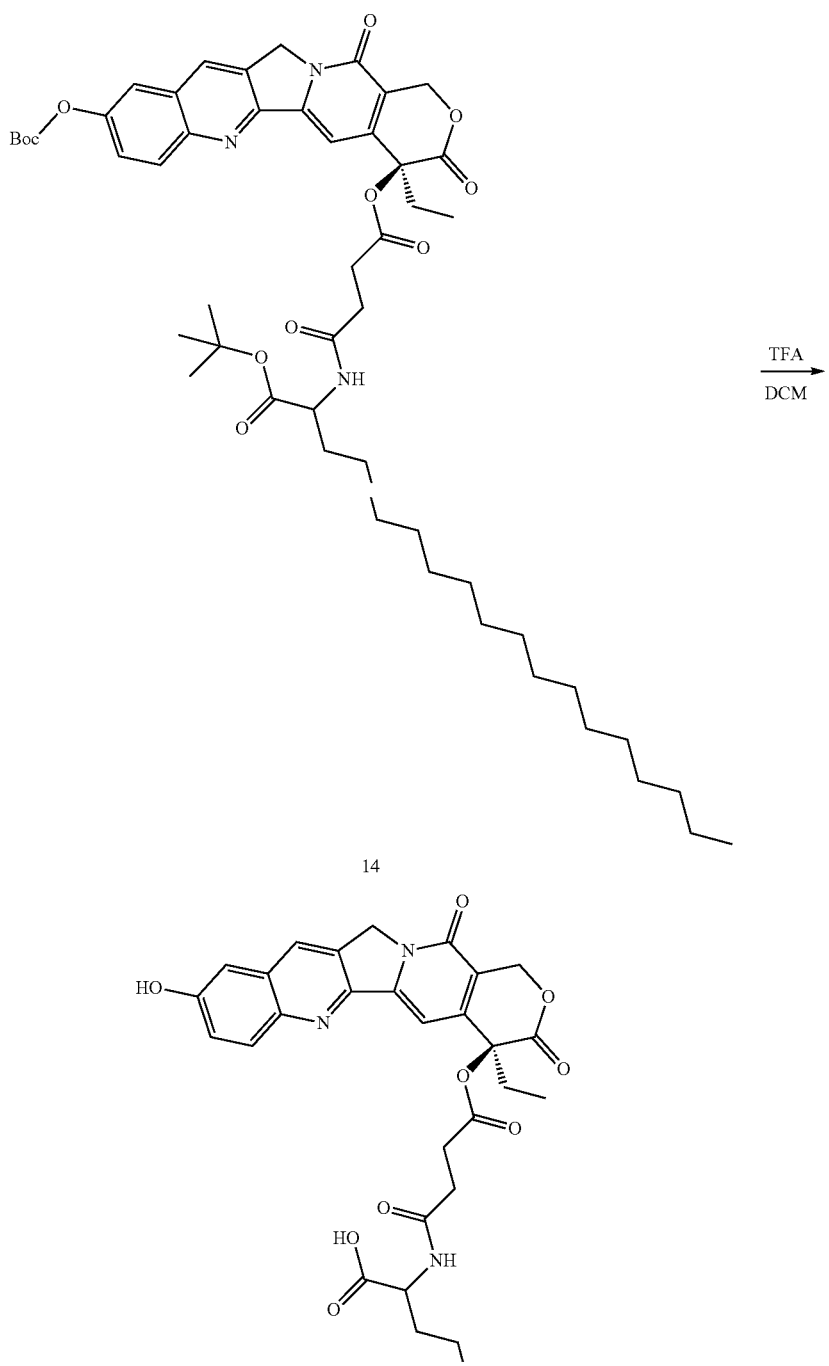

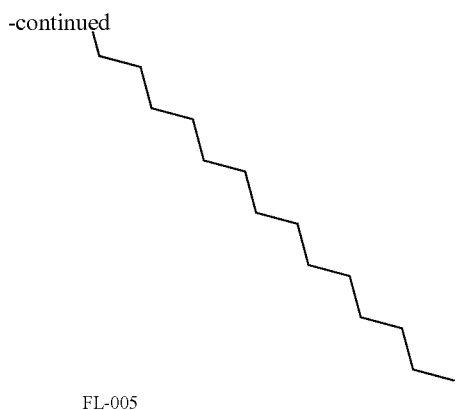
FL-005
1. Compound 14 (0.2 g) was dissolved into 10 ml DCM, and then TFA (1.5 ml) was added. The reaction was maintained at 25° C. for 12 h, and TLC indicated reaction was completed. The reaction mixture was concentrated, and the residue was purified by flash chromatography using 5% MeOH/CHCl₃ to give FL-005 (100 mg) as a solid.
1H NMR (300 MHz, DMSO-d6) 10.2-10.3 (bs, 1H), 8.4-8.5 (s, 1H) 8.0-8.3 (m, 2H), 7.4-7.5 (dt, 1H), 7.1-7.2 (s, 1H), 7.0-7.1 (d, 1H), 5.5-5.6 (s, 2H), 5.3-5.4 (s, 2H), 4.2-4.4 (m, 1H), 2.6-2.8 (m, 2H), 2.4-2.5 (t, 2H), 1.5-1.7 (m, 2H), 0.8-1.4 (m, 38H).
LCMS: 746.4 (M+1)⁺
Example 6
Synthesis of FL-006
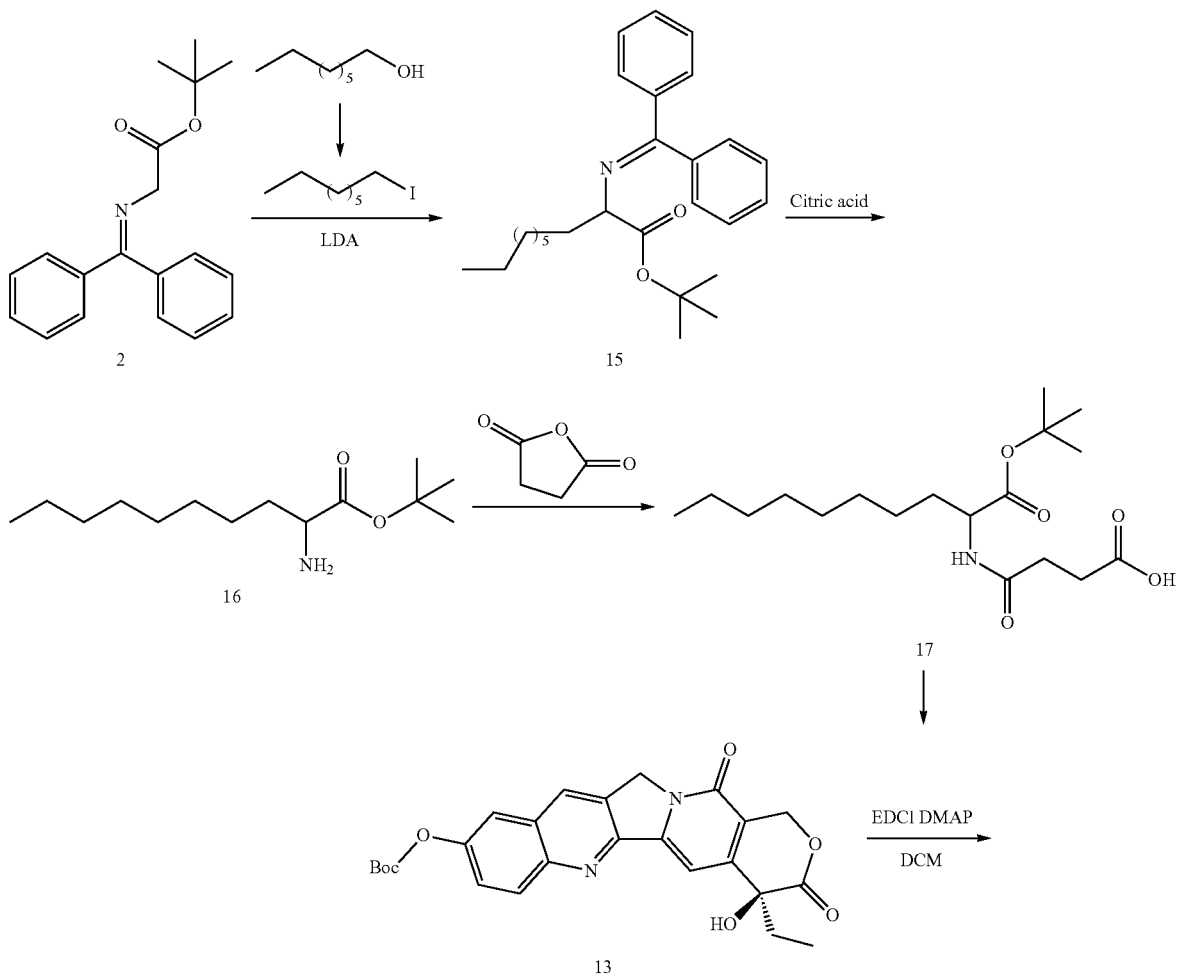

-continued

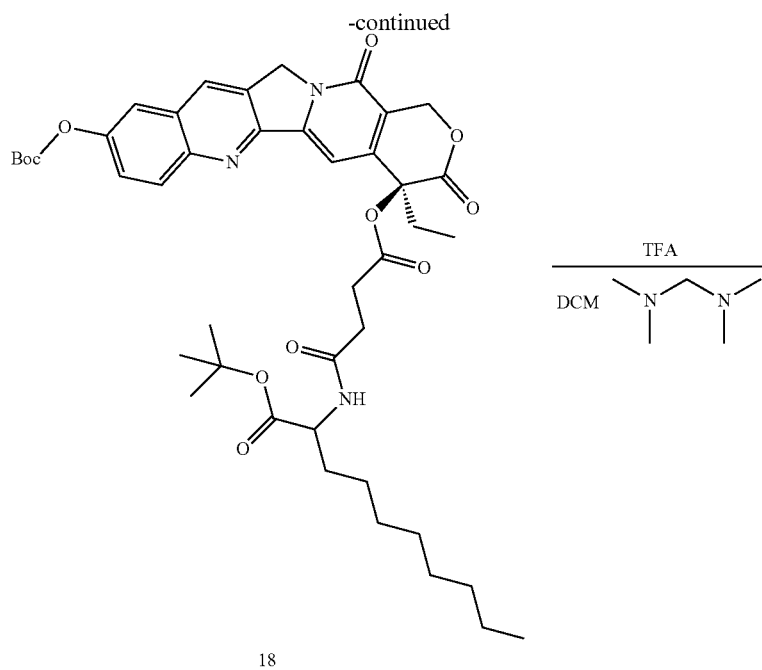

18

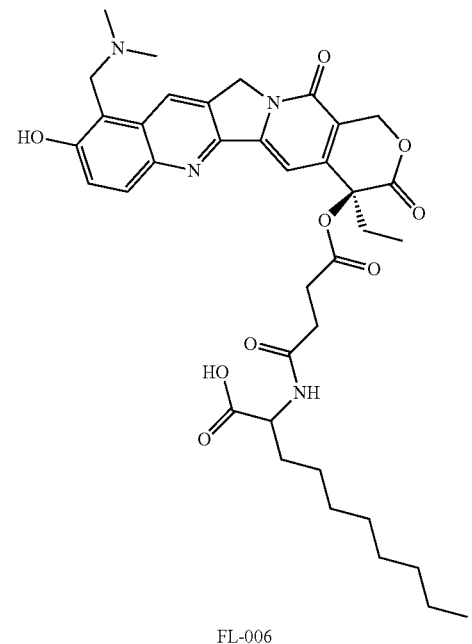 [SMILES: CCCCCCCCC(NC(=O)CCC(=O)O[C@]1(CC)C(=O)OCc2c1cc1n(c2=O)Cc2cc3c(CN(C)C)c(O)ccc3nc2-1)C(=O)O]

FL-006

1. Compound 2 (32 g) in THF (150 ml) was added to LDA (2.2 eq) and kept at −78° C. in dry THF (150 ml) under argon for 30 minutes. Then 1-iodoheptane (33 g) was added to the stirred mixture. After 2 h, the mixture was allowed to come slowly to room temperature and stirred overnight. The reaction was quenched by addition of water (100 ml) to the mixture at 0° C. The mixture was then extracted with $CH_2Cl_2$ (200 ml*3). The product was purified by column on silica gel and recrystallization by 5% EA/PE to give pure compound 15 (18 g) as a white solid.

1HNMR (300 MHz, $CDCl_3$) 7.6-7.7 (m, 2H), 7.4-7.5 (m, 3H), 7.3-7.4 (m, 3H), 7.1-7.2 (m, 2H), 3.8-4.0 (m, 1H), 1.4-1.5 (s, 9H), 1.2-1.4 (m, 30H), 0.8-1.0 (m, 3H).

2. To a solution of compound 15 (25 g) in 200 ml of THF at RT was added 210 ml of 10% aq. Citric acid. The mixture was stirred overnight. The reaction was quenched by addition of water (200 ml) to the mixture at 0° C. and adjust the pH value about 7 with $NaHCO_3$. The resultant mixture was extracted with $CH_2Cl_2$ (150 ml*3). Organic phase was washed with saturated solution of sodium chloride and dried over $Na_2SO_4$. The solvent was removed on vacuum to give a crude product, which was purified by column on silica gel and recrystallized by 50% EA/PE to give compound 16 (15 g) as a white solid.

1H NMR (300 MHz, $CDCl_3$) 3.3-3.4 (1H), 1.4-1.5 (s, 9H), 1.2-1.4 (m, 30H), 0.8-1.0 (3H).

3. Compound 16 (2.8 g) was dissolved into 15 ml pyridine and cooled down in an ice bath. Dihydrofuran-2,5-dione (1.5 g) was added. The reaction was stirred at RT overnight. Volatiles were removed. The organic phase was separated and the aqueous phase was extracted with DCM, and washed with 2N HCl. The combined the organic phase was dried over Na₂SO₄ and concentrated to give compound 17 (2.7 g) as a white solid.

1H NMR (300 MHz, CDCl₃) 6.2-6.3 (bs, 1H), 4.4-4.5 (m, 1H), 2.7-2.8 (t, 2H), 2.5-2.6 (t, 2H), 1.8-1.9 (m, 1H), 1.4-1.5 (s, 9H), 1.2-1.4 (m, 29H), 0.8-0.9 (t, 3H).

4. Compound 17 (2.7 g) was dissolved into 35 ml DCM, and then EDCI (1.4 g), and DMAP (0.13 g) and compound 13 (1.1 g) were added. The reaction was maintained at 25° C. for 48 h, and TLC indicated reaction was completed. The organic phase was separated and the aqueous phase was extracted with DCM, and washed with NaHCO₃ (aq). The combined the organic phase was dried over Na₂SO₄ and concentrated, and the residue was purified by flash chromatography using 2% MeOH/CHCl₃ to give compound 18 (1.25 g) as a white solid.

1H NMR (300 MHz, CDCl₃) 8.4-8.5 (s, 1H), 8.2-8.3 (d, 1H), 7.9-8.0 (s, 1H), 7.6-7.7 (d, 1H), 7.2-7.3 (t, 1H), 6.0-6.2 (bs, 1H), 5.6-5.7 (d, 1H), 5.3-5.5 (d, 1H), 5.2-5.3 (s, 2H), 4.4-4.6 (m, 1H), 3.1-3.2 (t, 2H), 2.8-2.9 (t, 2H), 2.5-2.6 (t, 2H), 2.1-2.4 (m, 2H), 1.4-1.5 (s, 9H), 1.3-1.4 (s, 9H), 1.2-1.3 (m, 14H), 0.9-1.0 (t, 2H), 0.8-0.9 (m, 3H), 0.7-0.8 (m, 3H).

5. Compound 18 (0.4 g) was dissolved into 10 ml DCM, and TFA (1.6 ml) was added. The reaction was maintained at 25° C. for 12 h, and TLC indicated reaction was completed. Bis-(dimethylamino)-methane (0.6 ml) was added slowly. The reaction was maintained at 25° C. for 12 h and concentrated, and the residue was purified by reverse phase preparative HPLC using a gradient of water and MeOH with 0.1% trifluoroacetic acid to afford 110 mg of FL-006.

1H NMR (300 MHz, DMSO-d6) 11.5-11.6 (bs, 1H), 9.7-9.9 (bs, 1H), 8.9-9.0 (s, 1H), 8.1-8.3 (m, 2H), 7.6-7.7 (d, 1H), 7.0-7.1 (d, 1H), 5.5-5.6 (s, 2H), 5.3-5.4 (s, 2H), 4.7-4.9 (s, 2H), 4.2-4.4 (m, 1H) 2.8-2.9 (s, 6H), 2.6-2.8 (m, 2H), 2.1-2.2 (m, 2H), 1.5-1.7 (m, 2H), 0.8-1.4 (m, 20H).

LCMS: 691.4 (M+1)⁺

Example 7

Synthesis of FL-007

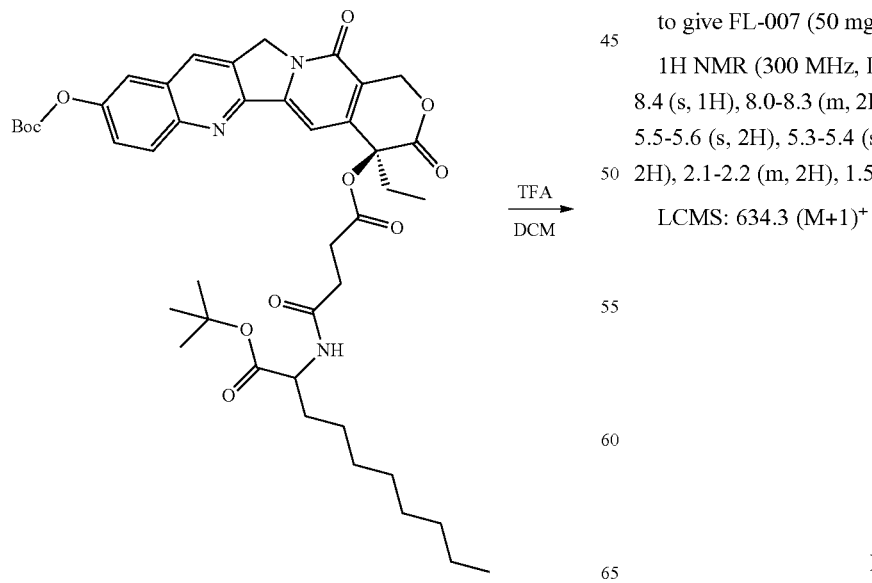

18

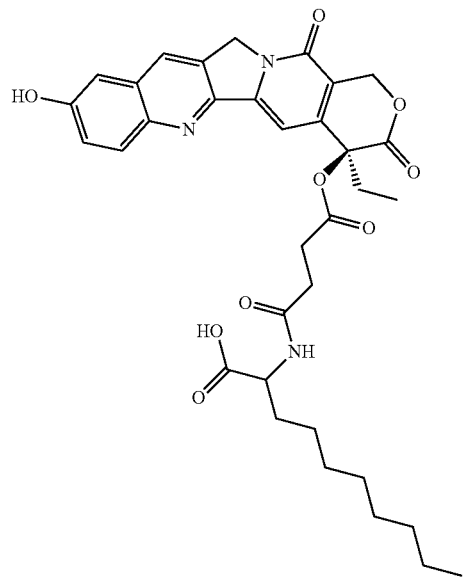

FL-007

1. Compound 18 (110 mg) was dissolved into 10 ml DCM, and TFA (0.9 ml) was added. The reaction was maintained at 25° C. for 12 h, and TLC indicated reaction was completed. The mixture was concentrated, and the residue was purified by flash chromatography using 5% MeOH/CHCl₃ to give FL-007 (50 mg) as a solid.

1H NMR (300 MHz, DMSO-d6) 10.2-10.3 (bs, 1H), 8.3-8.4 (s, 1H), 8.0-8.3 (m, 2H), 7.3-7.5 (m, 2H), 7.0-7.1 (d, 1H), 5.5-5.6 (s, 2H), 5.3-5.4 (s, 2H), 4.2-4.4 (m, 1H), 2.7-2.8 (m, 2H), 2.1-2.2 (m, 2H), 1.5-1.7 (m, 2H), 0.8-1.4 (m, 25H).

LCMS: 634.3 (M+1)⁺

Example 8

Synthesis of FL-008

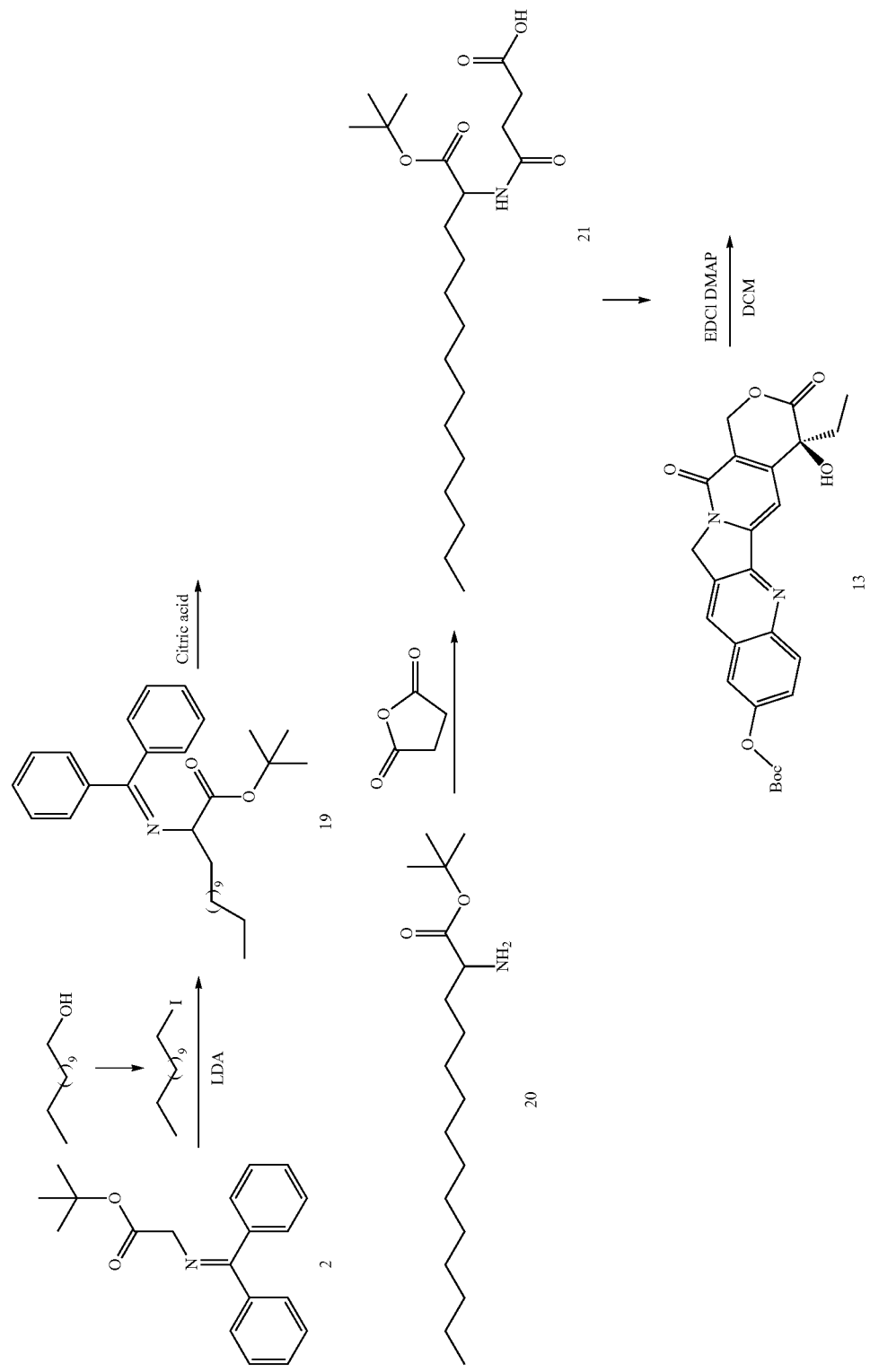

-continued
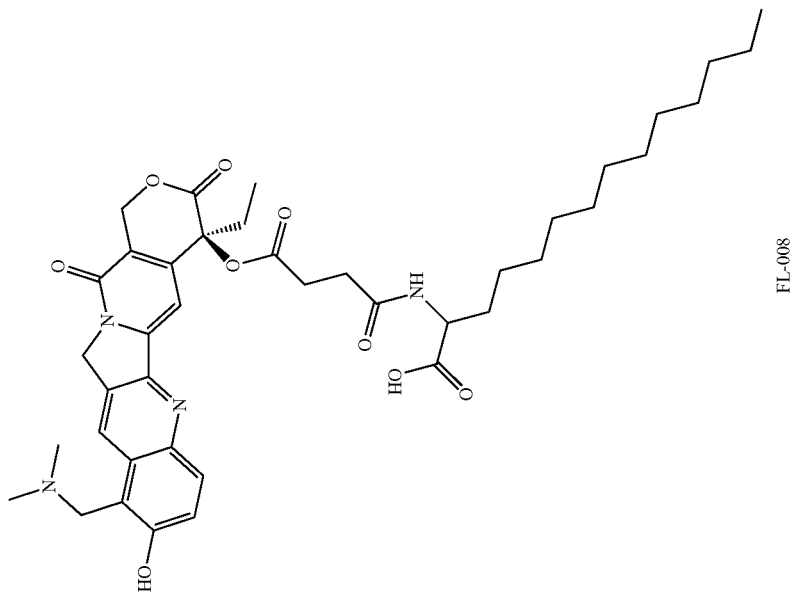
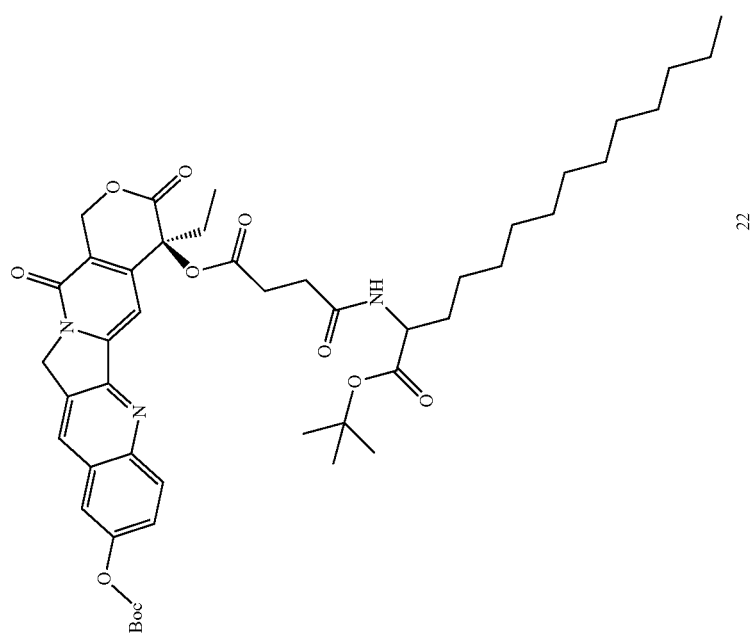

1. Compound 2 (32 g) in THF (150 ml) was added to LDA (2.2 eq) and kept at −78° C. in dry THF (150 ml) under nitrogen for 30 minutes. 1-Iodododecane (35 g) was added to the stirred mixture. After 2 h, the mixture was allowed to come slowly to room temperature and stirred overnight. The reaction was quenched by addition of water (100 ml) to the mixture at 0° C. This was then extracted with $CH_2Cl_2$ (200 ml*3). The product was purified by column on silica gel and recrystallized by 5% EA/PE to give compound 19 (18 g) as a white solid.

1H NMR (300 MHz, $CDCl_3$) 7.6-7.7 (m, 2H), 7.4-7.5 (m, 3H), 7.3-7.4 (m, 3H), 7.1-7.2 (m, 2H), 3.8-4.0 (m, 1H), 1.4-1.5 (s, 9H), 1.2-1.4 (m, 30H), 0.8-1.0 (m, 3H).

2. To a solution of compound 19 (18 g) in 200 ml of THF at RT was added 210 ml of 10% aq. citric acid, the mixture was stirred overnight. The reaction was quenched by addition of water (200 ml) to the mixture at 0° C. and adjust the pH value about 7 with $NaHCO_3$. The resultant mixture was extracted with $CH_2Cl_2$ (150 ml*3). Organic phase was washed with saturated solution of sodium chloride and dried over $Na_2SO_4$. The solvent was removed on vacuum to give a crude product, which was purified by column on silica gel and recrystallizated by 50% EA/PE to give compound 20 (9.5 g) as a white solid.

1H NMR (300 MHz, $CDCl_3$) 3.3-3.4 (1H), 1.4-1.5 (s, 9H), 1.2-1.4 (m, 30H), 0.8-1.0 (3H).

3. Compound 20 (3.5 g) was dissolved into 15 ml pyridine and cooled down in an ice bath. Dihydrofuran-2,5-dione (1.8 g) was added. The reaction was stirred at RT overnight. Volatiles were removed. The organic phase was separated and the aqueous phase was extracted with DCM, and washed with 2N HCl. The combined the organic phase was dried over $Na_2SO_4$ and concentrated to give compound 21 (3.1 g) as a white solid.

1H NMR (300 MHz, $CDCl_3$) 6.2-6.3 (bs, 1H), 4.4-4.5 (m, 1H), 2.7-2.8 (t, 2H), 2.5-2.6 (t, 2H), 1.8-1.9 (m, 1H), 1.4-1.5 (s, 9H), 1.2-1.4 (m, 29H), 0.8-0.9 (t, 3H).

4. Compound 21 (1.2 g) was dissolved into 15 ml DCM. EDCI (0.8 g), and DMAP (0.1 g) and compound 13 (0.4 g) were added. The reaction was maintained at 25° C. for 48 h, and TLC indicated reaction was completed. The organic phase was separated and the aqueous phase was extracted with DCM, and washed with $NaHCO_3$ (aq). The combined the organic phase was dried over $Na_2SO_4$ and concentrated, and the residue was purified by flash chromatography using 2% MeOH/$CHCl_3$ to give compound 22 (0.35 g) as a white solid.

1H NMR (300 MHz, $CDCl_3$) 8.4-8.5 (s, 1H), 8.2-8.3 (D, 1H), 7.9-8.0 (s, 1H), 7.6-7.7 (d, 1H), 7.2-7.3 (t, 1H), 6.0-6.2 (bs, 1H), 5.6-5.7 (s, 2H), 5.2-5.3 (s, 2H), 4.4-4.6 (m, 1H), 3.1-3.2 (t, 2H), 2.8-2.9 (t, 2H), 2.1-2.4 (m, 2H), 1.4-1.5 (s, 9H), 1.3-1.4 (s, 9H), 1.2-1.3 (m, 21H), 0.9-1.0 (t, 2H), 0.8-0.9 (m, 3H), 0.7-0.8 (m, 3H).

5. Compound 22 (0.2 g) was dissolved into 10 ml DCM, and TFA (1.5 ml) was added. The reaction was maintained at 25° C. for 12 h, and TLC indicated reaction was completed. Bis-(dimethylamino)-methane (0.5 ml) was added slowly. The reaction was maintained at 25° C. for 12 h, and concentrated. The residue was purified by reverse phase preparative HPLC to afford 105 mg of FL-008.

1H NMR (300 MHz, DMSO) 11.5-11.6 (bs, 1H), 9.8-10.0 (bs, 1H), 9.0-9.1 (s, 1H) 8.1-8.3 (m, 2H), 7.7-7.8 (d, 1H), 7.1-7.2 (s, 1H), 5.5-5.6 (s, 2H), 5.3-5.4 (s, 2H), 4.7-4.8 (s, 2H), 4.2-4.4 (m, 1H), 2.8-2.9 (s, 6H), 2.4-2.5 (t, 1H), 2.1-2.2 (m, 2H), 0.8-1.4 (m, 24H).

LCMS: 747.5 $(M+1)^+$

Example 9

Synthesis of FL-009

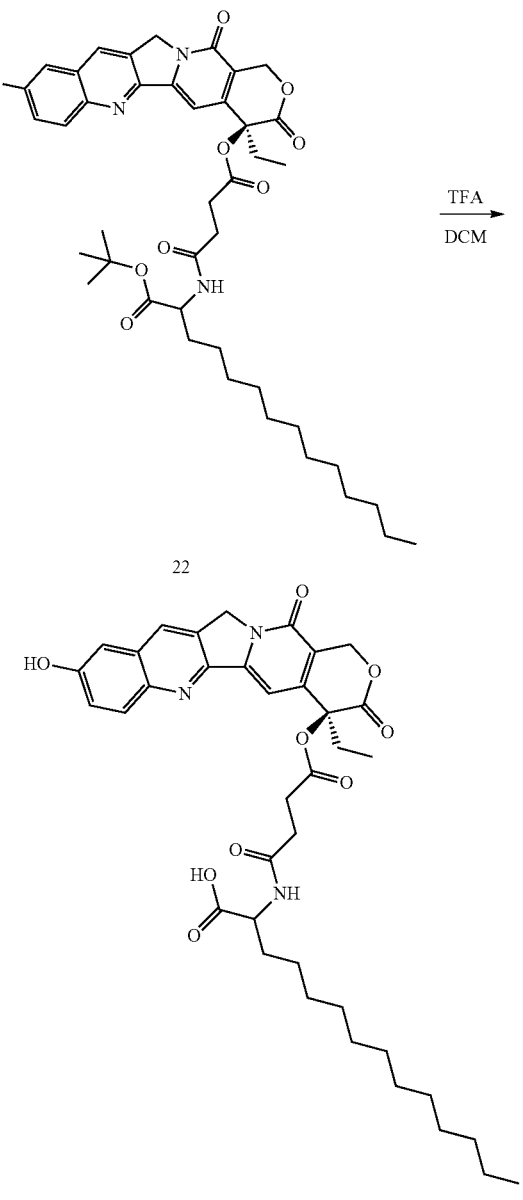

1. Compound 22 (0.15 g) was dissolved into 10 ml DCM, and TFA (1.5 ml) was added. The reaction was maintained at 25° C. for 12 h, and TLC indicated reaction was completed. The mixture was concentrated, and the residue was purified by flash chromatography using 5% MeOH/$CHCl_3$ to give FL-009 (102 mg) as a solid.

1H NMR (300 MHz, DMSO-d6) 10.2-10.5 (bs, 1H), 8.4-8.5 (s, 1H), 8.0-8.3 (m, 2H), 7.4-7.5 (d, 1H), 7.2-7.3 (s, 1H), 7.0-7.1 (d, 1H), 5.5-5.6 (s, 2H), 5.3-5.4 (s, 2H), 4.2-4.4 (m, 1H), 2.6-2.8 (m, 2H), 2.1-2.2 (m, 2H), 1.5-1.7 (m, 2H), 0.8-1.4 (m, 30H).

LCMS: 690.4 $(M+1)^+$

Example 10
Synthesis of FL-010
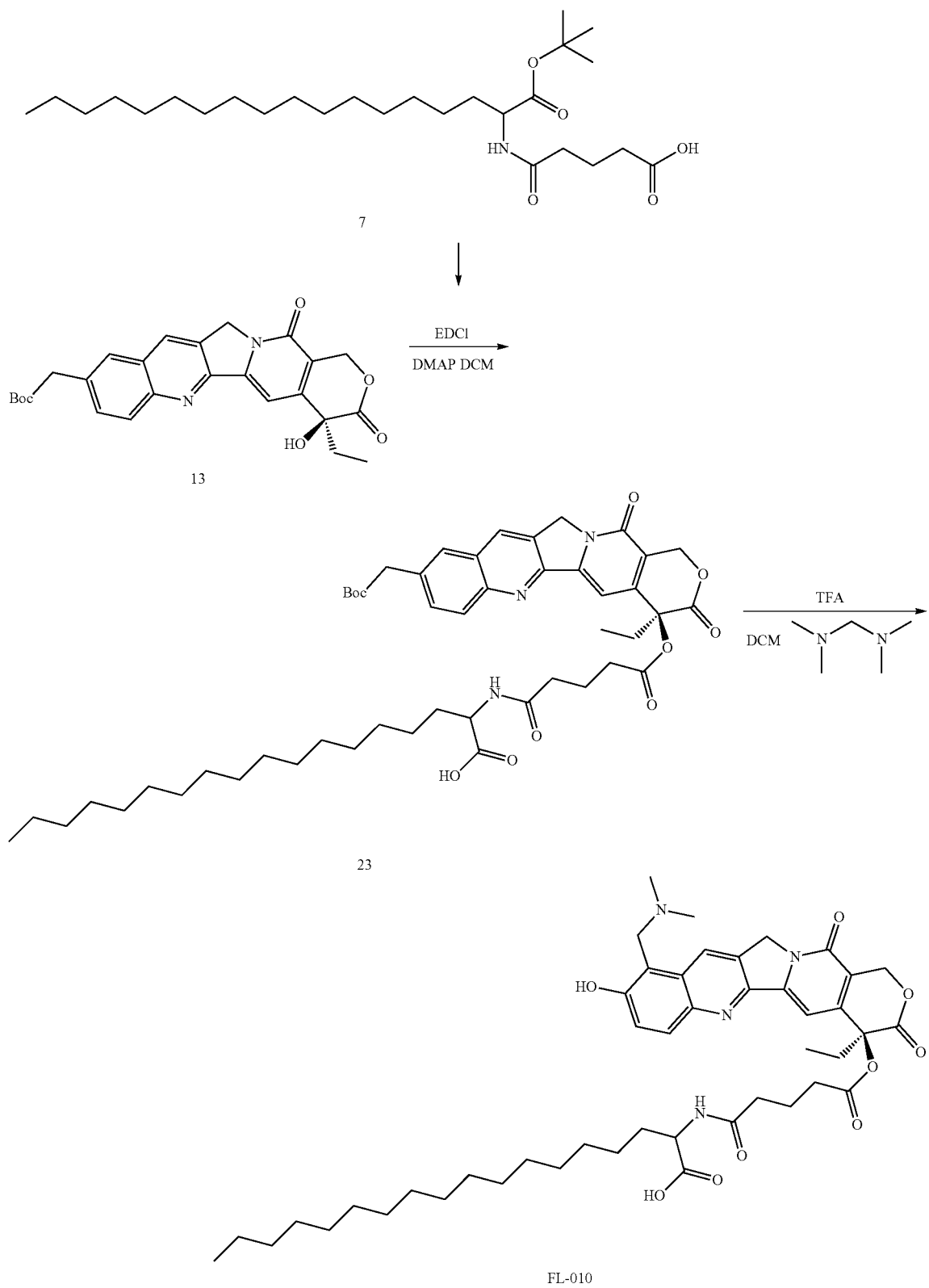

1. Compound 7 (2.3 g) was dissolved into 20 ml DCM, and EDCI (1.3 g), and DMAP (0.18 g) and compound 23 (0.8 g) were added. The reaction was maintained at 25° C. for 48 h, and TLC indicated reaction was completed. The organic phase was separated and the aqueous phase was extracted with DCM, and washed with NaHCO$_3$ (aq). The combined organic phase was dried over Na$_2$SO$_4$ and concentrated, and the residue was purified by flash chromatography using 2% MeOH/CHCl$_3$ to give compound 23 (0.75 g) as a white solid.

1H NMR (300 MHz, CDCl$_3$) 11.5-11.6 (bs, 1H), 9.8-10.0 (bs, 1H), 8.9-9.0 (s, 2H), 8.0-8.2 (m, 2H), 7.7-7.8 (m, 1H), 6.9-7.0 (s, 1H), 5.6-5.7 (s, 2H), 5.2-5.3 (d, 2H), 4.6-4.7 (s, 2H), 4.0-4.1 (m, 1H), 2.8-2.9 (t, 6H), 2.5-2.6 (t, 2H), 2.1-2.4 (m, 2H), 1.3-1.4 (m, 35H), 0.9-1.0 (t, 2H), 0.8-0.9 (m, 3H).

LCMS: 817.5 (M+1)$^+$

Example 11

Synthesis of FL-011

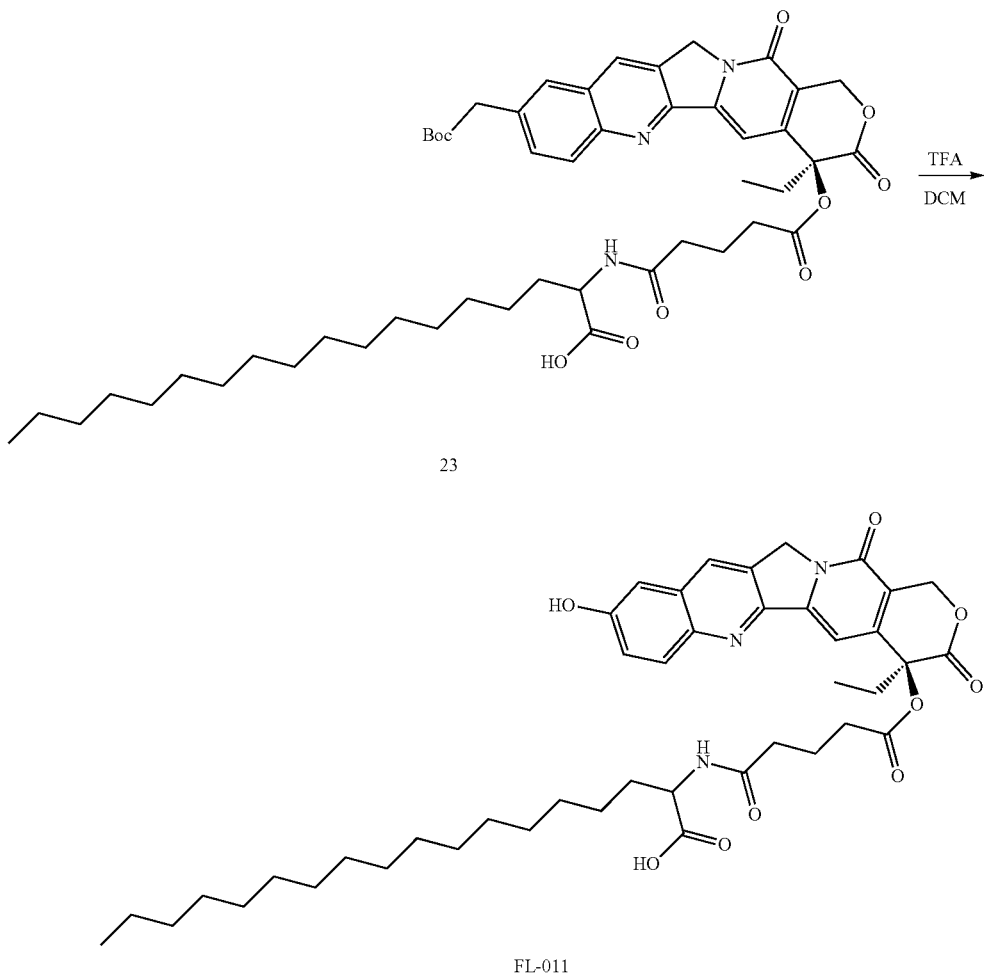

1H NMR (300 MHz, CDCl$_3$) 8.4-8.5 (s, 1H), 8.2-8.3 (D, 1H), 7.9-8.0 (s, 1H), 7.6-7.7 (d, 1H), 7.2-7.3 (t, 1H), 6.0-6.2 (bs, 1H), 5.6-5.7 (d, 1H), 5.3-5.5 (d, 1H), 5.2-5.3 (s, 2H), 4.4-4.6 (m, 1H), 3.1-3.2 (t, 2H), 2.8-2.9 (t, 2H), 2.5-2.6 (t, 2H), 2.1-2.4 (m, 2H), 1.4-1.5 (s, 9H), 1.3-1.4 (s, 9H), 1.2-1.3 (m, 33H), 0.9-1.0 (t, 2H), 0.8-0.9 (m, 3H), 0.7-0.8 (m, 3H).

2. Compound 23 (0.4 g) was dissolved into 10 ml DCM, and TFA (1.5 ml) was added. The reaction was maintained at 25° C. for 12 h, and TLC indicated reaction was completed. Bis-(dimethylamino)-methane (0.5 ml) was added slowly. The reaction was maintained at 25° C. for 12 h, and concentrated. The residue was purified by reverse phase preparative HPLC to afford 120 mg of FL-010.

1. Compound 23 (0.22 g) was dissolved into 10 ml DCM, and TFA (1.5 ml) was added. The reaction was maintained at 25° C. for 12 h, and TLC indicated reaction was completed. The mixture was concentrated, and the residue was purified by flash chromatography using 5% MeOH/CHCl$_3$ to give FL-011 (0.1 g) as a solid.

1H NMR (300 MHz, CDCl$_3$) 10.5-10.6 (bs, 1H), 9.5-9.6 (t, 1H), 8.0-8.2 (m, 1H), 7.3-7.5 (m, 2H), 6.9-7.0 (s, 1H), 5.6-5.7 (s, 2H), 5.2-5.3 (d, 2H), 4.0-4.1 (m, 1H), 2.1-2.4 (m, 4H), 1.8-1.9 (m, 2H), 1.3-1.4 (m, 28H), 0.9-1.0 (t, 2H), 0.8-0.9 (m, 3H).

LCMS: 760.4 (M+1)$^+$

Example 12

Synthesis of FL-012

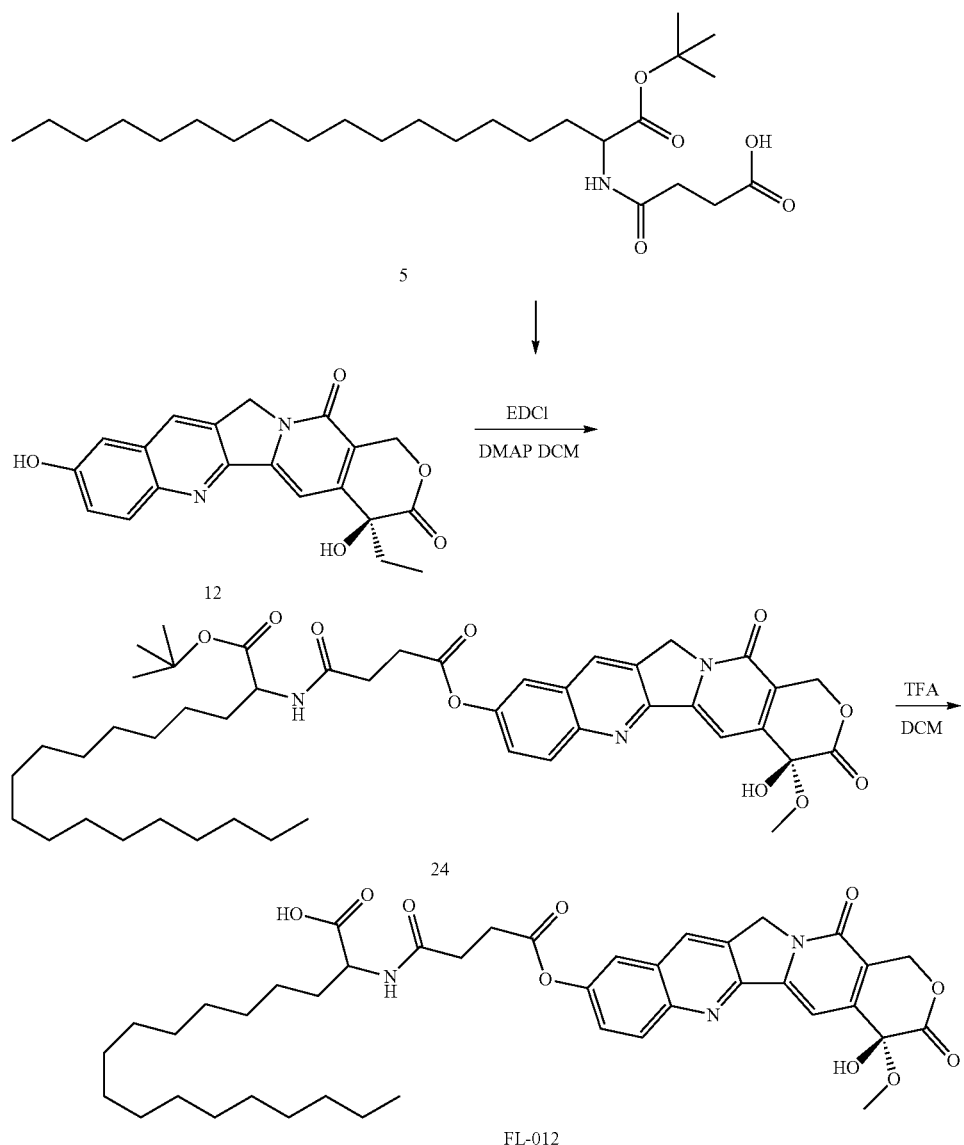

1. Compound 5 (0.8 g) was dissolved into 10 ml DMF, and EDCI (0.4 g), and DMAP (0.03 g) and compound 12 (0.4 g) were added. The reaction was maintained at 25° C. for 48 h, and TLC indicated reaction was completed. The organic phase was separated and the aqueous phase was extracted with DCM, and washed with NaHCO₃ (aq). The combined organic phase was dried over Na₂SO₄ and concentrated, and the residue was purified by flash chromatography using 2% MeOH/CHCl₃ to give compound 24 (0.4 g) as a white solid.

1H NMR (300 MHz, CDCl₃) 8.4-8.5 (s, 1H), 8.2-8.3 (t, 1H), 7.9-8.0 (t, 1H), 7.6-7.7 (t, 1H), 7.5-7.6 (t, 1H), 6.0-6.2 (bs, 1H), 5.7-5.8 (d, 1H), 5.3-5.4 (d, 3H), 5.2-5.3 (s, 2H), 4.4-4.6 (m, 1H), 2.7-2.8 (t, 2H), 2.5-2.6 (t, 2H), 2.1-2.4 (m, 2H), 1.4-1.5 (s, 9H), 1.3-1.4 (m, 33H), 0.9-1.0 (t, 2H), 0.8-0.9 (m, 3H).

2. Compound 24 (0.2 g) was dissolved into 10 ml DCM, and TFA (1.5 ml) was added. The reaction was maintained at 25° C. for 12 h, and TLC indicated reaction was completed. The mixture was concentrated, and the residue was purified by flash chromatography using 5% MeOH/CHCl₃ to give FL-012 (0.08 g) as a solid.

1H NMR (300 MHz, CDCl₃) 8.6-8.7 (s, 1H), 8.1-8.3 (d, 1H), 7.9-8.0 (s, 1H), 7.6-7.7 (d, 1H), 7 7.1-7.2 (s, 1H), 5.6-5.7 (s, 2H), 5.2-5.3 (d, 2H), 4.4-4.6 (m, 1H), 2.8-2.9 (t, 2H), 2.5-2.6 (t, 2H), 1.8-1.9 (m, 2H), 1.4-1.5 (m, 2H), 1.3-1.4 (m, 36H), 0.9-1.0 (t, 2H), 0.8-0.9 (m, 3H).

LCMS: 746.4 (M+1)⁺

Example 13
Synthesis of FL-013
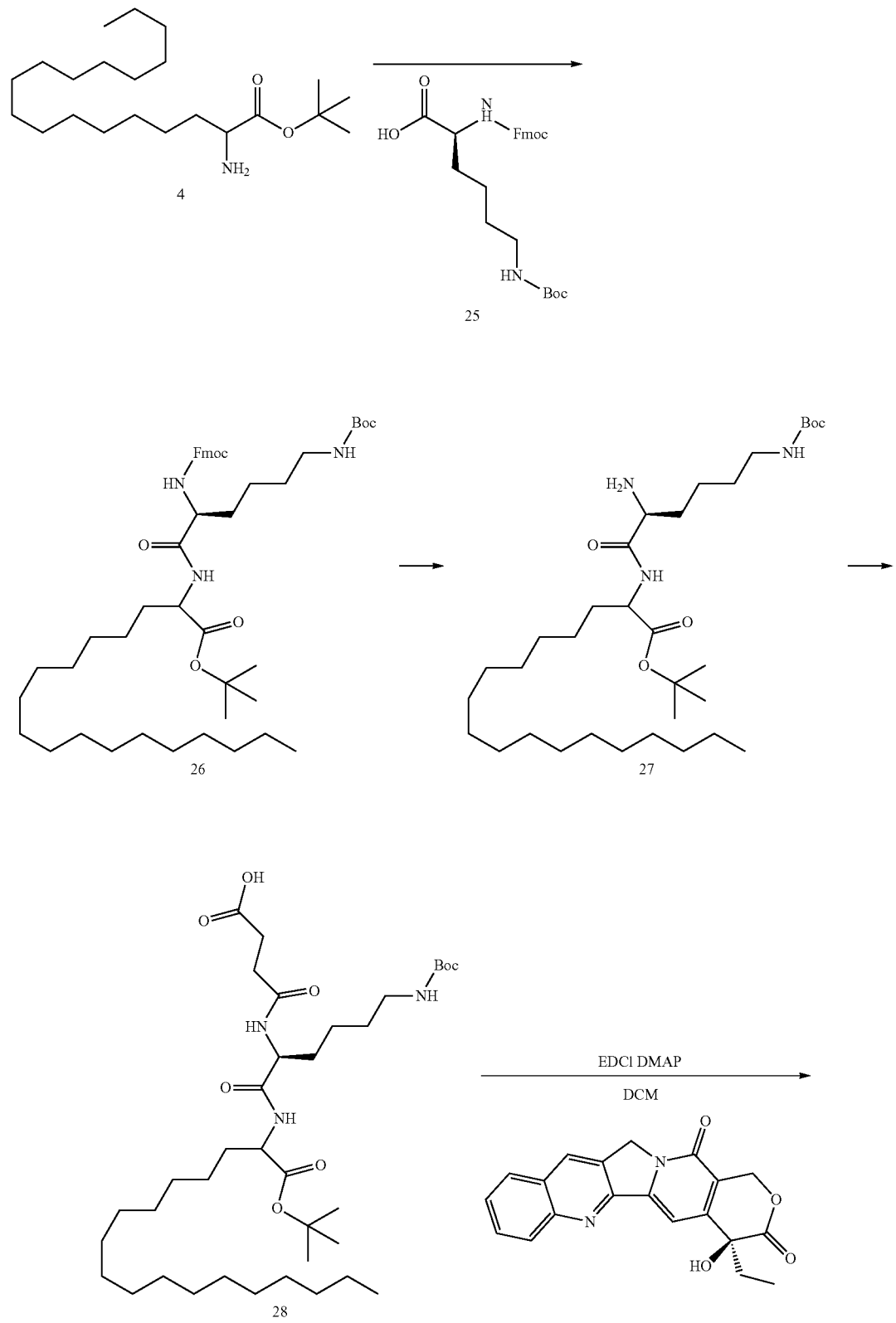

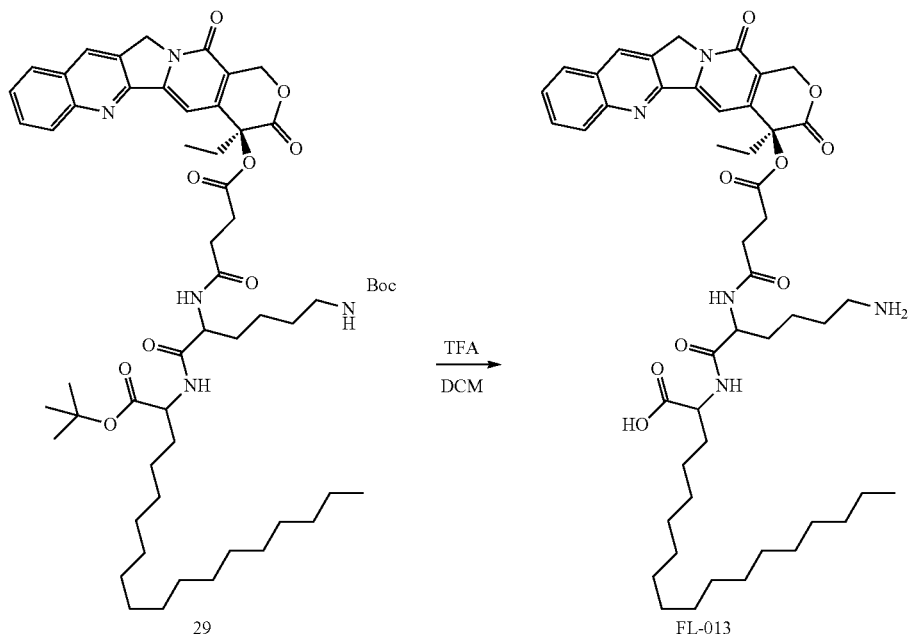 [SMILES: CCCCCCCCCCCCCCCCC(NC(=O)C(CCCCN)NC(=O)CCC(=O)O[C@]1(CC)C(=O)OCc2c1cc1n(c2=O)Cc2cc3ccccc3nc2-1)C(=O)OC(C)(C)C ; "Boc" ; CCCCCCCCCCCCCCCCC(NC(=O)C(CCCCN)NC(=O)CCC(=O)O[C@]1(CC)C(=O)OCc2c1cc1n(c2=O)Cc2cc3ccccc3nc2-1)C(=O)O]

1. Compound 4 (3.55 g) and Compound 25 (4.68 g) were dissolved in 30 ml DCM, and EDCI (2 eq) and DMAP (0.5 eq) were added. The reaction was maintained at 25° C. for 48 h, and TLC indicated reaction was completed. Water was added. The organic phase was separated and the aqueous phase was extracted with DCM, and washed with NaHCO$_3$ (aq). The combined organic phase was dried over Na$_2$SO$_4$ and concentrated, and the residue was purified by flash chromatography using 2% MeOH/CHCl$_3$ to give compound 26 (5.2 g) as a white solid.

1H NMR (300 MHz, CDCl$_3$) 7.8-7.9 (d, 2H), 7.5-7.6 (d, 2H), 7.3-7.4 (m, 4H), 4.5-4.6 (t, 2H), 4.2-4.3 (t, 1H), 1.4-1.5 (s, 18H), 1.3-1.4 (m, 33H).

2. Compound 26 (5.2 g) was dissolved in 50 ml DCM, and DBU (1 ml) was added. The reaction was maintained at 25° C. for 0.5 h, and TLC indicated reaction was completed. After the solvent was removed, the residue was purified by flash chromatography using EA/PE/Et$_3$N (50/50/1) to give compound 27 (3.3 g).

1H NMR (300 MHz, CDCl$_3$) 7.6-7.7 (bs, 1H), 4.6-4.7 (bs, 1H), 4.5-4.6 (t, 1H), 3.5-3.6 (bs, 1H), 1.4-1.5 (d, 18H), 1.2-1.4 (m, 33H).

3. Compound 27 (3.3 g) was dissolved in 30 ml pyridine and cooled down in an ice bath. Dihydrofuran-2,5-dione (1.9 g) was added. The reaction was stirred at RT overnight. Volatiles were removed. The organic phase was separated and the aqueous phase was extracted with DCM, and washed with 2N HCl. The combined organic phase was dried over Na$_2$SO$_4$ and concentrated to give compound 28 (3.15 g).

1H NMR (300 MHz, CDCl$_3$) 6.2-6.3 (bs, 1H), 4.4-4.5 (m, 1H), 2.7-2.8 (t, 2H), 2.5-2.6 (t, 2H), 1.4-1.5 (s, 18H), 1.2-1.4 (m, 33H).

4. Compound 28 (1 g) and camptothecin (0.25 g) were dissolved in 15 ml DCM, and EDCI (2 eq) and DMAP (0.5 eq) were added. The reaction was maintained at 25° C. for 48 h, and TLC indicated reaction was completed. The organic phase was separated and the aqueous phase was extracted with DCM, and washed with NaHCO$_3$ (aq) The combined organic phase was dried over Na$_2$SO$_4$ and concentrated, and the residue was purified by flash chromatography using 2% MeOH/CHCl$_3$ to give compound 29 (0.56 g).

1H NMR (300 MHz, CDCl$_3$) 8.4-8.5 (s, 1H), 8.2-8.3 (t, 1H), 7.9-8.0 (t, 1H), 7.8-7.9 (t, 1H), 7.6-7.7 (t, 1H), 7.3-7.4 (t, 1H), 6.0-6.2 (bs, 1H), 5.5-5.6 (s, 2H), 5.2-5.3 (s, 2H), 4.4-4.6 (m, 1H), 2.8-2.9 (t, 2H), 2.5-2.6 (t, 2H), 2.1-2.4 (m, 2H), 1.4-1.5 (d, 18H), 1.3-1.4 (m, 33H), 0.9-1.0 (t, 2H), 0.8-0.9 (m, 3H).

5. Compound 29 (0.15 g) was dissolved into 10 ml DCM, and TFA (1.5 ml) was added. The reaction was maintained at 25° C. for 12 h, and TLC indicated reaction was completed. The solution was concentrated, and the residue was purified by flash chromatography using 5% MeOH/CHCl$_3$ to give FL-013 (30 mg).

1H NMR (300 MHz, CDCl$_3$) 8.6-8.7 (s, 1H), 8.0-8.3 (m, 2H), 7.9-8.0 (t, 1H), 7.6-7.7 (t, 1H), 7.1-7.2 (d, 1H), 5.4-5.5 (s, 2H), 5.2-5.3 (s, 2H), 4.2-4.3 (m, 1H), 4.0-4.1 (m, 1H), 2.7-2.8 (m, 4H), 2.1-2.1 (m, 2H), 1.3-1.4 (m, 6H), 1.1-1.3 (m, 33H), 0.9-1.0 (t, 2H), 0.8-0.9 (m, 3H).

LCMS: 858.5 (M+1)$^+$

Example 14
Synthesis of FL-014
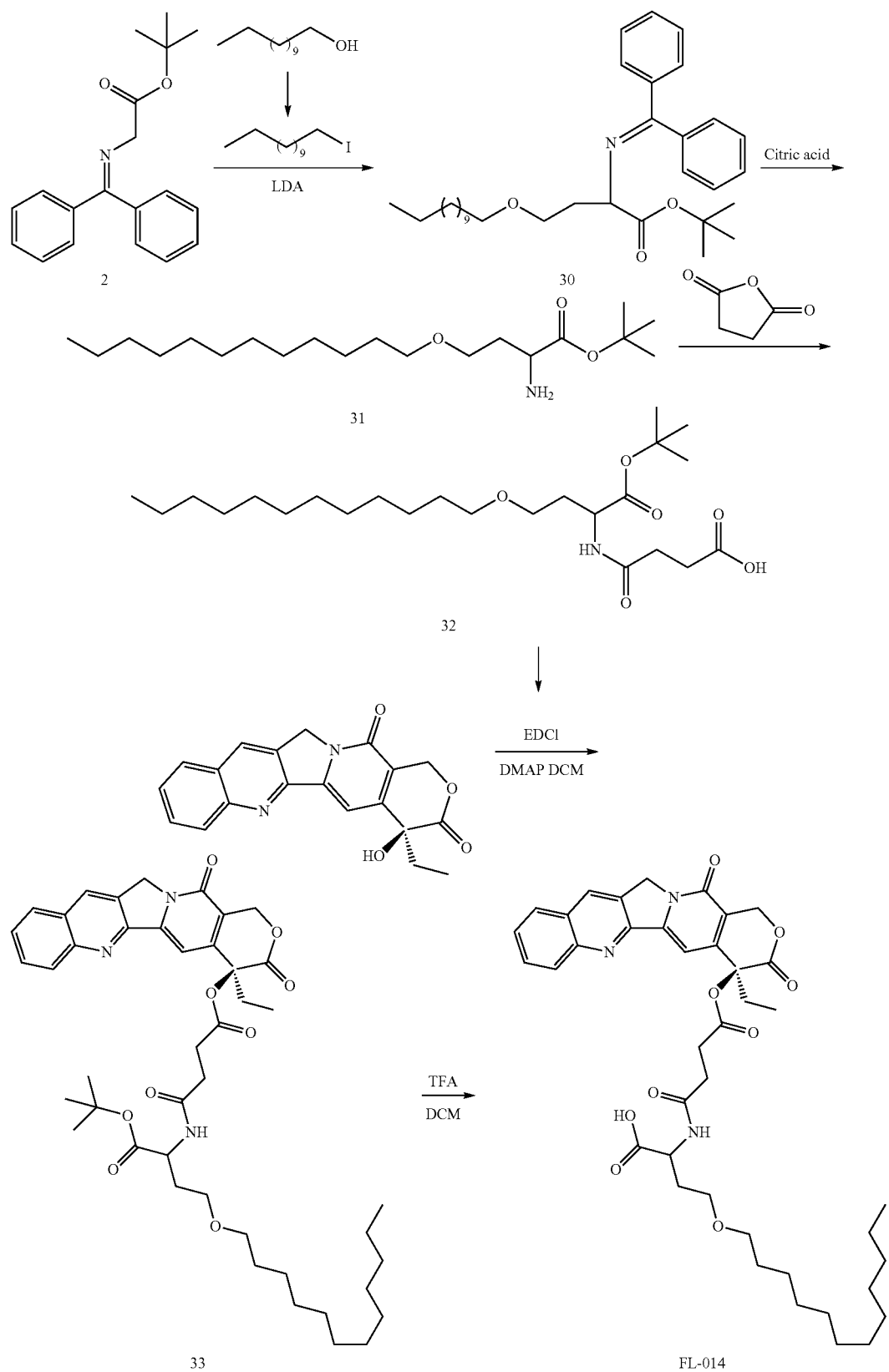

1. Compound 2 (29.6 g) in THF (150 ml) was added to LDA (2.2 eq) and kept at −78° C. in dry THF (150 ml) under nitrogen. After 30 min, 1-(2-iodoethoxy)-dodecane (33 g) was added to the stirred mixture. After 2 h, the mixture was allowed to come slowly to room temperature and stirred overnight. The reaction was quenched by addition of water (100 ml) to the mixture at 0° C. This was then extracted with $CH_2Cl_2$ (200 ml*3). The product was purity by column on silica gel and recrystallized by 5% EA/PE to give compound 30 (21 g) as a white solid.

1H NMR (300 MHz, $CDCl_3$) 7.6-7.7 (m, 2H), 7.4-7.5 (m, 3H), 7.3-7.4 (m, 3H), 7.1-7.2 (m, 2H), 3.8-4.0 (m, 1H), 1.4-1.5 (s, 9H), 1.2-1.4 (m, 30H), 0.8-1.0 (m, 3H).

2. To a solution of compound 30 (21 g) in 200 ml of THF at RT was added 210 ml of 10% aq. Citric acid, the mixture was stirred overnight. The reaction was quenched by addition of water (200 ml) at 0° C. and adjusted the pH value about 7 with $NaHCO_3$. The resultant mixture was extracted with $CH_2Cl_2$ (150 ml*3). Organic phase was washed with saturated solution of sodium chloride and dried over $Na_2SO_4$. The solvent was removed on vacuum to give a crude product, which was purified by column on silica gel and recrystallized by 50% EA/PE to give compound 31 (11 g).

1H NMR (300 MHz, $CDCl_3$) 3.3-3.4 (1H), 1.4-1.5 (s, 9H), 1.2-1.4 (m, 30H), 0.8-1.0 (3H).

3. Compound 31 (2 g) was dissolved in 15 ml pyridine and cooled down in an ice bath. Dihydrofuran-2,5-dione (1.5 g) was added. The reaction was stirred at RT overnight. Volatiles were removed. The organic phase was separated and the aqueous phase was extracted with DCM, and washed with 2N HCl. The combined organic phase was dried over $Na_2SO_4$ and concentrated to give compound 32 (1.8 g).

1H NMR (300 MHz, $CDCl_3$) 6.2-6.3 (bs, 1H), 4.4-4.5 (m, 1H), 2.7-2.8 (t, 2H), 2.5-2.6 (t, 2H), 1.8-1.9 (m, 1H), 1.4-1.5 (s, 9H), 1.2-1.4 (m, 29H), 0.8-0.9 (t, 3H).

4. Compound 32 (0.8 g) was dissolved into 15 ml DCM, and EDCI (0.5 g), and DMAP (10 mg) and camptothecin (0.35 g) were added. The reaction was maintained at 25° C. for 48 h, and TLC indicated reaction was completed. The organic phase was separated and the aqueous phase was extracted with DCM, and washed with $NaHCO_3$ (aq). The combined organic phase was dried over $Na_2SO_4$ and concentrated, and the residue was purified by flash chromatography using 2% $MeOH/CHCl_3$ to give compound 33 (0.32 g).

1H NMR (300 MHz, $CDCl_3$) 8.4-8.5 (s, 1H), 8.2-8.3 (t, 1H), 7.9-8.0 (t, 1H), 7.8-7.9 (t, 1H), 7.6-7.7 (t, 1H), 7.3-7.4 (t, 1H), 6.0-6.2 (bs, 1H), 5.6-5.7 (d, 2H), 5.2-5.3 (s, 2H), 4.4-4.6 (m, 1H), 2.8-2.9 (t, 2H), 2.5-2.6 (t, 2H), 2.1-2.4 (m, 2H), 1.4-1.5 (s, 9H), 1.3-1.4 (m, 33H), 0.9-1.0 (t, 2H), 0.8-0.9 (m, 3H).

5. Compound 33 (0.25 g) was dissolved into 30 ml DCM, and TFA (1.3 ml) were added. The reaction was maintained at 25° C. for 12 h, and TLC indicated reaction was completed. The solution was concentrated, and the residue was purified by flash chromatography using 5% $MeOH/CHCl_3$ to give FL-014 (110 mg).

1H NMR (300 MHz, $CDCl_3$) 8.7-8.8 (s, 1H), 8.0-8.3 (m, 3H), 7.9-8.0 (t, 1H), 7.8-7.9 (t, 2H), 7.1-7.3 (d, 1H), 5.6-5.7 (s, 2H), 5.2-5.3 (d, 2H), 4.4-4.6 (m, 1H), 2.8-2.9 (t, 2H), 2.1-2.2 (m, 2H), 1.5-1.7 (m, 2H), 1.2-1.4 (m, 28H) 0.9-1.0 (t, 2H), 0.8-0.9 (m, 3H).

LCMS: 718.4 (M+1)$^+$

Example 15

Synthesis of FL-015

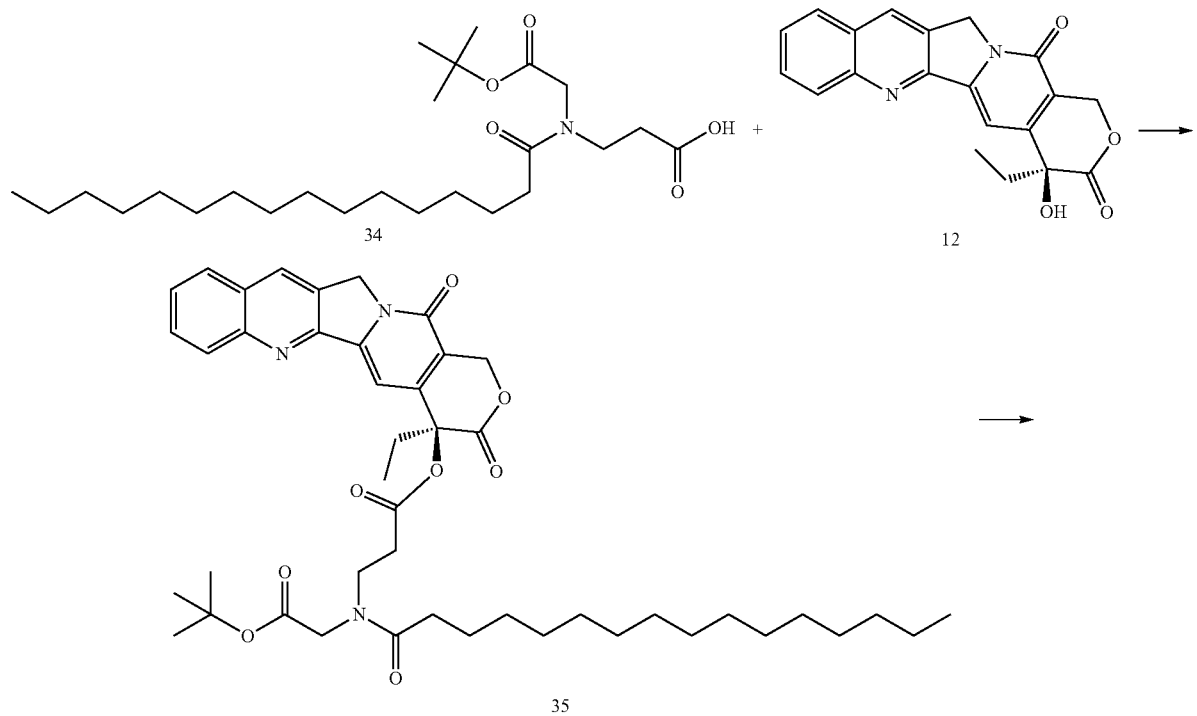

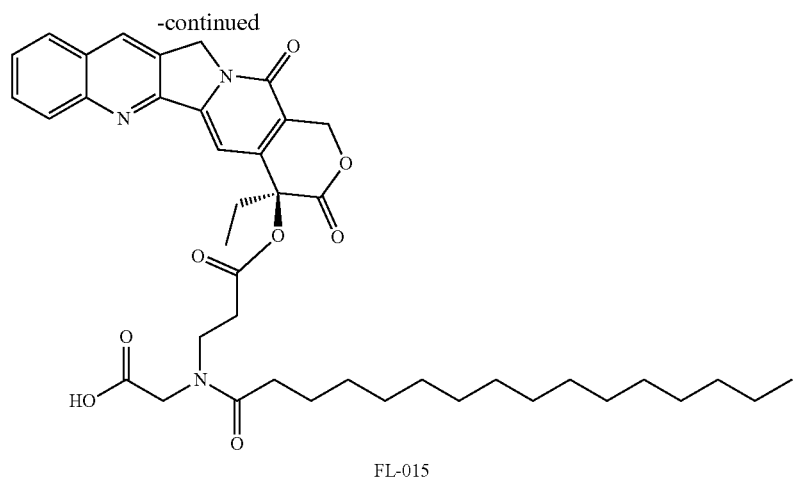

FL-015

1. Compound 12 (0.25 g) and compound 34 (0.63 g) were dissolved in 10 ml CH₂Cl₂. Then DMAP (44 mg) and EDCI (0.55 g) were added into the reaction mixture, and the mixture was stirred overnight. The reaction mixture was diluted by CHCl₃ and extracted by water and sat. NaHCO₃, and brine. The organic layer was evaporated to give a crude product, which was purified by silica gel column (1%-2% CH₃OH/CHCl₃) to give compound 35 (0.15 g).
2. Compound 35 (0.15 g) was dissolved in 10% TFA/CH₂Cl₂ (10 ml), and the mixture was stirred at RT overnight. The mixture was evaporated to give a crude product, which was purified by silica gel column (2%-5% CH₃OH/CHCl₃) to give FL-015 (80 mg).

1H NMR (300 MHz, DMSO-d6) δ: 8.6-8.7 (s, 1H), 8.1 (T, 2H), 7.9 (m, 1H), 7.7 (m, 1H), 7.0 (d, 1H), 5.5 (s, 1H), 4.0 (m, 2H), 2.7-2.9 (m, 2H), 2.0-2.3 (m, 5H), 1.4 (m, 2H), 1.0-1.3 (m, 28), 0.8-1.0 (m, 8H).

LC-MS: m/z=716.5[M+1]⁺

Example 16

Synthesis of FL-016

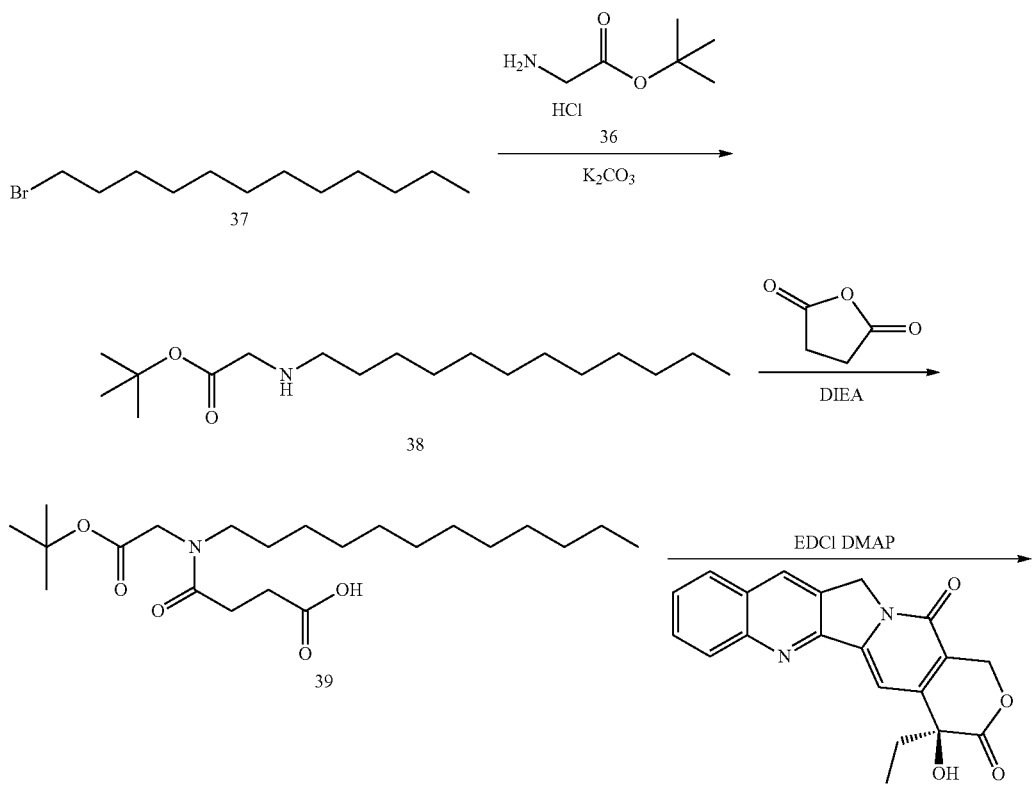

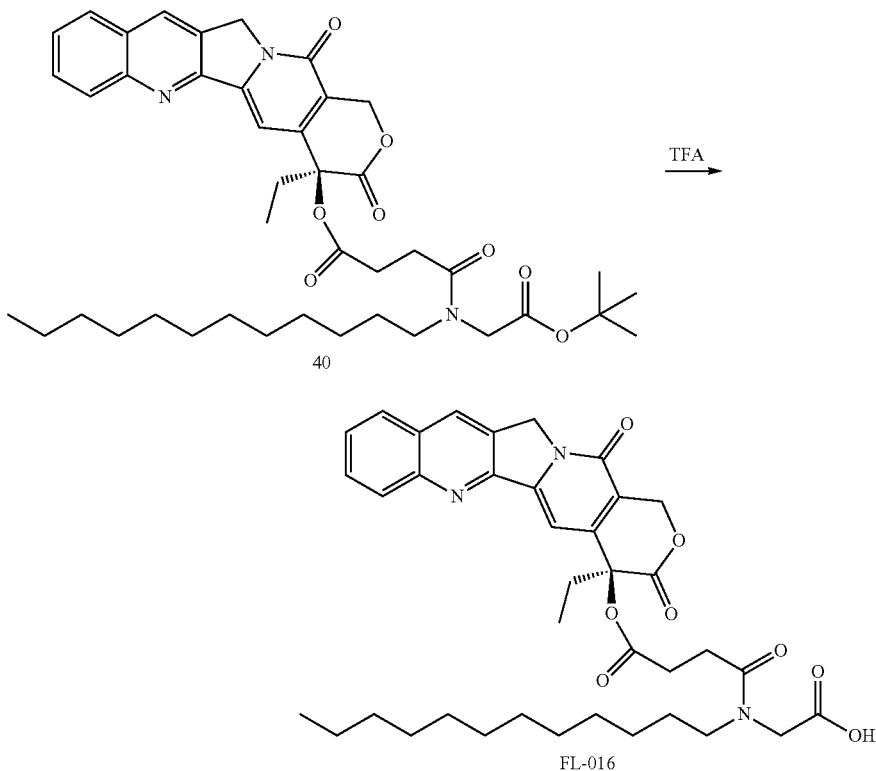

1. Compound 36 (5 g) and compound 37 (6 g) were dissolved in CH₃CN (150 ml) and THF (50 ml), followed by adding K₂CO₃ (5.4 g). The reaction mixture was stirred at RT for 3 hours, and then refluxed for 3 hours. The solvent was removed, and the residue was dissolved in water and extracted with EtOAc. The organic layer was dried and evaporated to give product 38 (6.3 g).
2. Compound 38 (6.3 g) was dissolved in DCM. DIEA (5.4 g) was added into the reaction mixture, followed by adding Dihydrofuran-2,5-dione (2.1 g) in portions. The reaction was stirred at RT for 2 hours. The reaction solution was washed by water twice and dried to give a crude product. The crude product was dissolved in 1N NaOH solution, and extracted by EtOAc. The water layer was adjusted to pH=4-5 using 2N HCl, and extracted by EtOAc. The combined organic layer was washed by water and brine, dried and evaporated to give compound 39 (1 g).
   1H NMR (CDCl₃, 300 MHz): 3.8-4.0 (m, 2H), 3.2 (m, 2H), 2.5-2.8 (m, 4H), 1.0-1.8 (m, 29H), 0.7-0.9 (m, 3H).
3. Compound 39 (0.7 g), camptothecin (0.3 g) and DMAP (53 mg) were dissolved in DCM. EDCI (0.66 g) was added into the reaction solution at RT, and then the mixture was stirred overnight. The reaction mixture was diluted by CHCl₃, washed by water and sat. NaHCO₃, dried, and evaporated to give a crude product, which was purified in silica gel column (1%-2% MeOH/CHCl₃) to give product 40 (0.2 g).
4. Compound 40 (0.2 g) was dissolved in DCM (15 ml), followed by adding TFA (2 ml) into the reaction. The mixture was stirred at RT overnight. The reaction solution was evaporated to give a crude product, which was purified in silica gel column (2%-5% MeOH/CHCl₃) to give FL-016 (45 mg).

1H NMR (300 MHz, DMSO-d6) δ: 8.7 (s, 1H), 8.0-8.3 (m, 2H), 7.7-7.9 (m, 2H), 7.1-7.3 (d, 1H), 5.5 (s, 2H), 5.2-5.3 (s, 2H), 4.1 (m, 3H), 2.5-2.7 (m, 5H), 2.0-2.2 (m, 2H), 0.8-1.6 (m, 39H).

LC-MS: m/z=674.0[M+1]⁺

Example 17

Synthesis of FL-018

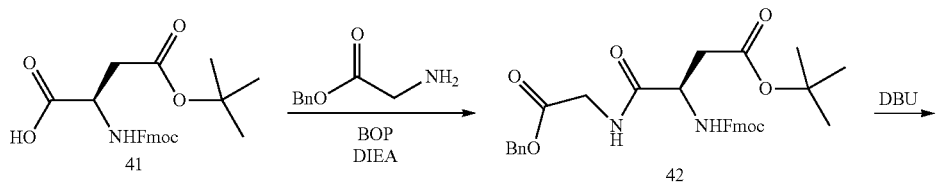

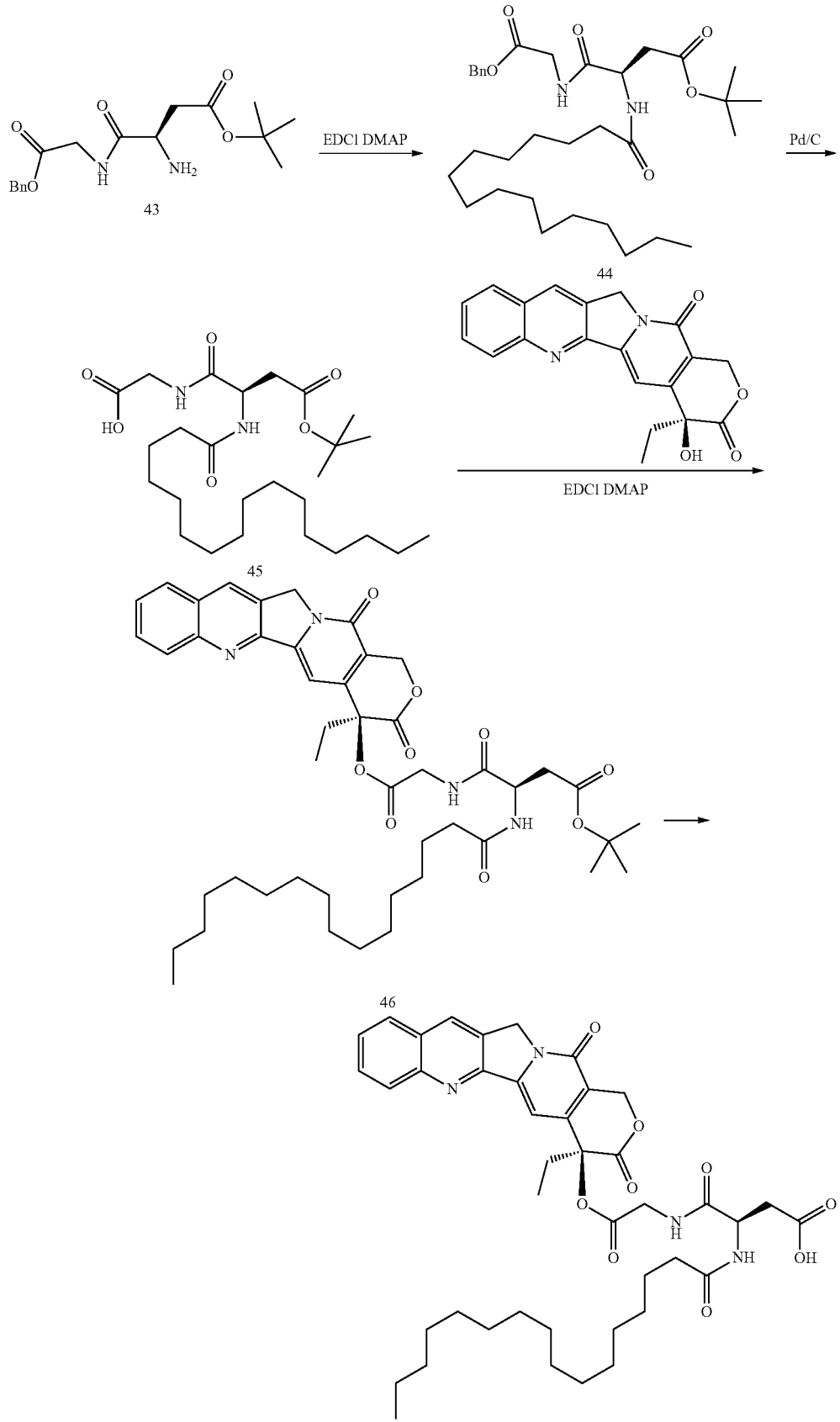

1. Compound 41 (5 g) and benzyl 2-aminoacetate (5 g) were dissolved in DMF, and reaction was cooled in an ice bath. DIEA (4.7 g) and BOP (7 g) were added, and the reaction was stirred at RT overnight. The reaction mixture was diluted with water and extracted with EtOAc. The organic layer was extracted with 1NHCl, sat. NaHCO$_3$, water and brine, dried, and evaporated to give compound 42 (6.2 g).
2. Compound 42 was dissolved in 5% DBU in DCM, and reaction solution was stirred at RT for 1 hour. The solvent was removed to give a crude product, which was purified in a silica gel column to give compound 43 (2.7 g).
3. Compound 43 (2.7 g) and palmitic acid (2.47 g) were dissolved in DCM, followed by DMAP (0.3 g) and EDCI (2.3 g). The reaction was stirred at RT overnight. The reaction solution was extracted with water and sat. NaHCO$_3$, dried, and evaporated to give compound 44 (3 g).
1H NMR (CDCl$_3$, 300 MHz): 7.2-7.4 (m, 5H), 5.1-5.2 (m, 2H), 4.8-5.0 (m, 1H), 3.9-4.2 (m, 2H), 2.7-2.8 (m, 1H), 2.6-2.7 (m, 1H), 2.1-2.3 (m, 2H), 1.6-1.7 (m, 2H), 1.4-1.5 (m, 9H), 1.1-1.4 (m, 26H), 0.7-0.9 (m, 3H).
4. Compound 44 (3 g) was dissolved in MeOH, and 10% Pd/C (0.3 g) was added into the reaction mixture. The reaction was hydrogenated at RT overnight. The reaction mixture was filtered, and filtrate was evaporated to a crude product, which was purified in a silica gel column to give compound 45 (1.6 g).

1HNMR (CDCl$_3$, 300 MHz): 4.8-5.0 (m, 1H), 3.9-4.2 (m, 2H), 2.7-2.8 (m, 1H), 2.6-2.7 (m, 1H), 2.1-2.3 (m, 2H), 1.6-1.7 (m, 2H), 1.4-1.5 (m, 9H), 1.1-1.4 (m, 26H), 0.7-0.9 (m, 3H).

5. Camptothecin (0.3 g) and compound 45 (0.83 g) were dissolved in DCM, followed by DMAP (53 mg) and EDCI (0.66 g). The reaction was stirred at RT overnight. The reaction mixture was diluted with CHCl$_3$, extracted with water and sat. NaHCO$_3$, dried, and evaporated to give a crude product, which was purified in a silica gel column (1%-2% MeOH/CHCl$_3$) to give compound 46 (0.2 g).
6. Compound 46 (0.2 g) was dissolved in 10 ml 5% TFA in DCM. The reaction was stirred at RT overnight. The solvent was removed to give a crude product, which was purified in a silica gel column (2%-5% MeOH/CHCl$_3$) to give FL-018 (40 mg).

1H NMR (300 MHz, DMSO-d6) δ: 8.7 (s, 1H), 8.3 (m, 1H), 7.1-7.2 (m, 2H), 8.1 (m, 2H), 7.8 (m, 1H), 7.6-7.7 (m, 1H), 7.1 (m, 1H), 5.5 (s, 2H), 5.2 (s, 2H), 4.6 (m, 1H), 4.0 (m, 2H), 2.0-2.1 (m, 6H), 1.1-1.4 (m, 50H), 0.8-0.9 (m, 10H).
LC-MS: m/z=759.6[M+1]$^+$

Example 18

Synthesis of FL-023

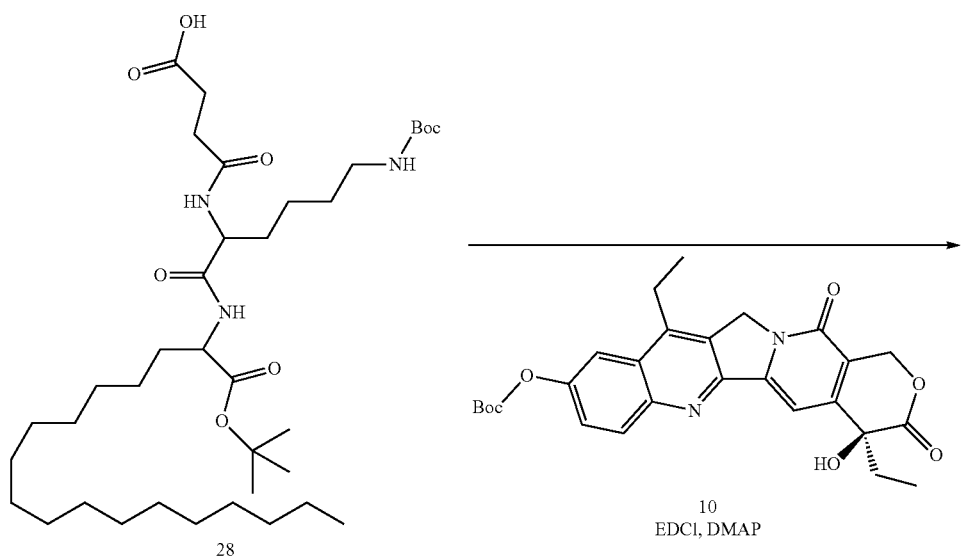

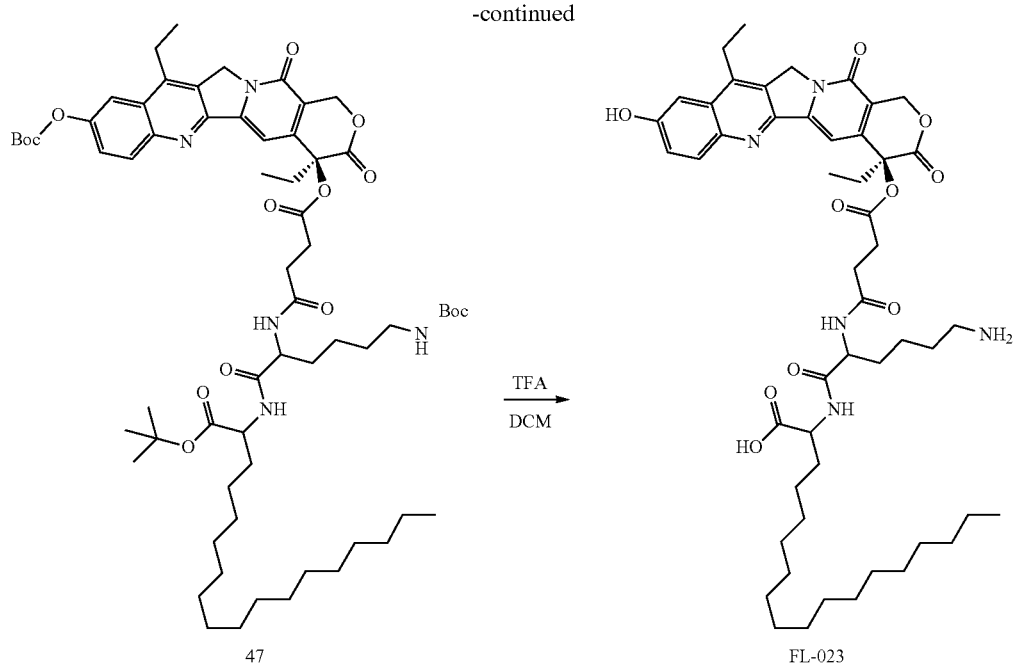

47 → FL-023

1. Compound 28 (1 g) and Compound 10 (0.25 g) were dissolved into 10 ml DCM, and then EDCI (0.35 g) and DMAP (30 mg) were added. The reaction was maintained at 25° C. for 48 h, and TLC indicated reaction was completed. The organic phase was separated and the aqueous phase was extracted with DCM, and washed with NaHCO₃ (aq). The combined organic phase was dried over Na₂SO₄ and concentrated, and the residue was purified by flash chromatography using 2% MeOH/CHCl₃ to give compound 47 (0.31 g).

1H NMR (300 MHz, CDCl₃) 7.9-8.0 (t, 1H), 7.8-7.9 (t, 1H), 7.6-7.7 (t, 1H), 7.3-7.4 (t, 1H), 6.0-6.2 (bs, 1H), 5.4-5.5 (s, 2H), 5.2-5.3 (s, 2H), 4.2-4.3 (m, 1H), 4.1-4.2 (m, 1H), 2.8-2.9 (t, 2H), 2.5-2.6 (t, 2H), 2.1-2.4 (m, 2H), 1.4-1.5 (d, 27H), 1.3-1.4 (m, 33H), 0.9-1.0 (t, 2H), 0.8-0.9 (m, 6H).

2. Compound 47 (0.15 g) was dissolved into 10 ml DCM, and TFA (1.6 ml) were added. The reaction was maintained at 25° C. for 12 h, and TLC indicated reaction was completed. The reaction mixture was concentrated, and the residue was purified by flash chromatography using 5% MeOH/CHCl₃ to give FL-023 (70 mg).

1H NMR (300 MHz, CDCl₃) 7.9-8.1 (t, 2H), 7.4-7.5 (t, 1H), 6.9-7.0 (d, 1H), 5.4-5.5 (s, 2H), 5.2-5.3 (s, 2H), 4.2-4.3 (m, 1H), 4.0-4.1 (m, 1H), 3.0-3.1 (m, 2H), 2.7-2.8 (m, 4H), 2.1-2.2 (m, 2H), 1.3-1.4 (m, 6H), 1.1-1.3 (m, 33H), 0.9-1.0 (t, 2H), 0.8-0.9 (m, 6H).

LCMS: 902.5 (M+1)⁺

Example 19

Synthesis of FL-024

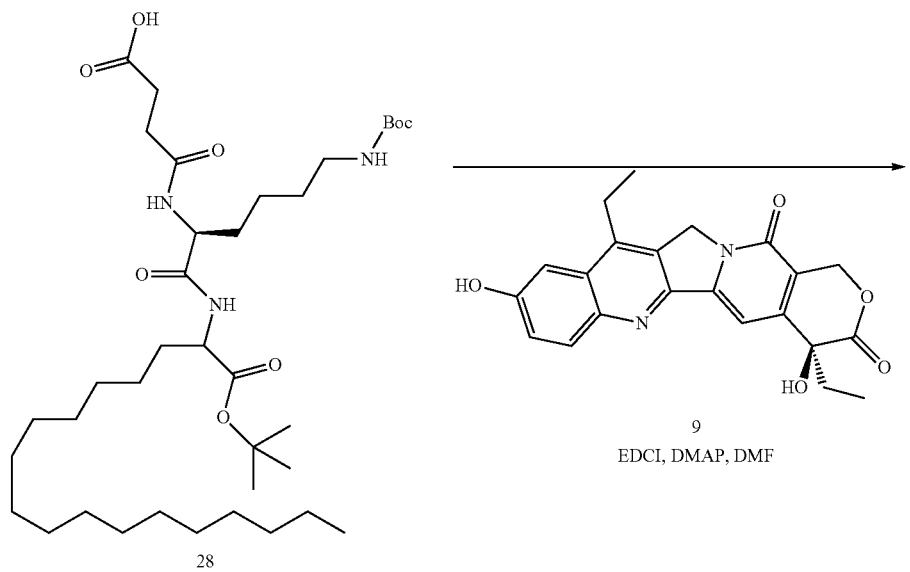

28 + 9, EDCI, DMAP, DMF

-continued

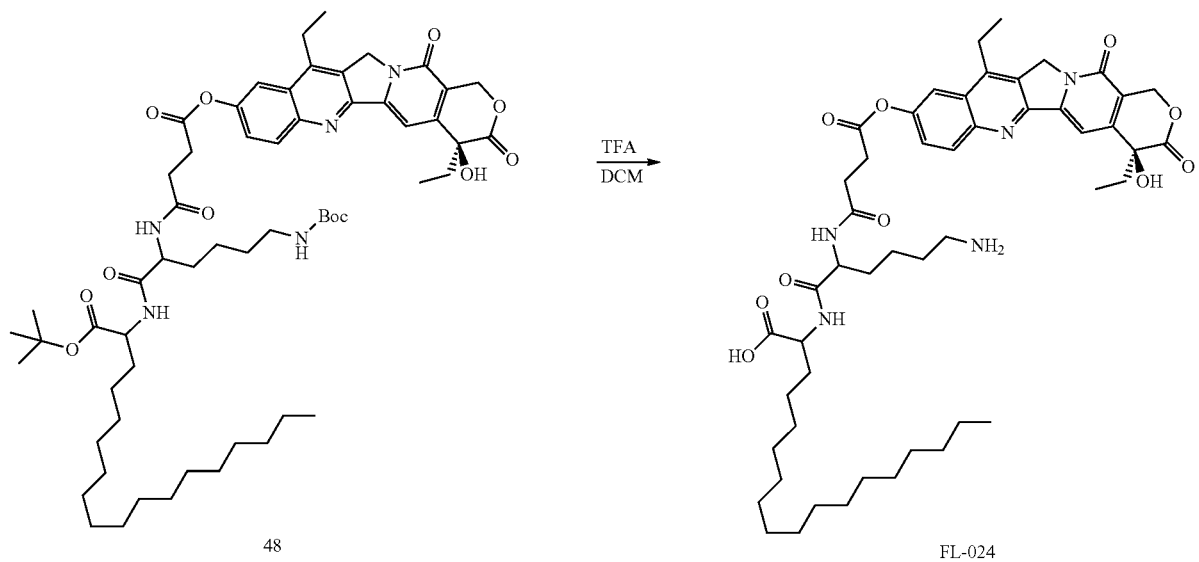

1. Compound 28 (2 g) and Compound 9 (0.5 g) were dissolved into 20 ml DMF, and then EDCI (0.76 g) and DMAP (60 mg) were added. The reaction was maintained at 25° C. for 48 h, and TLC indicated reaction was completed. The organic phase was separated and the aqueous phase was extracted with DCM, and washed with NaHCO$_3$ (aq). The combined the organic phase was dried over Na$_2$SO$_4$ and concentrated, and the residue was purified by flash chromatography using 2% MeOH/CHCl$_3$ to give compound 48 (0.75 g).

1H NMR (300 MHz, CDCl$_3$) 7.9-8.0 (t, 1H), 7.8-7.9 (t, 1H), 7.6-7.7 (t, 1H), 7.3-7.4 (t, 1H), 6.0-6.2 (bs, 1H), 5.6-5.7 (s, 2H), 5.4-5.5 (s, 2H), 5.2-5.3 (s, 2H), 4.2-4.3 (m, 1H), 4.1-4.2 (m, 1H), 2.8-2.9 (t, 2H), 2.5-2.6 (t, 2H), 2.1-2.4 (m, 2H), 1.4-1.5 (d, 18H), 1.3-1.4 (m, 33H), 0.9-1.0 (t, 2H), 0.8-0.9 (m, 6H).

2. Compound 48 (0.14 g) was dissolved into 10 ml DCM, and TFA (1.6 ml) was added. The reaction was maintained at 25° C. for 12 h, and TLC indicated reaction was completed. The solvent was removed, and the residue was purified by flash chromatography using 5% MeOH/CHCl$_3$ to give FL-24 (65 mg).

1H NMR (300 MHz, CDCl$_3$) 8.2-8.3 (t, 1H), 7.9-8.0 (s, 1H), 7.4-7.5 (d, 1H), 7.3-7.4 (s, 1H), 5.4-5.5 (s, 2H), 5.2-5.3 (s, 2H), 4.2-4.3 (m, 1H), 4.0-4.1 (m, 1H), 3.1-3.2 (m, 2H), 2.7-2.8 (m, 4H), 2.4-2.5 (m, 2H), 1.3-1.4 (m, 6H), 1.1-1.3 (m, 33H), 0.9-1.0 (t, 2H), 0.8-0.9 (m, 6H).

LCMS: 902.5 (M+1)$^+$

Example 20

Synthesis of FL-027

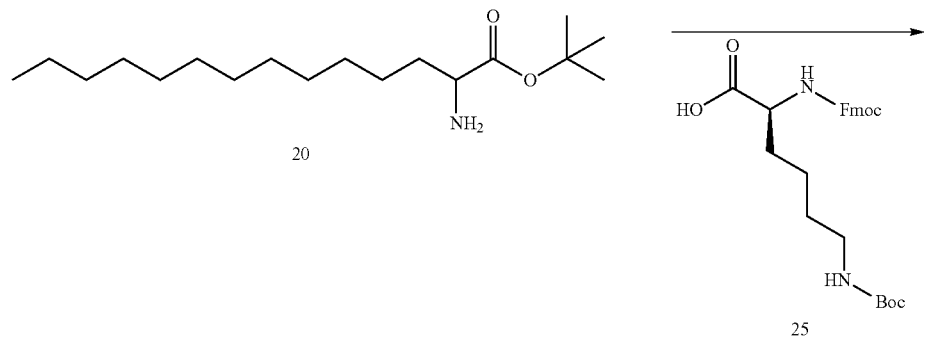

77 78
-continued
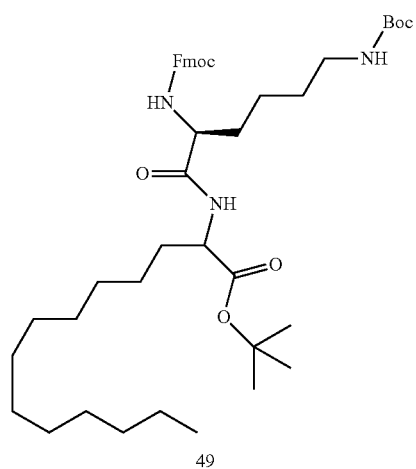
49
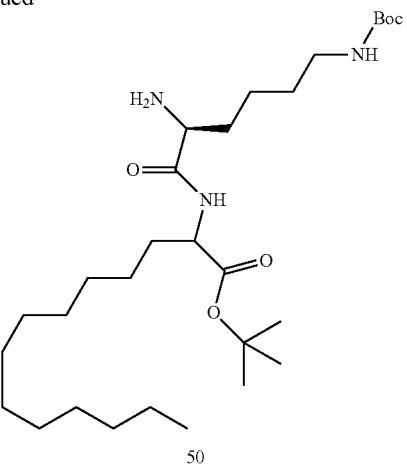
50
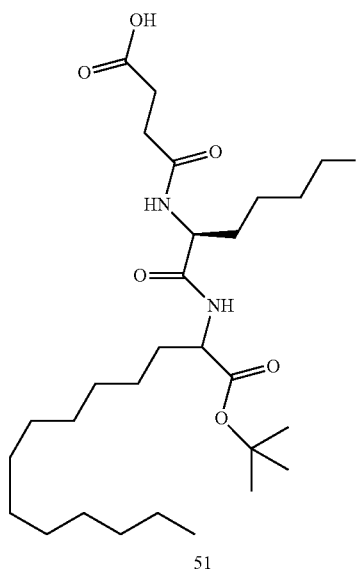
51
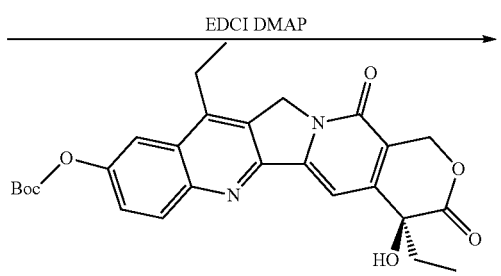
EDCI DMAP
10
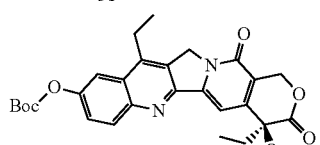
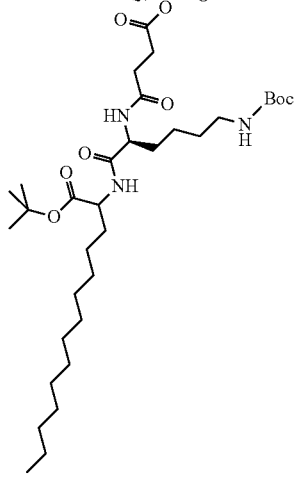
52
TFA
DCM
FL-027

1. Compound 20 (3.7 g) and Compound 25 (4.8 g) were dissolved into 30 ml DCM, and EDCI (3.82 g) and DMAP (62 mg) were added. The reaction was maintained at 25° C. overnight, and TLC indicated reaction was completed. The organic phase was separated and the aqueous phase was extracted with DCM, and washed with NaHCO$_3$ (aq). The combined the organic phase was dried over Na$_2$SO$_4$ and concentrated, and the residue was purified by flash chromatography to give compound 49 (5.8 g).

1H NMR (300 MHz, CDCl$_3$) 7.8-7.9 (d, 2H), 7.5-7.6 (d, 2H), 7.3-7.4 (m, 4H), 4.5-4.6 (t, 2H), 4.2-4.3 (t, 1H), 1.4-1.5 (s, 18H), 1.3-1.4 (m, 33H).

2. Compound 49 (5.8 g) was dissolved into 50 ml DCM, and DBU (1 ml) was added. The reaction was maintained at 25° C. for 0.5 h, and TLC indicated reaction was completed. The solvent was removed, and the residue was purified by flash chromatography using EA/PE/Et$_3$N (50/50/1) to give compound 50 (3.8 g).

1H NMR (300 MHz, CDCl$_3$) 7.6-7.7 (bs, 1H), 4.6-4.7 (bs, 1H), 4.5-4.6 (t, 1H), 3.5-3.6 (bs, 1H), 1.4-1.5 (d, 18H), 1.2-1.4 (m, 33H).

3. Compound 50 (3.8 g) was dissolved into 30 ml pyridine and cooled down in an ice bath. Dihydrofuran-2,5-dione (1.34 g) was added. The reaction was stirred at RT overnight. Volatiles were removed. The organic phase was separated and the aqueous phase was extracted with DCM, and washed with 2N HCl. The combined organic phase was dried over Na$_2$SO$_4$ and concentrated to give compound 51 (3.65 g).

1H NMR (300 MHz, CDCl$_3$) 6.2-6.3 (bs, 1H), 4.4-4.5 (m, 1H), 2.7-2.8 (t, 2H), 2.5-2.6 (t, 2H), 1.4-1.5 (s, 18H), 1.2-1.4 (m, 33H).

4. Compound 51 (1.5 g) and Compound 10 (0.35 g) were dissolved into 100 ml DCM, and EDCI (0.32 g) and DMAP (32 mg) were added. The reaction was maintained at 25° C. for 48 h, and TLC indicated reaction was completed. The organic phase was separated and the aqueous phase was extracted with DCM, and washed with NaHCO$_3$ (aq). The combined organic phase was dried over Na$_2$SO$_4$ and concentrated, and the residue was purified by flash chromatography using 2% MeOH/CHCl$_3$ to give compound 52 (0.46 g).

1H NMR (300 MHz, CDCl$_3$): 8.0-8.0 (t, 1H), 7.4-7.5 (t, 2H), 7.0-7.1 (t, 1H), 6.0-6.2 (bs, 1H), 5.4-5.5 (s, 2H), 5.2-5.3 (s, 2H), 4.2-4.3 (m, 1H), 4.1-4.2 (m, 1H), 2.8-2.9 (t, 2H), 2.5-2.6 (t, 2H), 2.1-2.4 (m, 2H), 1.4-1.5 (d, 27H), 1.3-1.4 (m, 25H), 0.9-1.0 (t, 2H), 0.8-0.9 (m, 6H).

5. Compound 52 (0.12 g) was dissolved into 10 ml DCM, and TFA (1.2 ml) was added. The reaction was maintained at 25° C. for 12 h, and TLC indicated reaction was completed. The solvent was removed, and the residue was purified by flash chromatography using 5% MeOH/CHCl$_3$ to give FL-027 (66 mg).

1H NMR (300 MHz, CDCl$_3$): 8.0-8.0 (t, 1H), 7.4-7.5 (t, 2H), 7.0-7.1 (t, 1H), 5.4-5.5 (s, 2H), 5.2-5.3 (s, 2H), 4.2-4.3 (m, 1H), 4.0-4.1 (m, 1H), 3.0-3.1 (m, 2H), 2.7-2.8 (m, 4H), 2.1-2.2 (m, 2H), 1.3-1.4 (m, 6H), 1.1-1.3 (m, 33H), 0.9-1.0 (t, 2H), 0.8-0.9 (m, 6H).

LCMS: 846.5 (M+1)$^+$

Example 21

Synthesis of FL-028

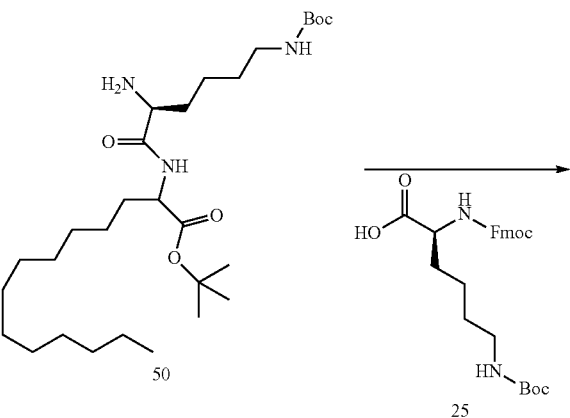

81
82
-continued
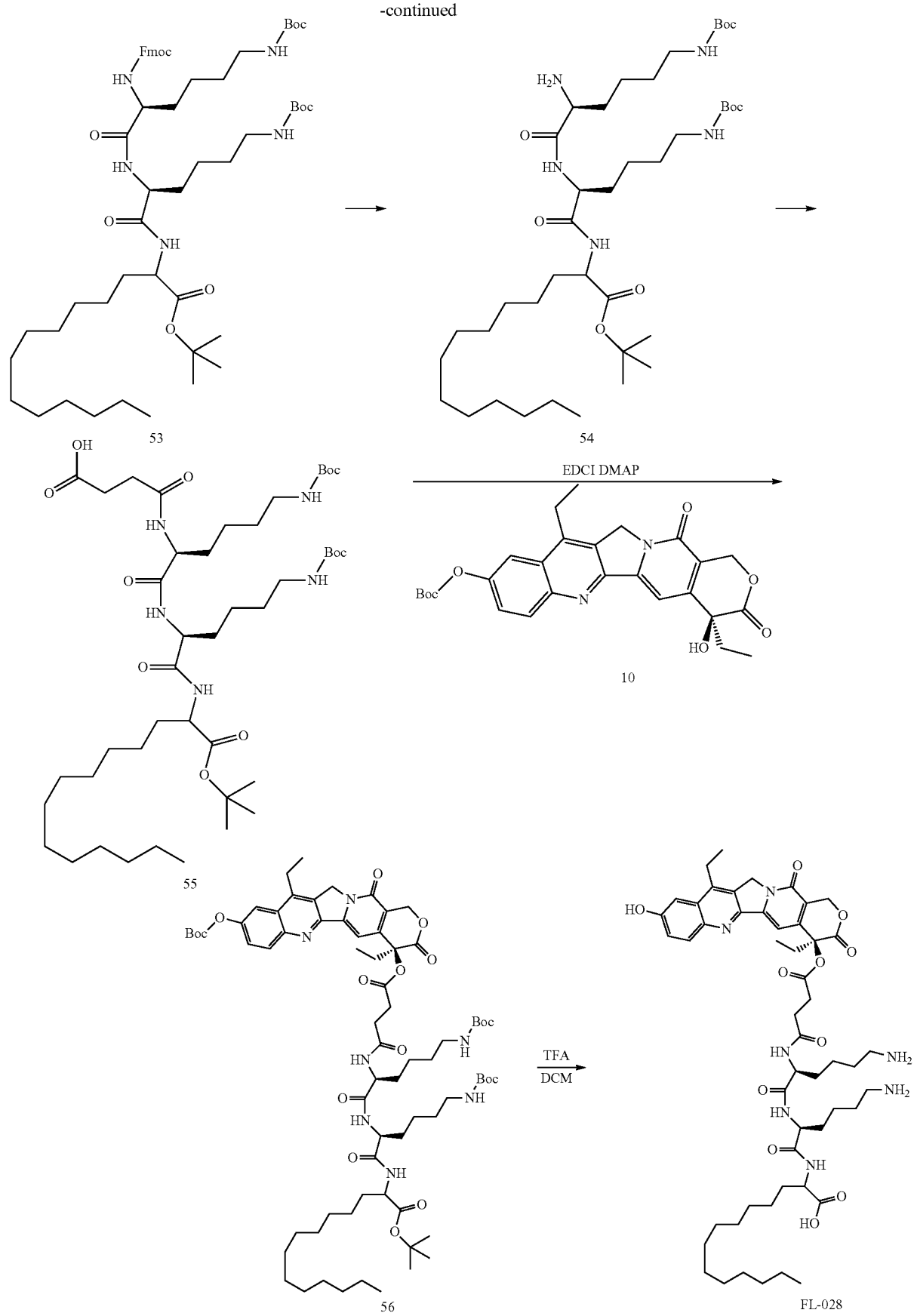

1. Compound 50 (4.36 g) and Compound 25 (5.6 g) was dissolved into 30 ml DCM, and EDCI (3.62 g) and DMAP (52 mg) was added. The reaction was maintained at 25° C. for 48 h, and TLC indicated reaction was completed. The organic phase was separated and the aqueous phase was extracted with DCM, and washed with NaHCO$_3$ (aq). The combined organic phase was dried over Na$_2$SO$_4$ and concentrated, and the residue was purified by flash chromatography to give compound 53 (5.43 g).

1H NMR (300 MHz, CDCl$_3$) 7.8-7.9 (d, 2H), 7.5-7.6 (d, 2H), 7.3-7.4 (m, 4H), 4.5-4.6 (t, 2H), 4.2-4.3 (t, 1H), 1.4-1.5 (s, 18H), 1.3-1.4 (m, 33H).

2. Compound 53 (5.43 g) was dissolved into 50 ml DCM, and DBU (1 ml) was added. The reaction was maintained at 25° C. for 0.5 h, and TLC indicated reaction was completed. The solvent was removed, and the residue was purified by flash chromatography using EA/PE/Et$_3$N (50/50/1) to give compound 54 (3.25 g).

3. Compound 54 (3.25 g) was dissolved into 30 ml pyridine and cooled down in an ice bath. Dihydrofuran-2,5-dione (1.12 g) was added. The reaction was stirred at RT overnight. Volatiles were removed. The organic phase was separated and the aqueous phase was extracted with DCM, and washed with 2N HCl. The combined organic phase was dried over Na$_2$SO$_4$ and concentrated to give compound 55 (3.05 g).

4. Compound 55 (1.2 g) and Compound 10 (0.31 g) were dissolved into 100 ml DCM, and EDCI (0.35 g) and DMAP (25 mg) were added. The reaction was maintained at 25° C. for 48 h, and TLC indicated reaction was completed. The organic phase was separated and the aqueous phase was extracted with DCM, and washed with NaHCO$_3$ (aq). The combined organic phase was dried over Na$_2$SO$_4$ and concentrated, and the residue was purified by flash chromatography using 2% MeOH/CHCl$_3$ to give compound 56 (0.31 g).

1H NMR (300 MHz, CDCl$_3$): 8.0-8.0 (t, 1H), 7.4-7.5 (t, 2H), 7.0-7.1 (t, 1H), 6.0-6.2 (bs, 1H), 5.4-5.5 (s, 2H), 5.2-5.3 (s, 2H), 4.2-4.3 (m, 2H), 4.1-4.2 (m, 1H), 2.8-2.9 (t, 2H), 2.5-2.6 (t, 4H), 2.1-2.4 (m, 4H), 1.4-1.5 (d, 36H), 1.3-1.4 (m, 25H), 1.2-1.3 (m, 12H) 0.9-1.0 (t, 2H), 0.8-0.9 (m, 6H).

5. Compound 56 (0.14 g) was dissolved into 10 ml DCM, and TFA (1.6 ml) was added. The reaction was maintained at 25° C. for 12 h, and TLC indicated reaction was completed. The solvent was removed, and the residue was purified by flash chromatography using 5% MeOH/CHCl$_3$ to give FL-028 (76 mg).

1H NMR (300 MHz, CDCl$_3$): 8.0-8.1 (t, 1H), 7.4-7.5 (t, 2H), 7.0-7.1 (t, 1H), 5.4-5.5 (s, 2H), 5.2-5.3 (s, 2H), 4.2-4.3 (m, 3H), 3.0-3.1 (m, 2H), 2.7-2.8 (m, 6H), 2.1-2.2 (m, 2H), 1.3-1.4 (m, 12H), 1.1-1.3 (m, 25H), 0.9-1.0 (t, 2H), 0.8-0.9 (m, 6H).

LCMS: 974.8 (M+1)$^+$

Example 22

Synthesis of FL-029

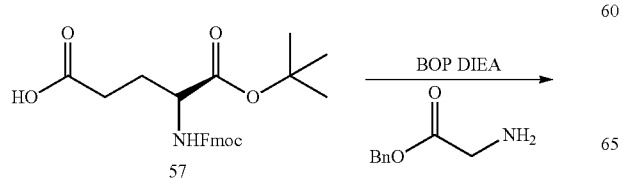

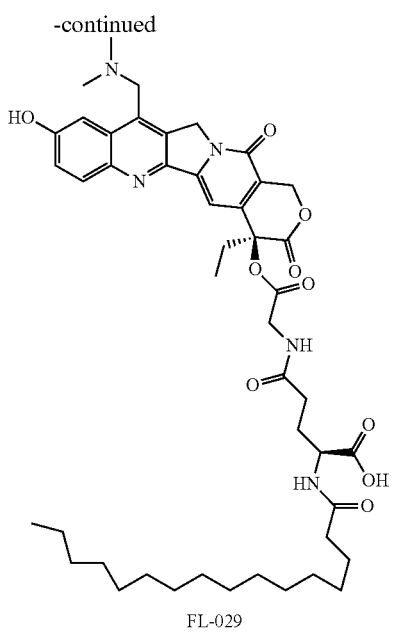

FL-029

1. Compound 57 (5 g) and benzyl 2-aminoacetate (2.33 g) were dissolved in DMF. DIEA (4.6 g) and BOP (6.8 g) were added into the reaction under an ice bath. The reaction was stirred at RT overnight. The reaction mixture was diluted with water and extracted with EtOAc. The organic layer was extracted with 1N HCl, sat. NaHCO₃, water and brine, dried, and evaporated to give compound 58 (6 g).

1H NMR (CDCl₃, 300 MHz): 7.7-7.8 (m, 2H), 7.6-7.7 (m, 2H), 7.1-7.5 (m, 9H), 6.5 (s, 1H), 5.5-5.6 (s, 1H), 5.0-5.2 (s, 2H), 4.3-4.5 (m, 2H), 4.0-4.3 (m, 4H), 2.0-2.3 (m, 3H), 1.8-2.0 (m, 1H), 1.3-1.5 (s, 9H).

2. Compound 58 (6 g) was dissolved in 5% DBU in DCM, and stirred at RT for 1 hour. The solvent was removed to give a crude product, which was purified in silica gel column to give compound 59 (2.5 g).

1HNMR (CDCl₃, 300 MHz): 7.1-7.5 (m, 9H), 5.0-5.2 (s, 2H), 4.0-4.3 (m, 3H), 2.0-2.3 (m, 3H), 1.8-2.0 (m, 1H), 1.3-1.5 (s, 9H).

3. Compound 59 (2.5 g) and palmitic acid (2.2 g) were dissolved in DCM, and DMAP (0.3 eq) and EDCI (1.5 eq) were added. The reaction was stirred at RT overnight. The reaction mixture was washed with water and sat. NaHCO₃, dried, and evaporated to give compound 60 (2.8 g).

1HNMR (CDCl₃, 300 MHz): 7.2-7.4 (m, 5H), 5.0-5.1 (s, 2H), 4.3-4.5 (m, 1H), 3.9-4.2 (m, 2H), 2.2-2.4 (m, 2H), 2.0-2.2 (m, 4H), 1.5-1.6 (m, 2H), 1.1-1.4 (m, 33H), 0.7-0.8 (m, 3H).

4. Compound 60 (2.8 g) was dissolved in MeOH, and 10% Pd/C (250 mg) was added. The reaction mixture was hydrogenated at RT overnight. The mixture was filtered, and the filtrate was evaporated to give a crude product, which was purified with a silica gel column to give compound 61 (1.4 g).

1HNMR (CDCl₃, 300 MHz): 4.3-4.5 (m, 1H), 3.9-4.2 (m, 2H), 2.2-2.4 (m, 2H), 2.0-2.2 (m, 4H), 1.5-1.6 (m, 2H), 1.1-1.4 (m, 33H), 0.7-0.8 (m, 3H).

5. Compound 61 (0.3 g) and compound 13 (0.65 g) were dissolved in DCM, and DMAP (40 mg) and EDCI (0.5 g) were added. The reaction was stirred at RT overnight. The reaction was diluted with CHCl₃, washed with water and sat. NaHCO₃, dried, and evaporated to give a crude product, which was purified by a silica gel column to give compound 62 (0.18 g).

6. Compound 62 (0.18 g) was dissolved in 10% TFA in DCM (10 ml). The reaction was stirred at RT overnight. Then N,N,N',N'-tetramethylmethanediamine (0.39 g) was added into the reaction mixture. The reaction was stirred overnight. The solvent was removed to give a crude product, which was purified using Prep HPLC to give FL-029 (50 mg).

1H NMR (300 MHz, DMSO-d6) δ: 11.6 (s, 1H), 9.8 (s, 1H), 9.0 (s, 1H), 8.4 (s, 1H), 8.0-8.2 (d, 2H), 7.7 (s, 1H), 7.0-7.1 (s, 1H), 5.5 (s, 2H), 5.3 (s, 2H), 4.7 (s, 3H), 2.8 (s, 6H), 2.0-2.2 (m, 6H), 1.0-1.5 (m, 28H), 0.8-1.0 (d, 6H).

LC-MS: m/z=846.7[M+1]⁺

Example 23

Synthesis of FL-033

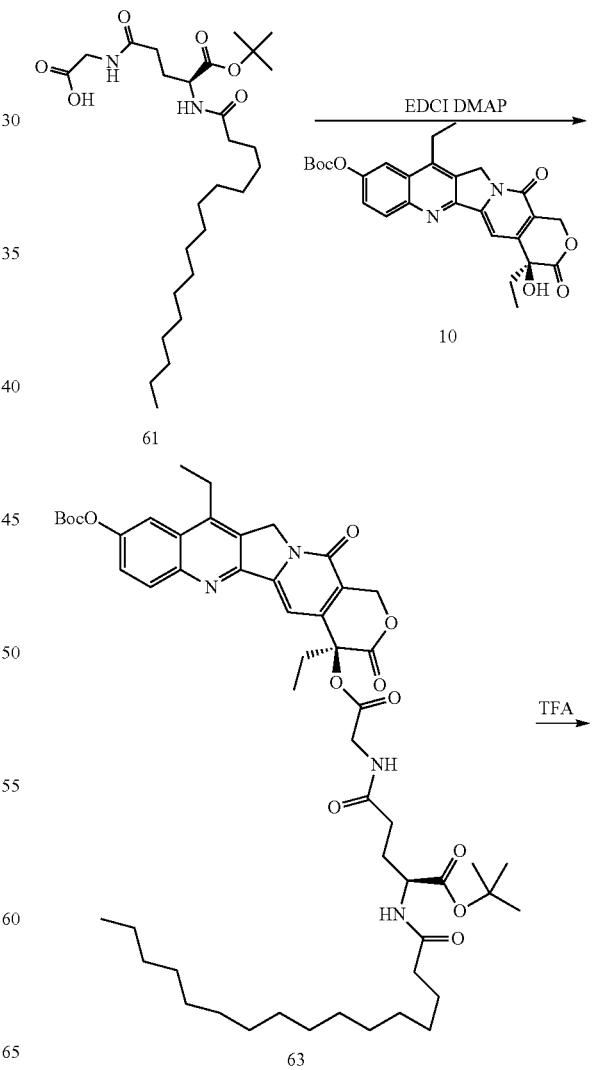

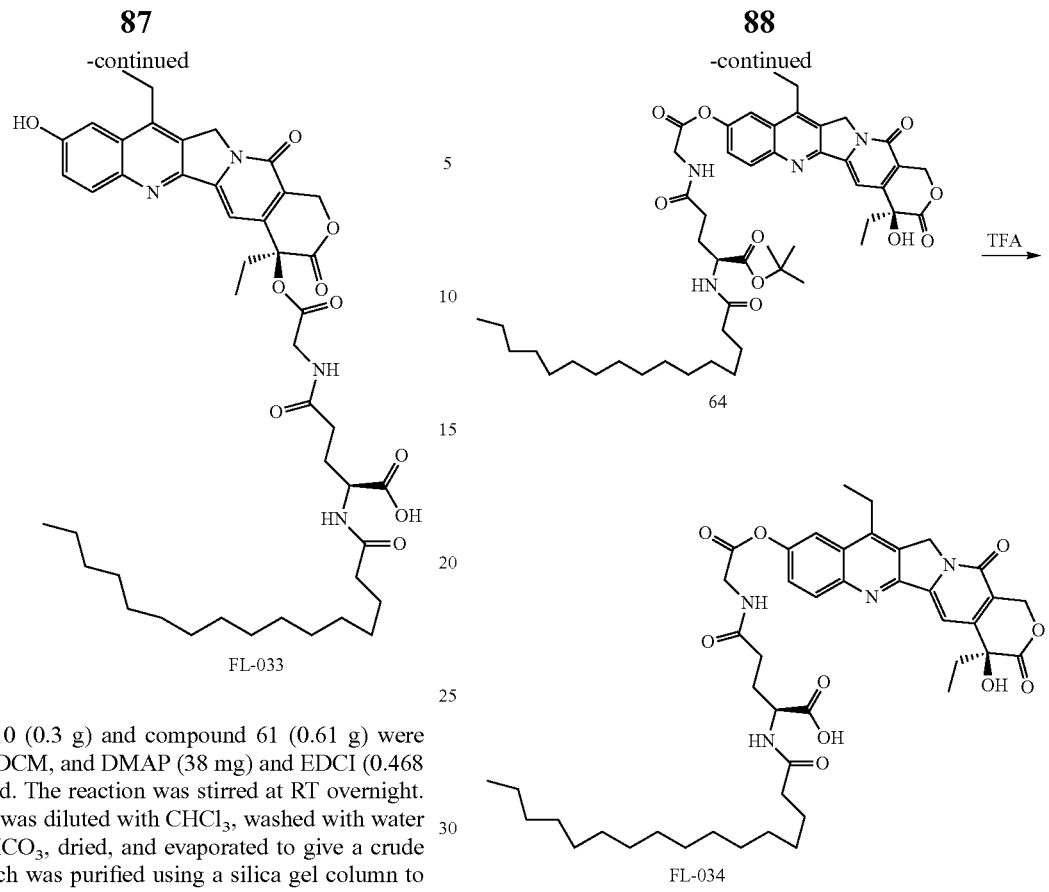

FL-033

1. Compound 10 (0.3 g) and compound 61 (0.61 g) were dissolved in DCM, and DMAP (38 mg) and EDCI (0.468 g) were added. The reaction was stirred at RT overnight. The reaction was diluted with CHCl₃, washed with water and sat. NaHCO₃, dried, and evaporated to give a crude product, which was purified using a silica gel column to give compound 63 (0.15 g).
2. Compound 63 (0.15 g) was dissolved in 10% TFA in DCM (10 ml). The reaction was stirred overnight. The solvent was removed to give a crude product, which was purified using a silica gel column to give FL-033 (80 mg).
   1H NMR (300 MHz, DMSO-d6) δ: 8.0 (t, 2H), 7.3-7.4 (m, 2H), 7.0 (s, 1H), 5.4-5.5 (s, 2H), 5.2 (d, 2H), 4.1 (m, 2H), 3.9-4.0 (m, 1H), 3.0-3.1 (m, 3H), 2.1-2.2 (m, 7H), 2.0-2.1 (m, 2H), 1.9 (m, 1H), 1.7 (s, 1H), 1.1-1.4 (m, 50H), 0.8-0.9 (m, 10H).
   LC-MS: m/z=839.6[M+Na]⁺

Example 24

Synthesis of FL-034

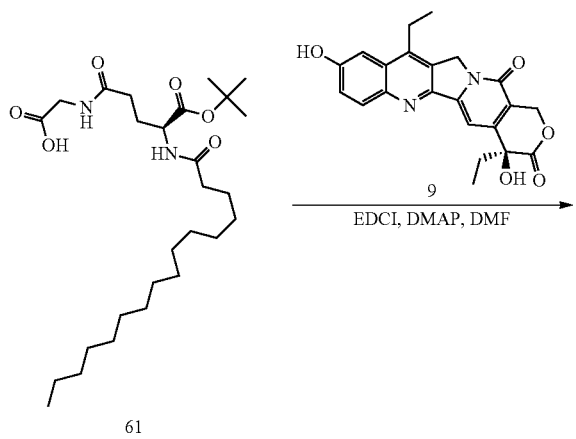

FL-034

1. Compound 61 (0.88 g) was dissolved into 35 ml DMF, and EDCI (0.383 g), and DMAP (63 mg) and compound 9 (0.4 g) were added. The reaction was maintained at 25° C. for 48 h, and TLC indicated reaction was completed. The organic phase was separated and the aqueous phase was extracted with DCM, and washed with NaHCO₃ (aq). The combined organic phase was dried over Na₂SO₄ and concentrated, and the residue was purified by flash chromatography using 2% MeOH/CHCl₃ to give compound 64 (0.42 g).
   1H NMR (300 MHz, CDCl₃) 8.4-8.5 (s, 1H), 8.2-8.3 (d, 1H), 7.9-8.0 (s, 1H), 7.6-7.7 (d, 1H), 7.2-7.3 (t, 1H), 6.0-6.2 (bs, 1H), 5.4-5.5 (s, 2H), 5.3-5.4 (s, 2H), 4.4-4.6 (m, 1H), 3.1-3.2 (t, 2H), 2.8-2.9 (t, 2H), 2.5-2.6 (t, 2H), 2.1-2.4 (m, 2H), 1.4-1.5 (s, 9H), 1.2-1.3 (m, 33H), 0.9-1.0 (t, 2H), 0.8-0.9 (m, 3H), 0.7-0.8 (m, 3H).
2. Compound 6 (0.42 g) was dissolved into 20 ml DCM, and TFA (2 ml) were added. The reaction was maintained at 25° C. for 12 h, and TLC indicated reaction was completed. The solvent was removed, and the residue was purified by flash chromatography using 5% MeOH/CHCl₃ to give FL-034 (0.21 g).
   1H NMR (300 MHz, DMSO-d6): 8.2-8.4 (m, 2H), 8.0-8.1 (bs, 1H), 7.6-7.7 (t, 1H), 7.3-7.4 (s, 1H), 6.5-6.6 (bs, 1H), 5.5-5.6 (s, 2H), 5.3-5.4 (s, 2H), 4.2-4.3 (m, 1H), 3.1-3.2 (t, 2H), 2.6-2.8 (m, 2H), 2.4-2.5 (t, 1H), 2.1-2.2 (m, 2H), 1.5-1.7 (m, 2H), 0.8-1.4 (m, 39H).
   LCMS: 774.4 (M+1)⁺

Example 25

Synthesis of FL-036

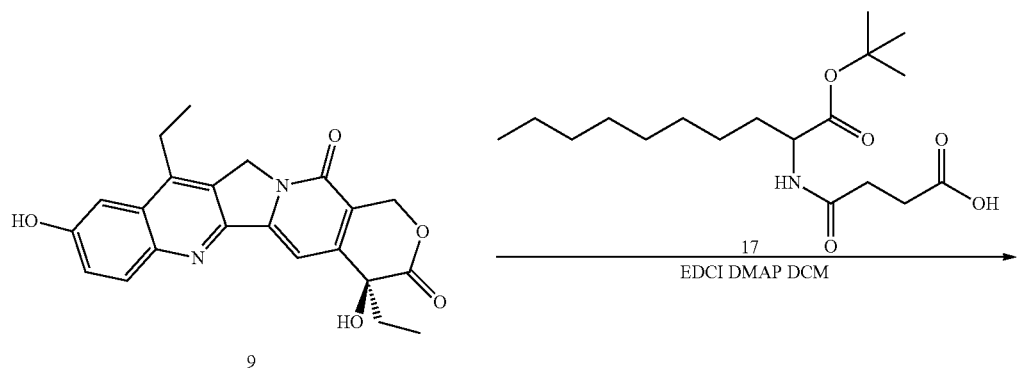

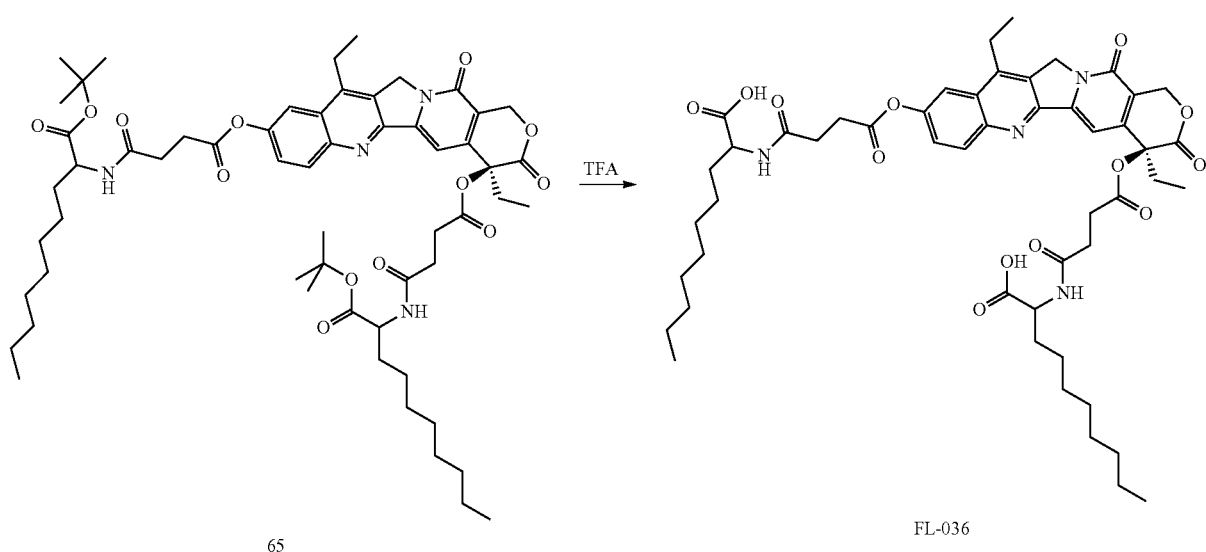

1. Compound 17 (0.7 g) was dissolved into 10 ml DCM, and EDCI (0.488 g), DMAP (63 mg) and compound 9 (0.2 g) were added. The reaction was maintained at 25° C. for 48 h, and TLC indicated reaction was completed. The organic phase was separated and the aqueous phase was extracted with DCM, and washed with NaHCO$_3$ (aq). The combined organic phase was dried over Na$_2$SO$_4$ and concentrated, and the residue was purified by flash chromatography using 2% MeOH/CHCl$_3$ to give compound 65 (150 mg).

1H NMR (300 MHz, CDCl$_3$) 8.3-8.4 (t, 1H), 7.8-7.9 (s, 1H), 7.6-7.7 (d, 1H), 7.3-7.4 (d, 1H), 6.1-6.2 (t, 2H), 6.0-6.2 (bs, 1H), 5.6-5.7 (d, 1H), 5.3-5.5 (d, 1H), 5.2-5.3 (s, 2H), 4.4-4.6 (m, 2H), 3.1-3.2 (t, 2H), 3.0-3.1 (t, 2H), 2.8-2.9 (t, 2H), 2.5-2.6 (t, 2H), 2.1-2.4 (m, 2H), 1.4-1.5 (s, 18H), 0.8-1.5 (m, 38H)

2. Compound 65 (150 mg) was dissolved into 10 ml DCM, and TFA (1.5 ml) were added. The reaction was maintained at 25° C. for 12 h, and TLC indicated reaction was completed. The solvent was removed and the residue was purified by flash chromatography using 5% MeOH/CHCl$_3$ to give FL-036 (120 mg).

1H NMR (300 MHz, DMSO-d6) 8.3-8.4 (t, 1H), 7.8-7.9 (s, 1H), 7.6-7.7 (d, 1H), 7.3-7.4 (d, 1H), 6.1-6.2 (t, 2H), 6.0-6.2 (bs, 1H), 5.3-5.5 (s, 2H), 5.2-5.3 (s, 2H), 4.4-4.6 (m, 2H), 3.1-3.2 (t, 2H), 3.0-3.1 (t, 2H), 2.8-2.9 (t, 2H), 2.5-2.6 (t, 2H), 2.1-2.4 (m, 2H), 0.8-1.5 (m, 38H)

LCMS: 931.7 (M+1)$^+$

Example 26

Synthesis of FL-037

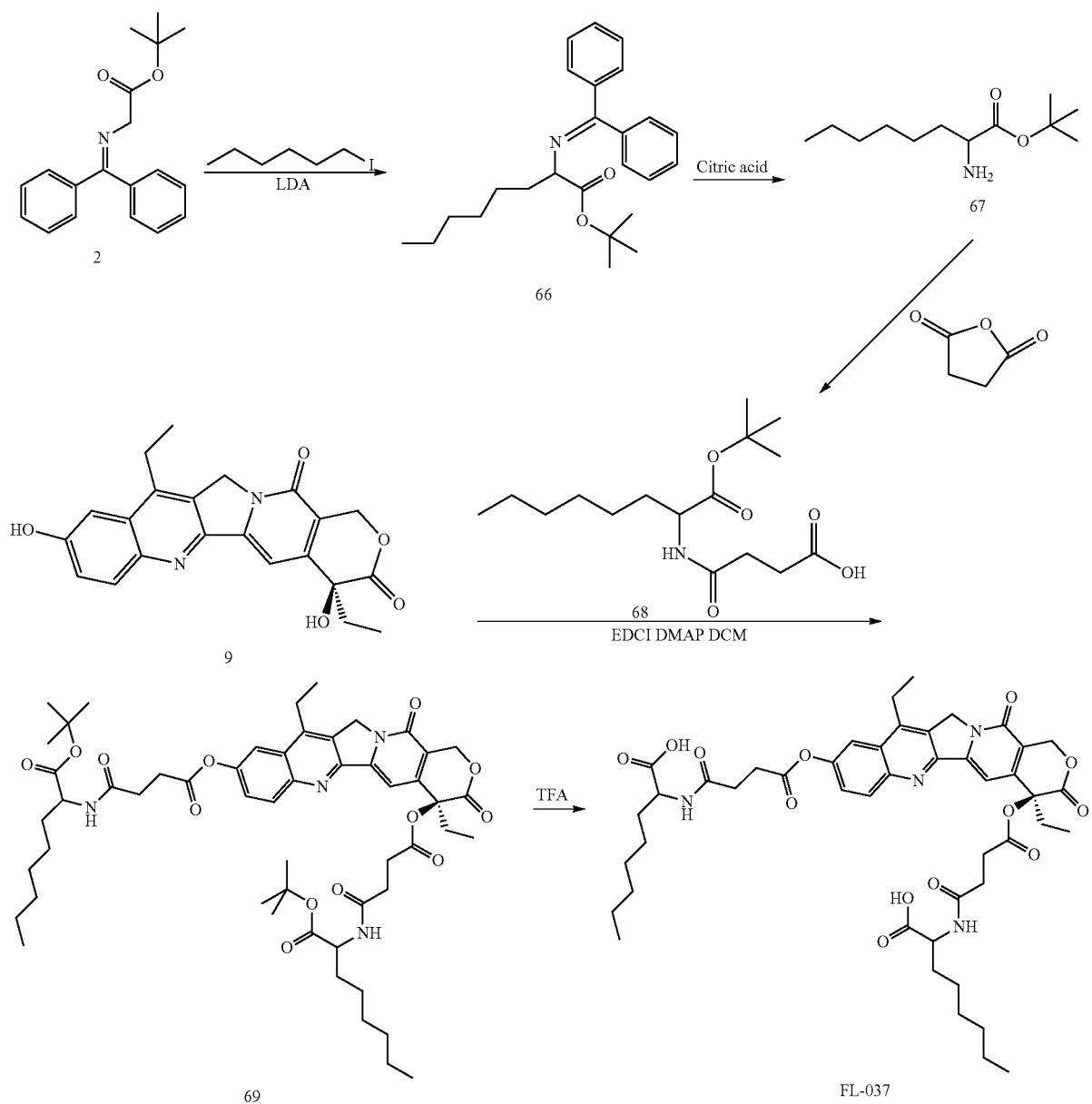

1. Compound 2 (28.5 g) in THF (150 ml) was added to LDA (2.2 eq) and kept at −78° C. in dry THF (150 ml) under nitrogen. After 30 min, 1-iodohexane (14.1 g) was added to the reaction mixture. After 2 h, the mixture was allowed to warm slowly to room temperature and stirred overnight. The reaction was quenched by addition of water (100 ml) to the mixture at 0° C. The mixture was then extracted with $CH_2Cl_2$ (200 ml*3), the product was purified by silica gel column and recrystallized by 5% EA/PE to give compound 66 (16 g) as a white solid.
1H NMR (300 MHz, $CDCl_3$) 7.6-7.7 (m, 2H), 7.4-7.5 (m, 3H), 7.3-7.4 (m, 3H), 7.1-7.2 (m, 2H), 3.8-4.0 (m, 1H), 1.4-1.5 (s, 9H), 1.2-1.4 (m, 10H), 0.8-1.0 (m, 3H).

2. To a solution of compound 66 (16 g) in 100 ml of THF at RT was added 110 ml of 10% aq. Citric acid. The mixture was stirred overnight. The reaction was quenched by addition of water (200 ml) to the mixture at 0° C. The pH value is adjusted to about 7 using $NaHCO_3$. The resulting mixture was extracted with $CH_2Cl_2$ (150 ml*3). The organic phase was washed with saturated solution of sodium chloride and dried over $Na_2SO_4$. The solvent was removed on vacuum to give a crude product, which was purity by the silica gel column and recrystallized by 50% EA/PE to give compound 67 (8.5 g) as a white solid.
1H NMR (300 MHz, $CDCl_3$): 3.3-3.4 (1H), 1.4-1.5 (s, 9H), 1.2-1.4 (m, 6H), 0.8-1.0 (3H).

3. Compound 67 (2.66 g) was dissolved into 15 ml pyridine and cooled down in an ice bath. Dihydrofuran-2,5-dione (1.75 g) was added. The reaction was stirred at RT overnight. Volatiles were removed. The organic phase was separated and the aqueous phase was extracted with DCM, and washed with 2N HCl. The combined the organic phase was dried over Na$_2$SO$_4$ and concentrated to give compound 68 (2.35 g) as a white solid.

1H NMR (300 MHz, CDCl$_3$): 6.2-6.3 (bs, 1H), 4.4-4.5 (m, 1H), 2.7-2.8 (t, 2H), 2.5-2.6 (t, 2H), 1.8-1.9 (m, 1H), 1.4-1.5 (s, 9H), 1.2-1.4 (m, 10H), 0.8-0.9 (t, 3H).

4. Compound 68 (0.641 g) was dissolved into 10 ml DCM, and EDCI (0.5 g), DMAP (60 mg) and compound 9 (0.2 g) were added. The reaction was maintained at 25° C. for 12 h, and TLC indicated reaction was completed. The organic phase was separated and the aqueous phase was extracted with DCM, and washed with NaHCO$_3$ (aq). The combined organic phase was dried over Na$_2$SO$_4$ and concentrated, and the residue was purified by flash chromatography using 2% MeOH/CHCl$_3$ to give compound 69 (210 mg).

1H NMR (300 MHz, CDCl$_3$): 8.3-8.4 (t, 1H), 7.8-7.9 (s, 1H), 7.5-7.6 (d, 1H), 7.2-7.3 (d, 1H), 6.0-6.2 (bs, 2H), 5.6-5.7 (d, 1H), 5.3-5.4 (d, 1H), 5.2-5.3 (s, 2H), 4.4-4.6 (m, 2H), 3.1-3.2 (t, 2H), 2.9-3.0 (t, 2H), 2.7-2.8 (t, 2H), 2.6-2.7 (t, 2H), 2.4-2.5 (m, 2H), 2.0-2.2 (m, 2H), 1.1-1.5 (m, 44H), 0.8-0.9 (t, 3H), 0.7-0.8 (t, 3H), 0.6-0.7 (m, 2H).

5. Compound 69 (210 mg) was dissolved into 10 ml DCM, and TFA (1.9 ml) were added. The reaction was maintained at 25° C. for 12 h, and TLC indicated reaction was completed. The solvent was removed and the residue was purified by flash chromatography using 5% MeOH/CHCl$_3$ to give FL-037 (180 mg).

1H NMR (300 MHz, DMSO-d6): 8.3-8.4 (bs, 2H), 8.2-8.3 (d, 1H), 7.8-7.9 (s, 1H), 7.5-7.6 (d, 1H), 7.2-7.3 (d, 1H), 5.5-5.6 (s, 2H), 5.2-5.3 (s, 2H), 4.2-4.3 (m, 2H), 3.2-3.3 (t, 2H), 2.9-3.0 (t, 2H), 2.7-2.8 (t, 2H), 2.5-2.6 (t, 2H), 2.4-2.5 (m, 2H), 2.0-2.2 (m, 2H), 1.1-1.5 (m, 26H), 0.8-0.9 (t, 3H), 0.7-0.8 (t, 3H), 0.6-0.7 (m, 2H).

LCMS: 876.6 (M+1)$^+$

Example 27

Synthesis of FL-038

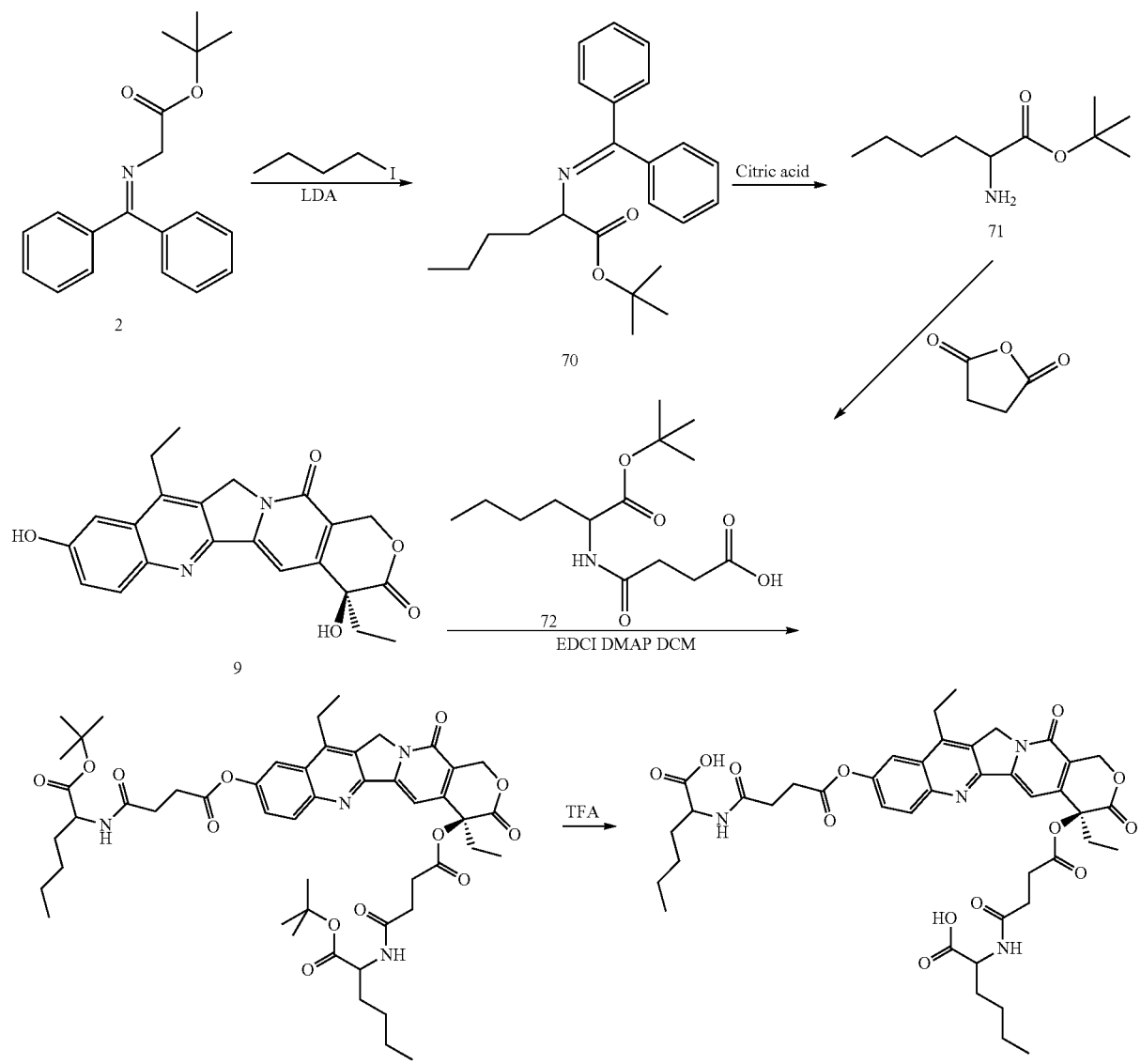

1. Compound 2 (28.5 g) in THF (150 ml) was added to LDA (2.2 eq) and kept at −78° C. in dry THF (150 ml) under nitrogen. After 30 min, 1-iodobutane (13 g) was added to the reaction mixture. After 2 h, the mixture was allowed to warm slowly to room temperature and stirred overnight. The reaction was quenched by addition of water (100 ml) to the mixture at 0° C. The mixture was then extracted with $CH_2Cl_2$ (200 ml*3), the product was purified by silica gel column and recrystallized by 5% EA/PE to give compound 70 (15 g) as a white solid.

1H NMR (300 MHz, $CDCl_3$) 7.6-7.7 (m, 2H), 7.4-7.5 (m, 3H), 7.3-7.4 (m, 3H), 7.1-7.2 (m, 2H), 3.8-4.0 (m, 1H), 1.4-1.5 (s, 9H), 1.2-1.4 (m, 6H), 0.8-1.0 (m, 3H).

2. To a solution of compound 70 (15 g) in 100 ml of THF at RT was added 110 ml of 10% aq. citric acid.

The mixture was stirred overnight. The reaction was quenched by addition of water (200 ml) to the mixture at 0° C. The pH value is adjusted to about 7 using $NaHCO_3$. The resulting mixture was extracted with $CH_2Cl_2$ (150 ml*3). The organic phase was washed with saturated solution of sodium chloride and dried over $Na_2SO_4$. The solvent was removed on vacuum to give a crude product, which was purity by the silica gel column and recrystallized by 50% EA/PE to give compound 71 (8.2 g) as a white solid.

1H NMR (300 MHz, $CDCl_3$) 3.3-3.4 (1H), 1.4-1.5 (s, 9H), 1.2-1.4 (m, 6H), 0.8-1.0 (3H).

3. Compound 71 (2.6 g) was dissolved into 15 ml pyridine and cooled down in an ice bath. Dihydrofuran-2,5-dione (1.8 g) was added. The reaction was stirred at RT overnight. Volatiles were removed. The organic phase was separated and the aqueous phase was extracted with DCM, and washed with 2N HCl. The combined the organic phase was dried over $Na_2SO_4$ and concentrated to give compound 72 (2.3 g) as a white solid.

1H NMR (300 MHz, $CDCl_3$) 6.2-6.3 (bs, 1H), 4.4-4.5 (m, 1H), 2.7-2.8 (t, 2H), 2.5-2.6 (t, 2H), 1.8-1.9 (m, 1H), 1.4-1.5 (s, 9H), 1.2-1.4 (m, 6H), 0.8-0.9 (t, 3H).

4. Compound 72 (0.585 g) was dissolved into 10 ml DCM, and EDCI (0.5 g), DMAP (60 mg) and compound 9 (0.2 g) were added. The reaction was maintained at 25° C. for 12 h, and TLC indicated reaction was completed. The organic phase was separated and the aqueous phase was extracted with DCM, and washed with $NaHCO_3$ (aq). The combined organic phase was dried over $Na_2SO_4$ and concentrated, and the residue was purified by flash chromatography using 2% $MeOH/CHCl_3$ to give compound 73 (200 mg).

1H NMR (300 MHz, $CDCl_3$) 8.3-8.4 (t, 1H), 7.8-7.9 (s, 1H), 7.5-7.6 (d, 1H), 7.2-7.3 (d, 1H), 6.0-6.2 (bs, 2H), 5.6-5.7 (d, 1H), 5.3-5.4 (d, 1H), 5.2-5.3 (s, 2H), 4.4-4.6 (m, 2H), 3.1-3.2 (t, 2H), 2.9-3.0 (t, 2H), 2.7-2.8 (t, 2H), 2.6-2.7 (t, 2H), 2.4-2.5 (m, 2H), 2.0-2.2 (m, 2H), 1.1-1.5 (m, 36H), 0.8-0.9 (t, 3H), 0.7-0.8 (t, 3H), 0.6-0.7 (m, 2H).

5. Compound 73 (200 mg) was dissolved into 10 ml DCM, and TFA (1.8 ml) were added. The reaction was maintained at 25° C. for 12 h, and TLC indicated reaction was completed. The solvent was removed and the residue was purified by flash chromatography using 5% $MeOH/CHCl_3$ to give FL-038 (140 mg).

1H NMR (300 MHz, DMSO-d6): 8.3-8.4 (bs, 1H), 8.2-8.3 (d, 1H), 7.9-8.0 (s, 1H), 7.6-7.7 (d, 1H), 7.2-7.3 (d, 1H), 5.5-5.6 (s, 2H), 5.2-5.43 (s, 2H), 4.4-4.6 (m, 2H), 3.1-3.2 (t, 2H), 2.9-3.0 (t, 2H), 2.7-2.8 (t, 2H), 2.6-2.7 (t, 2H), 2.4-2.5 (m, 2H), 2.0-2.2 (m, 2H), 1.1-1.5 (m, 18H), 0.8-0.9 (t, 3H), 0.7-0.8 (t, 3H), 0.6-0.7 (m, 2H).

LCMS: 819.4 $(M+1)^+$

Example 28

Synthesis of FL-039

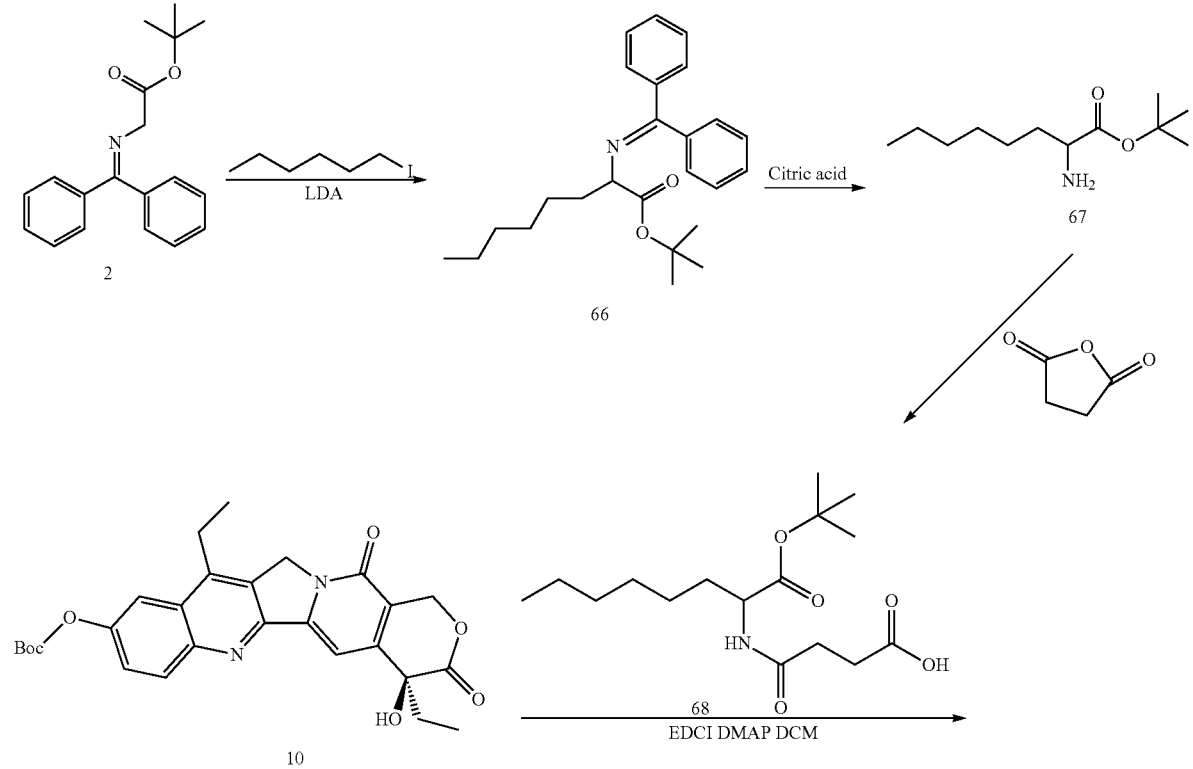

-continued

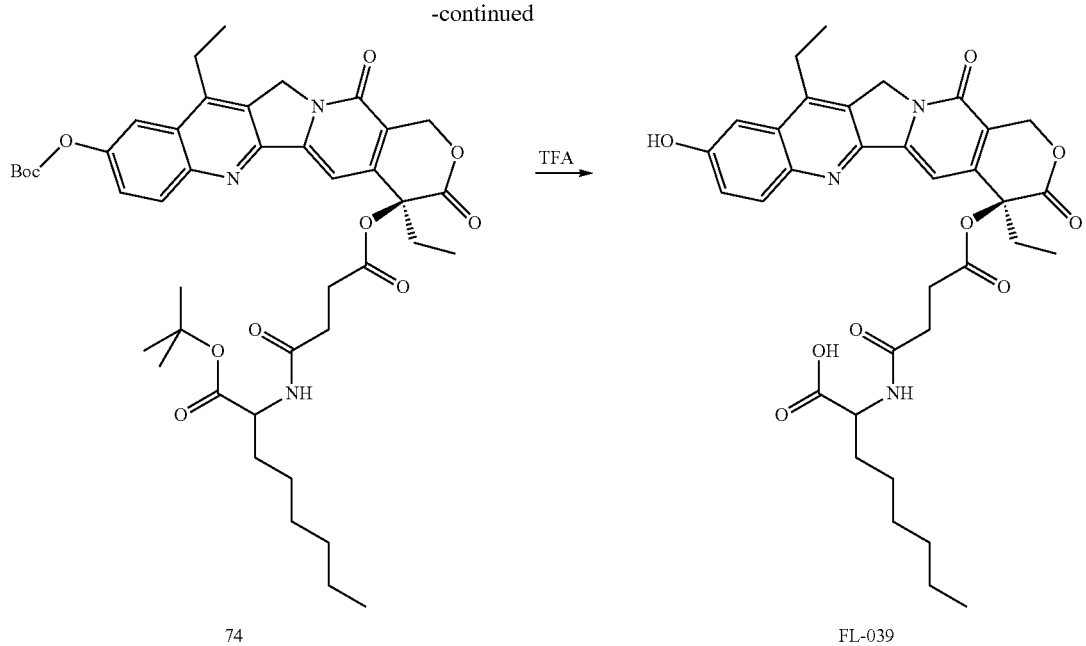

74

FL-039

1. Compound 2 (28.5 g) in THF (150 ml) was added to LDA (2.2 eq) and kept at −78° C. in dry THF (150 ml) under nitrogen. After 30 min, 1-iodohexane (14.1 g) was added to the reaction mixture. After 2 h, the mixture was allowed to warm slowly to room temperature and stirred overnight. The reaction was quenched by addition of water (100 ml) to the mixture at 0° C. The mixture was then extracted with $CH_2Cl_2$ (200 ml*3), the product was purified by silica gel column and recrystallized by 5% EA/PE to give compound 66 (16 g) as a white solid.

1H NMR (300 MHz, $CDCl_3$) 7.6-7.7 (m, 2H), 7.4-7.5 (m, 3H), 7.3-7.4 (m, 3H), 7.1-7.2 (m, 2H), 3.8-4.0 (m, 1H), 1.4-1.5 (s, 9H), 1.2-1.4 (m, 10H), 0.8-1.0 (m, 3H).

2. To a solution of compound 66 (16 g) in 100 ml of THF at RT was added 110 ml of 10% aq. Citric acid. The mixture was stirred overnight. The reaction was quenched by addition of water (200 ml) to the mixture at 0° C. The pH value is adjusted to about 7 using $NaHCO_3$. The resulting mixture was extracted with $CH_2Cl_2$ (150 ml*3). The organic phase was washed with saturated solution of sodium chloride and dried over $Na_2SO_4$. The solvent was removed on vacuum to give a crude product, which was purity by the silica gel column and recrystallized by 50% EA/PE to give compound 67 (8.5 g) as a white solid.

1H NMR (300 MHz, $CDCl_3$): 3.3-3.4 (1H), 1.4-1.5 (s, 9H), 1.2-1.4 (m, 6H), 0.8-1.0 (3H).

3. Compound 67 (2.66 g) was dissolved into 15 ml pyridine and cooled down in an ice bath. Dihydrofuran-2,5-dione (1.75 g) was added. The reaction was stirred at RT overnight. Volatiles were removed. The organic phase was separated and the aqueous phase was extracted with DCM, and washed with 2N HCl. The combined the organic phase was dried over $Na_2SO_4$ and concentrated to give compound 68 (2.35 g) as a white solid.

1H NMR (300 MHz, $CDCl_3$): 6.2-6.3 (bs, 1H), 4.4-4.5 (m, 1H), 2.7-2.8 (t, 2H), 2.5-2.6 (t, 2H), 1.8-1.9 (m, 1H), 1.4-1.5 (s, 9H), 1.2-1.4 (m, 10H), 0.8-0.9 (t, 3H).

4. Compound 69 (0.192 g) was dissolved into 10 ml DCM, and EDCI (0.21 g), DMAP (20 mg) and compound 10 (0.15 g) were added. The reaction was maintained at 25° C. for 12 h, and TLC indicated reaction was completed. The organic phase was separated and the aqueous phase was extracted with DCM, and washed with $NaHCO_3$ (aq). The combined organic phase was dried over $Na_2SO_4$ and concentrated, and the residue was purified by flash chromatography using 2% MeOH/$CHCl_3$ to give compound 74 (65 mg).

1H NMR (300 MHz, $CDCl_3$): 8.2-8.3 (d, 1H), 7.4-7.5 (s, 2H), 7.0-7.1 (d, 1H), 7.2-7.3 (d, 1H), 6.3-6.4 (bs, 1H), 5.5-5.6 (d, 1H), 5.4-5.5 (d, 1H), 5.2-5.3 (s, 2H), 4.2-4.3 (m, 1H), 3.1-3.2 (t, 2H), 2.4-2.5 (m, 2H), 2.0-2.2 (m, 2H), 1.1-1.5 (m, 10H), 0.8-0.9 (t, 3H), 0.7-0.8 (t, 3H), 0.6-0.7 (m, 2H).

5. Compound 74 (65 mg) was dissolved into 10 ml DCM, and TFA (1.1 ml) were added. The reaction was maintained at 25° C. for 12 h, and TLC indicated reaction was completed. The solvent was removed and the residue was purified by flash chromatography using 5% MeOH/$CHCl_3$ to give FL-039 (35 mg).

1H NMR (300 MHz, DMSO-d6): 8.3-8.4 (bs, 1H), 8.2-8.3 (d, 1H), 7.4-7.5 (s, 2H), 7.0-7.1 (d, 1H), 7.2-7.3 (d, 1H), 5.5-5.6 (s, 2H), 5.2-5.4 (s, 2H), 4.2-4.3 (m, 1H), 3.1-3.2 (t, 2H), 2.4-2.5 (m, 2H), 2.0-2.2 (m, 2H), 1.1-1.5 (m, 10H), 0.8-0.9 (t, 3H), 0.7-0.8 (t, 3H), 0.6-0.7 (m, 2H).

LCMS: 634.4 (M+1)$^+$

Example 29

Synthesis of FL-040

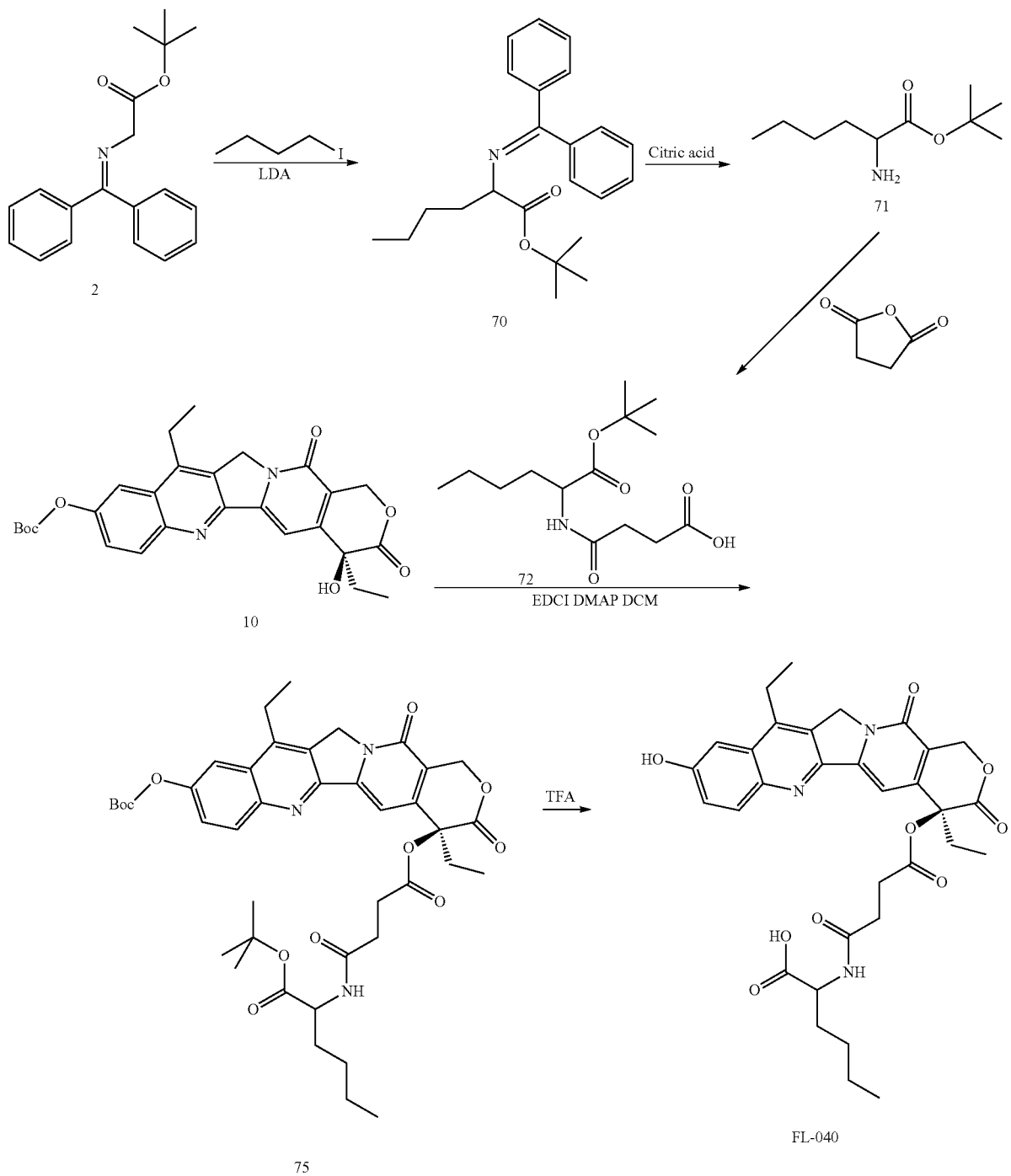

the mixture at 0° C. The mixture was then extracted with CH₂Cl₂ (200 ml*3), the product was purified by silica gel column and recrystallized by 5% EA/PE to give compound 70 (15 g) as a white solid.

1. Compound 2 (28.5 g) in THF (150 ml) was added to LDA (2.2 eq) and kept at −78° C. in dry THF (150 ml) under nitrogen. After 30 min, 1-iodobutane (13 g) was added to the reaction mixture. After 2 h, the mixture was allowed to warm slowly to room temperature and stirred overnight. The reaction was quenched by addition of water (100 ml) to 1H NMR (300 MHz, CDCl₃): 7.6-7.7 (m, 2H), 7.4-7.5 (m, 3H), 7.3-7.4 (m, 3H), 7.1-7.2 (m, 2H), 3.8-4.0 (m, 1H), 1.4-1.5 (s, 9H), 1.2-1.4 (m, 6H), 0.8-1.0 (m, 3H).

2. To a solution of compound 70 (15 g) in 100 ml of THF at RT was added 110 ml of 10% aq. Citric acid. The mixture was stirred overnight. The reaction was quenched by addition of water (200 ml) to the mixture at 0° C. The pH value is adjusted to about 7 using NaHCO$_3$. The resulting mixture was extracted with CH$_2$Cl$_2$ (150 ml*3). The organic phase was washed with saturated solution of sodium chloride and dried over Na$_2$SO$_4$. The solvent was removed on vacuum to give a crude product, which was purity by the silica gel column and recrystallized by 50% EA/PE to give compound 71 (8.2 g) as a white solid.

1H NMR (300 MHz, CDCl$_3$): 3.3-3.4 (1H), 1.4-1.5 (s, 9H), 1.2-1.4 (m, 6H), 0.8-1.0 (3H).

3. Compound 71 (2.6 g) was dissolved into 15 ml pyridine and cooled down in an ice bath. Dihydrofuran-2,5-dione (1.8 g) was added. The reaction was stirred at RT overnight. Volatiles were removed. The organic phase was separated and the aqueous phase was extracted with DCM, and washed with 2N HCl. The combined the organic phase was dried over Na$_2$SO$_4$ and concentrated to give compound 72 (2.3 g) as a white solid.

1H NMR (300 MHz, CDCl$_3$): 6.2-6.3 (bs, 1H), 4.4-4.5 (m, 1H), 2.7-2.8 (t, 2H), 2.5-2.6 (t, 2H), 1.8-1.9 (m, 1H), 1.4-1.5 (s, 9H), 1.2-1.4 (m, 6H), 0.8-0.9 (t, 3H).

4. Compound 72 (0.175 g) was dissolved into 10 ml DCM, and EDCI (0.2 g), DMAP (18 mg) and compound 10 (0.15 g) were added. The reaction was maintained at 25° C. for 12 h, and TLC indicated reaction was completed. The organic phase was separated and the aqueous phase was extracted with DCM, and washed with NaHCO$_3$ (aq). The combined organic phase was dried over Na$_2$SO$_4$ and concentrated, and the residue was purified by flash chromatography using 2% MeOH/CHCl$_3$ to give compound 75 (120 mg).

1H NMR (300 MHz, CDCl$_3$): 8.3-8.4 (t, 1H), 7.8-7.9 (s, 1H), 7.5-7.6 (d, 1H), 7.2-7.3 (d, 1H), 6.0-6.2 (bs, 1H), 5.6-5.7 (d, 1H), 5.3-5.4 (d, 1H), 5.2-5.3 (s, 2H), 4.4-4.6 (m, 1H), 3.1-3.2 (t, 2H), 2.7-2.8 (t, 2H), 2.6-2.7 (t, 2H), 2.0-2.2 (m, 2H), 1.1-1.5 (m, 17H), 0.8-0.9 (t, 3H), 0.7-0.8 (t, 3H), 0.6-0.7 (m, 2H).

5. Compound 75 (120 mg) was dissolved into 10 ml DCM, and TFA (1.8 ml) were added. The reaction was maintained at 25° C. for 12 h, and TLC indicated reaction was completed. The solvent was removed and the residue was purified by flash chromatography using 5% MeOH/CHCl$_3$ to give FL-040 (90 mg).

1H NMR (300 MHz, DMSO-d6): 12.3-12.6 (bs, 1H), 10.3-10.6 (bs, 1H), 8.3-8.4 (bs, 1H), 8.2-8.3 (d, 1H), 7.4-7.5 (d, 2H), 7.0-7.2 (d, 1H), 5.5-5.6 (s, 2H), 5.2-5.43 (s, 2H), 4.2-4.4 (m, 1H), 3.1-3.2 (t, 2H), 2.9-3.0 (t, 2H), 2.0-2.2 (m, 2H), 1.1-1.5 (m, 8H), 0.8-0.9 (t, 3H), 0.7-0.8 (t, 3H), 0.6-0.7 (m, 2H).

LCMS: 606.4 (M+1)$^+$

Example 30

Synthesis of FL-041

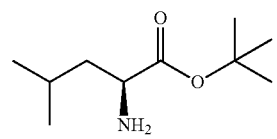

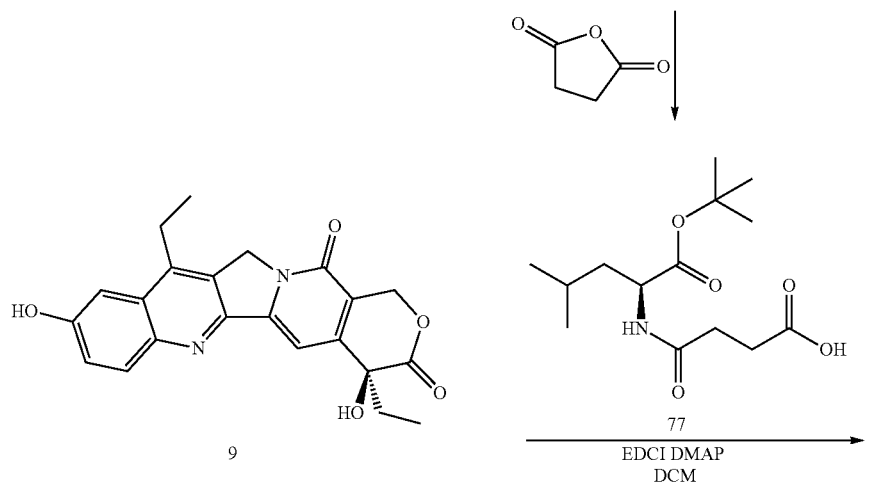

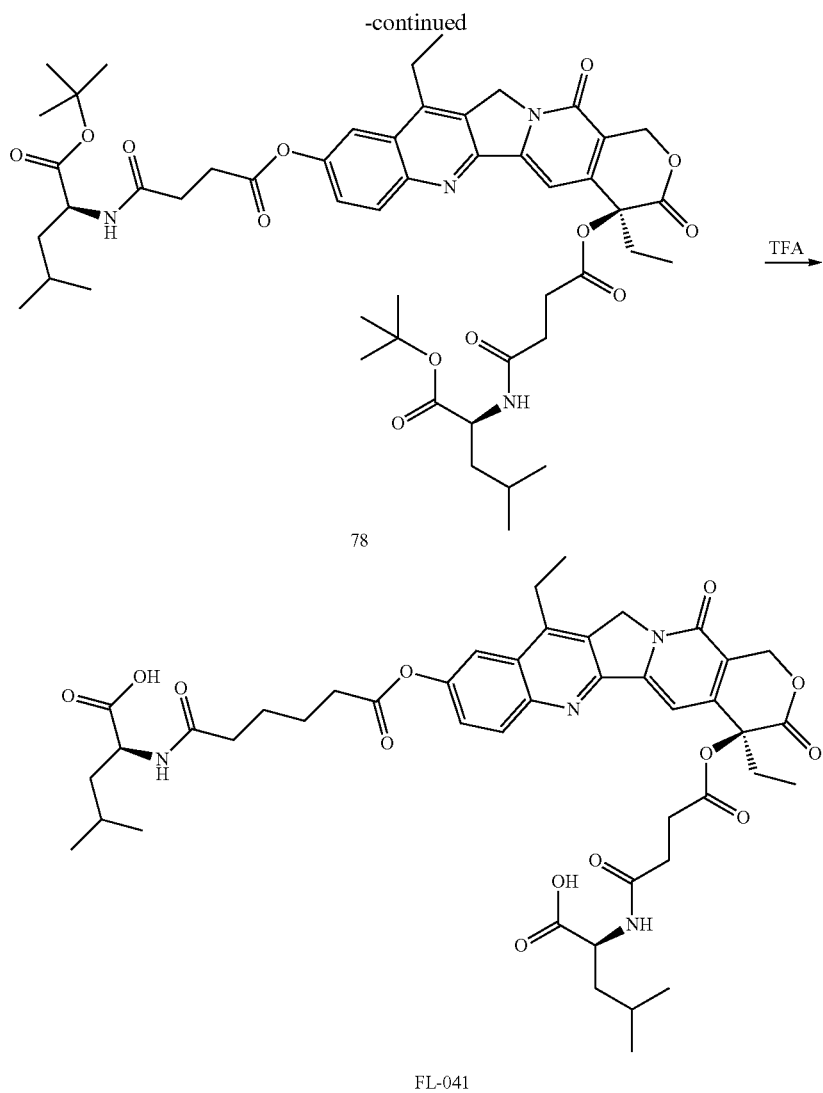

1. Compound 76 (2.23 g) was dissolved into 15 ml pyridine and cooled down in an ice bath. Dihydrofuran-2,5-dione (1.5 g) was added. The reaction was stirred at RT overnight. Volatiles were removed. The organic phase was separated and the aqueous phase was extracted with DCM, and washed with 2N HCl. The combined the organic phase was dried over Na$_2$SO$_4$ and concentrated to give compound 77 (2.5 g) as a white solid.

1H NMR (300 MHz, CDCl$_3$) 6.2-6.3 (bs, 1H), 4.1-4.2 (m, 1H), 2.7-2.8 (t, 2H), 2.5-2.6 (t, 2H), 1.8-1.9 (m, 2H), 1.4-1.5 (s, 9H), 1.0-1.1 (m, 6H).

2. Compound 77 (0.585 g) was dissolved into 10 ml DCM, and EDCI (0.5 g), DMAP (60 mg) and compound 9 (0.2 g) were added. The reaction was maintained at 25° C. for 12 h, and TLC indicated reaction was completed. The organic phase was separated and the aqueous phase was extracted with DCM, and washed with NaHCO$_3$ (aq). The combined organic phase was dried over Na$_2$SO$_4$ and concentrated, and the residue was purified by flash chromatography using 2% MeOH/CHCl$_3$ to give compound 78 (180 mg).

1H NMR (300 MHz, CDCl$_3$): 8.3-8.4 (t, 1H), 7.8-7.9 (s, 1H), 7.5-7.6 (d, 1H), 7.2-7.3 (d, 1H), 6.0-6.2 (bs, 2H), 5.6-5.7 (d, 1H), 5.3-5.4 (d, 1H), 5.2-5.3 (s, 2H), 4.4-4.6 (m, 2H), 3.1-3.2 (t, 2H), 2.9-3.0 (t, 2H), 2.7-2.8 (t, 2H), 2.6-2.7 (t, 2H), 2.4-2.5 (m, 2H), 2.0-2.2 (m, 2H), 1.1-1.5 (m, 36H), 0.8-0.9 (t, 3H), 0.7-0.8 (t, 3H), 0.6-0.7 (m, 2H).

3. Compound 78 (180 mg) was dissolved into 10 ml DCM, and TFA (1.9 ml) were added. The reaction was maintained at 25° C. for 12 h, and TLC indicated reaction was completed. The solvent was removed and the residue was purified by flash chromatography using 5% MeOH/CHCl$_3$ to give FL-041 (125 mg).

1H NMR (300 MHz, DMSO-d6): 12.5-12.7 (bs, 1H), 8.3-8.4 (bs, 2H), 8.2-8.3 (d, 1H), 7.9-8.0 (s, 1H), 7.6-7.7 (d, 1H), 7.2-7.3 (d, 1H), 5.5-5.6 (s, 2H), 5.2-5.43 (s, 2H), 4.4-4.6 (m, 2H), 3.1-3.2 (t, 2H), 2.9-3.0 (t, 2H), 2.7-2.8 (t, 2H), 2.6-2.7 (t, 2H), 2.4-2.5 (m, 2H), 2.0-2.2 (m, 2H), 1.1-1.5 (m, 12H), 0.7-0.9 (t, 15H), 0.6-0.7 (m, 3H).

LCMS: 819.4 (M+1)$^+$

Example 31
Synthesis of FL-042
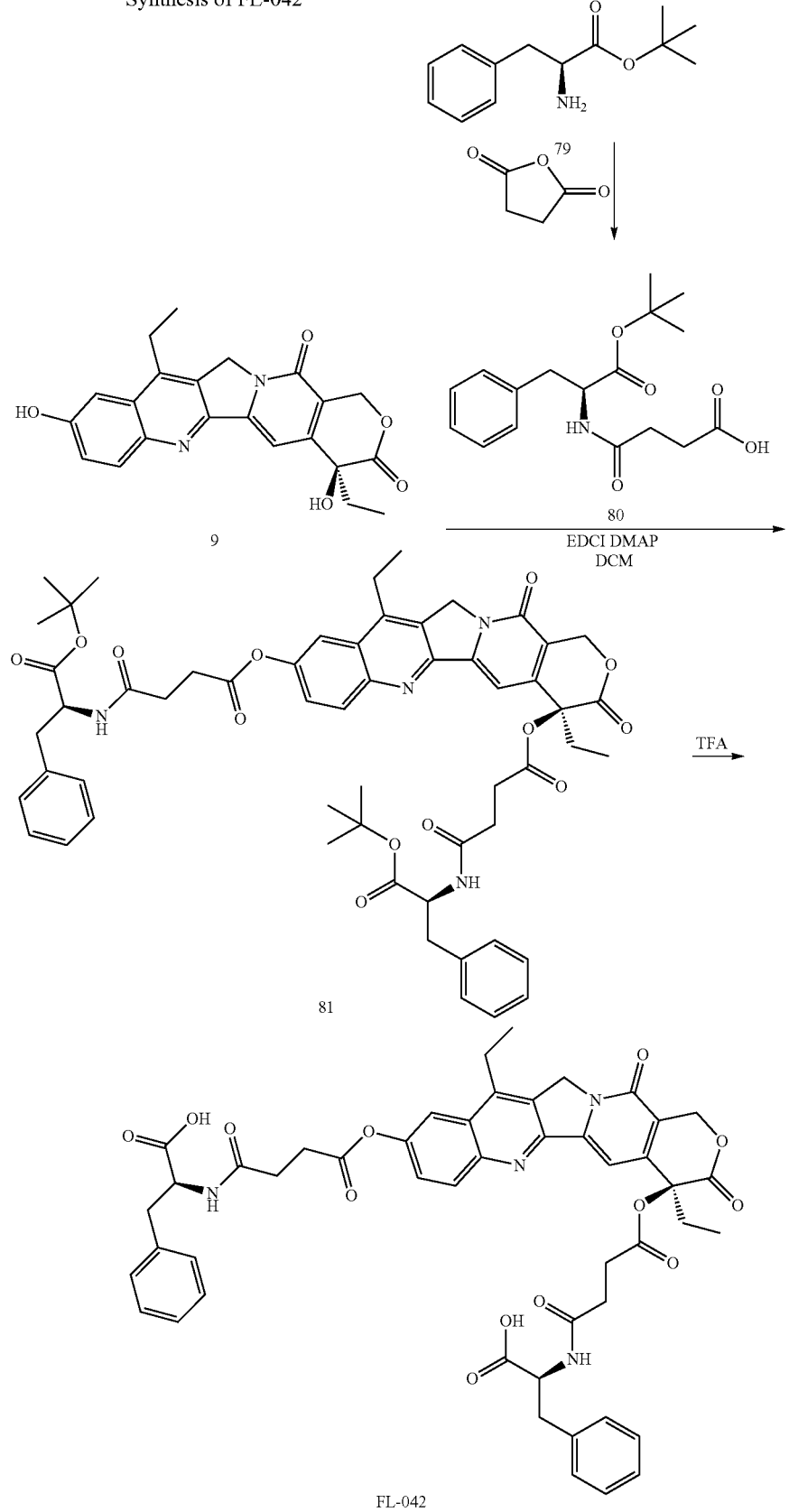

1. Compound 79 (1.3 g) was dissolved into 10 ml pyridine and cooled down in an ice bath. Dihydrofuran-2,5-dione (0.76 g) was added. The reaction was stirred at RT overnight. Volatiles were removed. The organic phase was separated and the aqueous phase was extracted with DCM, and washed with 2N HCl. The combined the organic phase was dried over $Na_2SO_4$ and concentrated to give compound 80 (1.4 g) as a white solid.

1H NMR (300 MHz, $CDCl_3$): 7.2-7.4 (m, 5H), 6.2-6.3 (bs, 1H), 4.4-4.5 (m, 1H), 3.2-3.3 (t, 2H), 2.5-2.6 (t, 2H), 1.8-1.9 (m, 2H), 1.4-1.5 (s, 9H).

2. Compound 80 (0.655 g) was dissolved into 10 ml DCM, and EDCI (0.5 g), DMAP (60 mg) and compound 9 (0.2 g) were added. The reaction was maintained at 25° C. for 12 h, and TLC indicated reaction was completed. The organic phase was separated and the aqueous phase was extracted with DCM, and washed with $NaHCO_3$ (aq). The combined organic phase was dried over $Na_2SO_4$ and concentrated, and the residue was purified by flash chromatography using 2% $MeOH/CHCl_3$ to give compound 81 (186 mg).

1H NMR (300 MHz, $CDCl_3$): 8.3-8.4 (t, 1H), 7.8-7.9 (s, 1H), 7.5-7.6 (d, 1H), 7.2-7.3 (m, 6H), 6.0-6.2 (bs, 2H), 5.6-5.7 (d, 1H), 5.3-5.4 (d, 1H), 5.2-5.3 (s, 2H), 4.4-4.6 (m, 2H), 3.1-3.2 (t, 4H), 2.9-3.0 (t, 2H), 2.7-2.8 (t, 4H), 2.4-2.5 (m, 2H), 2.0-2.2 (m, 2H), 1.4-1.5 (m, 18H), 1.1-1.2 (t, 3H), 0.7-0.8 (t, 3H).

3. Compound 81 (186 mg) was dissolved into 10 ml DCM, and TFA (1.9 ml) were added. The reaction was maintained at 25° C. for 12 h, and TLC indicated reaction was completed. The solvent was removed and the residue was purified by flash chromatography using 5% $MeOH/CHCl_3$ to give FL-043 (125 mg).

1H NMR (300 MHz, DMSO-d6): 12.7-12.9 (bs, 1H), 8.3-8.4 (bs, 2H), 8.2-8.3 (d, 1H), 7.9-8.0 (s, 1H), 7.6-7.7 (d, 1H), 7.2-7.3 (m, 6H), 5.5-5.6 (s, 2H), 5.2-5.43 (s, 2H), 4.4-4.6 (m, 2H), 3.1-3.2 (t, 4H), 2.9-3.0 (t, 4H), 2.7-2.8 (t, 2H), 2.6-2.7 (t, 2H), 2.4-2.5 (m, 2H), 1.1-1.3 (m, 3H), 0.7-0.9 (t, 3H).

LCMS: 887.4 $(M+1)^+$

Example 32

Synthesis of FL-043

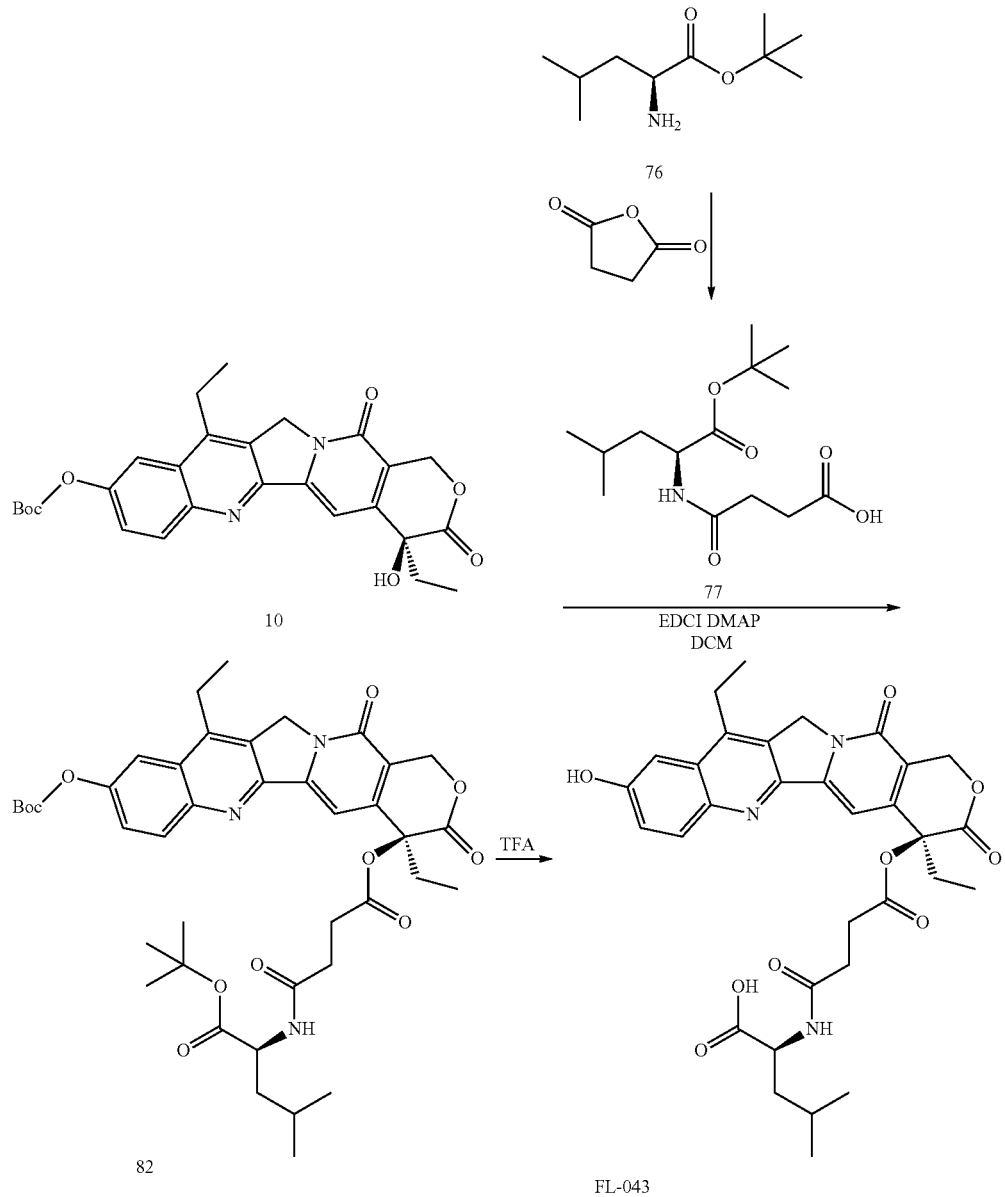

FL-043

1. Compound 76 (2.33 g) was dissolved into 15 ml pyridine and cooled down in an ice bath. Dihydrofuran-2,5-dione (1.5 g) was added. The reaction was stirred at RT overnight. Volatiles were removed. The organic phase was separated and the aqueous phase was extracted with DCM, and washed with 2N HCl. The combined the organic phase was dried over Na$_2$SO$_4$ and concentrated to give compound 77 (2.4 g) as a white solid.

1H NMR (300 MHz, CDCl$_3$): 6.2-6.3 (bs, 1H), 4.1-4.2 (m, 1H), 2.7-2.8 (t, 2H), 2.5-2.6 (t, 2H), 1.8-1.9 (m, 2H), 1.4-1.5 (s, 9H), 1.0-1.1 (m, 6H).

2. Compound 77 (0.28 g) was dissolved into 10 ml DCM, and EDCI (0.337 g), DMAP (30 mg) and compound 10 (0.24 g) were added. The reaction was maintained at 25° C. for 12 h, and TLC indicated reaction was completed. The organic phase was separated and the aqueous phase was extracted with DCM, and washed with NaHCO$_3$ (aq). The combined organic phase was dried over Na$_2$SO$_4$ and concentrated, and the residue was purified by flash chromatography using 2% MeOH/CHCl$_3$ to give compound 82 (205 mg).

1H NMR (300 MHz, CDCl$_3$): 8.3-8.4 (t, 1H), 7.8-7.9 (s, 1H), 7.5-7.6 (d, 1H), 7.2-7.3 (d, 1H), 6.0-6.2 (bs, 1H), 5.6-5.7 (d, 1H), 5.3-5.4 (d, 1H), 5.2-5.3 (s, 2H), 4.4-4.6 (m, 1H), 3.1-3.2 (t, 2H), 2.9-3.0 (t, 2H), 2.4-2.5 (m, 2H), 2.0-2.2 (m, 2H), 1.1-1.5 (m, 21H), 0.8-0.9 (t, 3H), 0.6-0.7 (m, 6H).

3. Compound 82 (205 mg) was dissolved into 10 ml DCM, and TFA (1.8 ml) were added. The reaction was maintained at 25° C. for 12 h, and TLC indicated reaction was completed. The solvent was removed and the residue was purified by flash chromatography using 5% MeOH/CHCl$_3$ to give FL-043 (150 mg).

1H NMR (300 MHz, DMSO-d6): 12.5-12.7 (bs, 1H), 8.3-8.4 (bs, 1H), 8.2-8.3 (d, 1H), 7.3-7.4 (s, 2H), 7.0-7.1 (s, 1H), 5.5-5.6 (s, 2H), 5.2-5.43 (s, 2H), 4.4-4.6 (m, 1H), 3.1-3.2 (t, 2H), 2.7-2.8 (t, 2H), 2.4-2.5 (m, 2H), 2.0-2.2 (m, 2H), 1.1-1.4 (m, 6H), 0.6-0.9 (m, 9H).

LCMS: 606.4 (M+1)$^+$

Example 33

Synthesis of FL-044

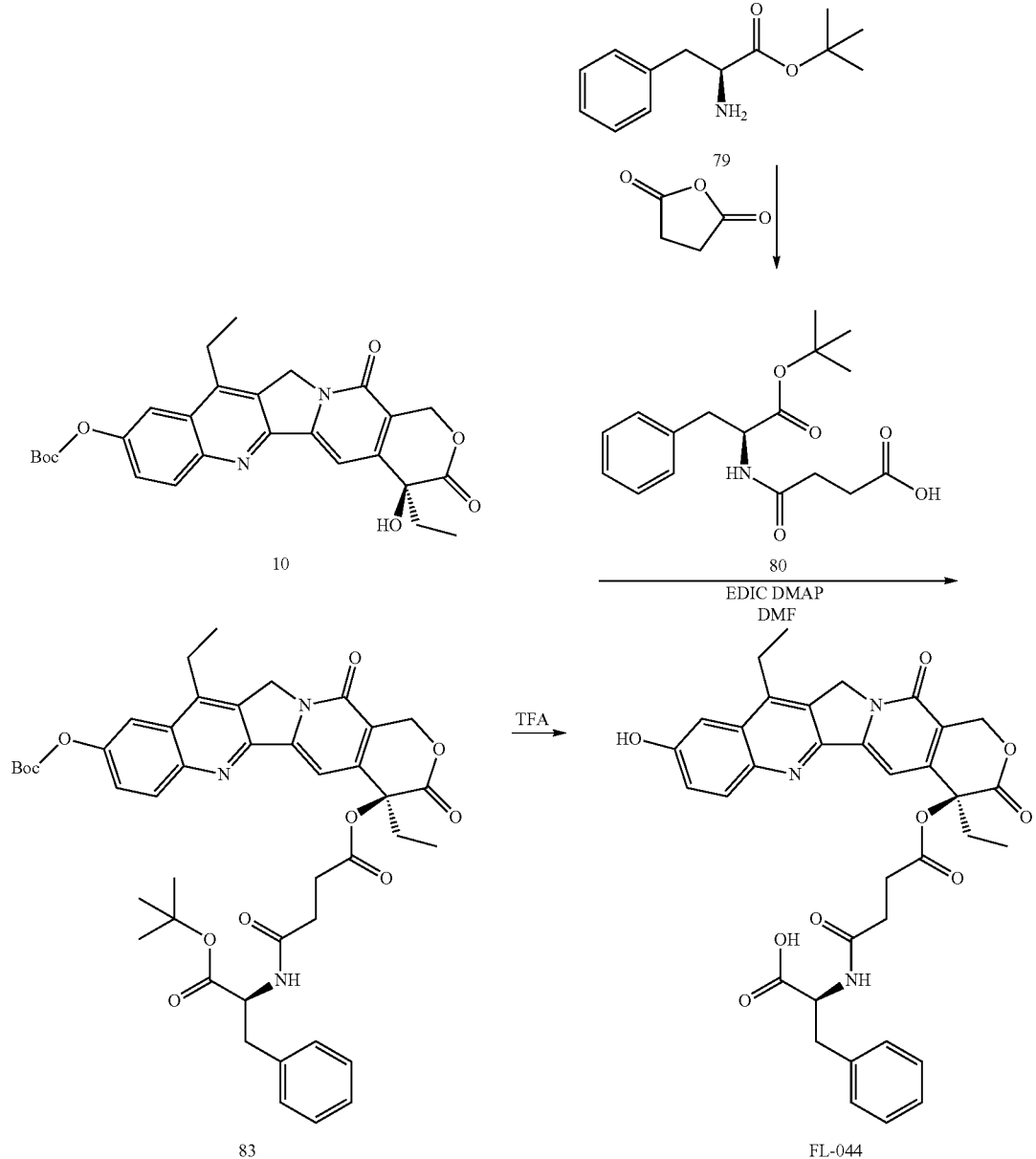

1. Compound 79 (1.3 g) was dissolved into 15 ml pyridine and cooled down in an ice bath. Dihydrofuran-2,5-dione (0.76 g) was added. The reaction was stirred at RT overnight. Volatiles were removed. The organic phase was separated and the aqueous phase was extracted with DCM, and washed with 2N HCl. The combined the organic phase was dried over $Na_2SO_4$ and concentrated to give compound 80 (1.3 g) as a white solid.

1H NMR (300 MHz, $CDCl_3$): 7.2-7.4 (m, 5H), 6.2-6.3 (bs, 1H), 4.4-4.5 (m, 1H), 3.2-3.3 (t, 2H), 2.5-2.6 (t, 2H), 1.8-1.9 (m, 2H), 1.4-1.5 (s, 9H).

2. Compound 80 (0.2 g) was dissolved into 10 ml DCM, and EDCI (0.21 g), DMAP (20 mg) and compound 10 (0.15 g) were added. The reaction was maintained at 25° C. for 12 h, and TLC indicated reaction was completed. The organic phase was separated and the aqueous phase was extracted with DCM, and washed with $NaHCO_3$ (aq). The combined organic phase was dried over $Na_2SO_4$ and concentrated, and the residue was purified by flash chromatography using 2% $MeOH/CHCl_3$ to give compound 83 (120 mg).

1H NMR (300 MHz, $CDCl_3$): 8.3-8.4 (t, 1H), 7.8-7.9 (s, 1H), 7.5-7.6 (d, 1H), 7.2-7.3 (m, 6H), 6.0-6.2 (bs, 1H), 5.6-5.7 (d, 1H), 5.3-5.4 (d, 1H), 5.2-5.3 (s, 2H), 4.4-4.6 (m, 1H), 3.1-3.2 (t, 2H), 2.7-2.8 (t, 2H), 2.4-2.5 (m, 2H), 2.0-2.2 (m, 2H), 1.4-1.5 (m, 18H), 1.1-1.2 (t, 3H), 0.7-0.8 (t, 3H).

3. Compound 83 (120 mg) was dissolved into 10 ml DCM, and TFA (1.8 ml) were added. The reaction was maintained at 25° C. for 12 h, and TLC indicated reaction was completed. The solvent was removed and the residue was purified by flash chromatography using 5% $MeOH/CHCl_3$ to give FL-044 (100 mg).

11H NMR (300 MHz, DMSO-d6): 12.7-12.9 (bs, 1H), 8.3-8.4 (bs, 1H), 8.2-8.3 (d, 1H), 7.9-8.0 (s, 1H), 7.6-7.7 (d, 1H), 7.2-7.3 (m, 6H), 5.5-5.6 (s, 2H), 5.2-5.43 (s, 2H), 4.4-4.6 (m, 1H), 3.1-3.2 (t, 2H), 2.6-2.7 (t, 2H), 2.0-2.1 (m, 2H), 1.1-1.3 (m, 3H), 0.7-0.9 (t, 3H).

LCMS: 640.4 $(M+1)^+$

Persistence in Plasma

Test compounds and control (procaine) were incubated at a concentration of 10 μM with human plasma. The duplicate incubations, conducted in 96-well plates in a shaking water bath maintained at 37° C., were performed for 0 and 60 minutes and quenched by addition of acetonitrile. Ingredients for different incubations were added as shown in Table 2.

TABLE 2

| Components | Add (μL) | |
|---|---|---|
| | 0 min | 60 min |
| Plasma | 300 | 300 |
| 1000 μM Test Compounds or Control in DMSO | 0 | 3 |
| Vortex and Incubated at 37° C. for 60 min. | Yes | Yes |
| ACN (μL) | 750 | 750 |
| IS Soln. (25 μg/mL Propranolol in MeOH:Water 1:1) (μL) | 60 | 60 |
| 1000 μM Test Compounds or Control in DMSO | 3 | 0 |

After quenching by acetonitrile, the plates were capped, vortexed, and centrifuged at 3000 rpm for 10 minutes. The supernatant was injected into LC-MS/MS.

Peak area ratios of procaine and test compounds in incubation samples are listed in Table 3. Percent remaining values are calculated from peak area ratios as shown below and are listed in Table 4.

$$\% \text{ Remaining} = 100 * \frac{PeakArea\ 1hr}{(PeakArea\ 0h - \text{Replicate1} + PeakArea\ 0h - \text{Replicate2})/2}$$

As shown in Table 4, the percent remaining value for procaine, the positive control, is very low. FL-001 and FL-003 are stable in human plasma, with a percent remaining of 127 and 89, respectively. Using the same protocol, the percent remaining of Camptothecin after 1-hr incubation in human plasma is 11%.

TABLE 3

Procaine and Test Compound Peak Area Ratio in Incubation Samples

| | Peak Area Ratio (Analyte/IS) Human Plasma | | | |
|---|---|---|---|---|
| | 0 min | | 60 min | |
| Compound | Replicate 1 | Replicate 2 | Replicate 1 | Replicate 2 |
| Procaine | 0.60 | 1.21 | 0.00 | 0.11 |
| FL-001 | 1.47 | 1.75 | 1.96 | 2.13 |
| FL-003 | 3.91 | 4.03 | 3.37 | 3.73 |

TABLE 4

Percent Remaining of Procaine and Test Compounds after 1-hr Incubation

| | % Remaining after 1-hr Incubation at 37° C. in Human Plasma | | |
|---|---|---|---|
| Compound | Replicate 1 | Replicate 2 | Average |
| Procaine | 0 | 12 | 6 |
| FL-001 | 122 | 132 | 127 |
| FL-003 | 85 | 94 | 89 |

HSA-binding Assay

Equilibrium dialysis was performed in a 24-well BD Gentest Serum Binding System (BD Biosciences, Woburn, Mass.). Human serum albumin (HSA) at 0.6 mM was prepared by dissolving in phosphate buffered saline (PBS: 4.01 mL 1 M $K_2HPO_4$+0.99 mL 1 M $KH_2PO_4$+1.37 mL 5 M NaCl+43.63 mL water). After washing and soaking the 24-well BD Gentest Serum Binding System with water, 30% ethanol, and PBS, 750 μL of HSA and 250 μL of PBS were dispensed into each donor and receiver well, respectively. 3.75 μL of 1 mM test compound or wafarin (as control) was spiked into HSA in each donor well. The duplicate incubations were performed at 37° C. for 20 hrs.

After incubation, HSA and buffer samples collected from donor and receiver wells, together with calibration standard samples, were prepared in 96-well plates as shown in Table 5.

TABLE 5

| | Cal. Std. | HSA Sample | Buffer Sample |
|---|---|---|---|
| Blank HSA (μL) | 50 | 0 | 50 |
| Blank Buffer (μL) | 100 | 100 | 0 |
| MeOH (μL) | 0 | 50 | 50 |
| HSA Sample (μL) | 0 | 50 | 50 |
| Buffer Sample (μL) | 0 | 0 | 100 |
| IS Soln. (μL) | 20 | 20 | 20 |
| Working Std. Soln. (μL) | 50 | 0 | 0 |
| Chilled ACN (μL) | 250 | 250 | 250 |
| Total Volume (μL) | 470 | 470 | 470 |

IS Soln.: 20 μM tolbutamide in M:W 1:1 for warfarin; 25 μg/mL propranolol in M:W 1:1 for test compounds
Working Std. Soln.: 10, 20, 100, 200, 1000, 2000, and 10000 μM in methanol The plates were then capped, vortexed, and centrifuged at 3500 rpm for 10 minutes. The supernatant was injected into LC-MS/MS. Sample analysis was performed on an LC/MS/MS system composed of Shimadzu Prominence pumps, SIL-20ACHT autosampler, and Applied Biosystems/MDS Sciex API 3200.

Percent protein binding values were calculated from the concentration data and are listed in Table 6. The protein binding for warfarin in HSA, 99.5%, is consistent with literature values of protein binding of warfarin in human plasma in the range of 98-100%. The % protein binding values for all the test compounds in HSA, are higher than 97%.

TABLE 6

% Protein Binding of Warfarin, as Control, and Test Compounds in HSA

| Compound | Incubation Conc. (μM) | % Protein Binding in Human Serum Albumin |
|---|---|---|
| Warfarin | 5 | 99.5 |
| FL-001 | 5 | >99.9 |
| FL-003 | 5 | >99.9 |
| FL-004 | 5 | >99.8 |
| FL-006 | 5 | 98.5 |
| FL-008 | 5 | >99.8 |
| FL-010 | 5 | >99.8 |
| FL-012 | 5 | >97.9 |
| FL-013 | 5 | >99.9 |
| FL-014 | 5 | >99.9 |
| FL-015 | 5 | >99.9 |
| FL-033 | 5 | >99.9 |

The invention claimed is:

1. A compound of the following formula or a pharmaceutically acceptable salt thereof:

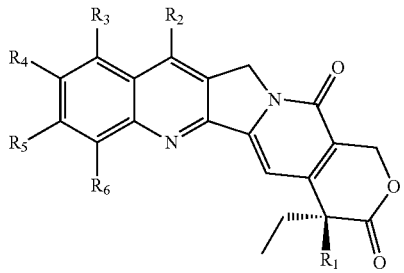

wherein
$R_1$ is OH or linker-HSA binding moiety;
$R_{2-6}$ are each, independently, H, halo, OH, $NO_2$, $NH_2$, lower alkyl, O-lower alkyl, NH-lower alkyl, N(lower alkyl)$_2$, lower alkyl-N(lower alkyl)$_2$, lower alkyl-Si(lower alkyl)$_3$,

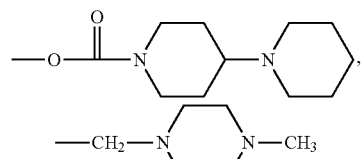

or linker-HSA binding moiety;
wherein
$R_4$ and $R_5$ optionally, together form $-OCH_2CH_2O-$,
$R_2$ and $R_3$ optionally, together form

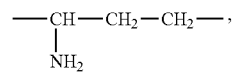

and
if $R_1$ is OH, then at least one of $R_{2-6}$ must be linker-HSA binding moiety;
linker-HSA binding moiety is:

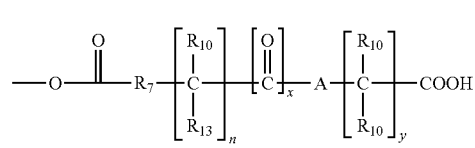

wherein
A is

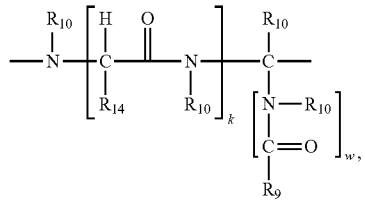

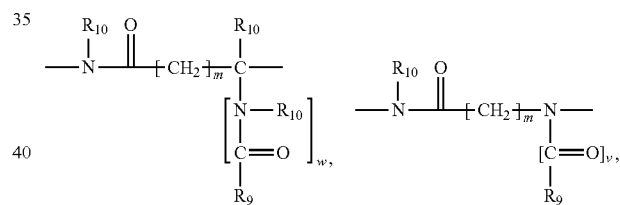

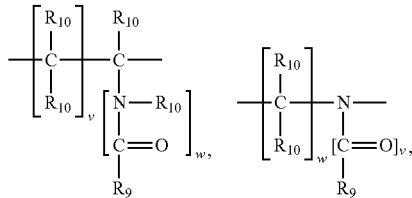

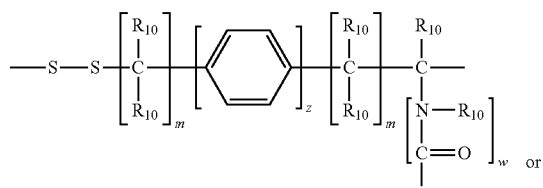

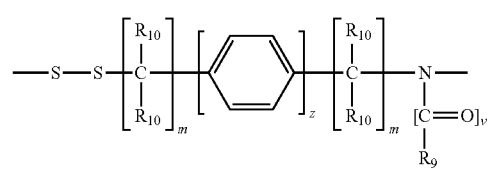

$R_7$ is O, NH or a covalent bond;

$R_9$ is an unbranched or branched alkyl, alkylene or alkyne of 2 to 30 carbon atoms optionally including one or more ring structures of 3 to 6 atoms when $R_9$ has at least 7 carbon atoms, and including heteroatoms of oxygen in an integer number from 0 to one fifth the total number of carbon atoms in $R_9$, with the proviso that there be no covalent bonds between oxygen atoms in $R_9$;

$R_{10}$ is, independently in each instance, H or lower alkyl;

$R_{13}$ is, independently in each instance, H, OH, $NO_2$, $NH_2$, $NH_3^+$, SH or a branched or unbranched alkyl, alkylene or alkyne of 1 to 8 carbon atoms, wherein the alkyl, alkylene or alkyne is optionally substituted with one or two substituents selected from the group consisting of halo, OH, $NO_2$, $NH_2$, $NH_3^+$, SH and =O, and optionally includes up to two heteroatoms independently selected from O, S and N, with the proviso that no O, S or N atom in the alkyl, alkylene or alkyne is covalently bonded to any other O, S or N atom;

$R_{14}$ is, independently in each instance, H, OH, $NO_2$, $NH_2$, $NH_3^+$, SH or a branched or unbranched alkyl, alkylene or alkyne of 1 to 10 carbon atoms, wherein the alkyl, alkylene or alkyne optionally includes one or more ring structures of 3 to 9 atoms, is optionally substituted with one or two substituents selected from the group consisting of halo, OH, $NO_2$, $NH_2$, $NH_3^+$, SH and =O, and optionally includes up to two heteroatoms independently selected from O, S and N, with the proviso that no O, S or N atom in the alkyl, alkylene or alkyne is covalently bonded to any other O, S or N atom;

k is 0, 1 or 2;

m, independently in each instance, is 0, 1, 2 or 3;

n is 1, 2 or 3;

v is 0 or 1;

w is 0 or 1;

x is 0 or 1, with the proviso that x is 0 when a di-sulfide bond is present in A;

y is 0, 1, 2 or 3; and z is 0 or 1 wherein the compound comprises no more than two linker-HSA binding moieties.

2. The compound of claim 1, comprising one linker-HSA binding moiety.

3. The compound of claim 1, comprising two linker-HSA binding moiety.

4. The compound of claim 1, wherein linker-HSA binding moiety is:

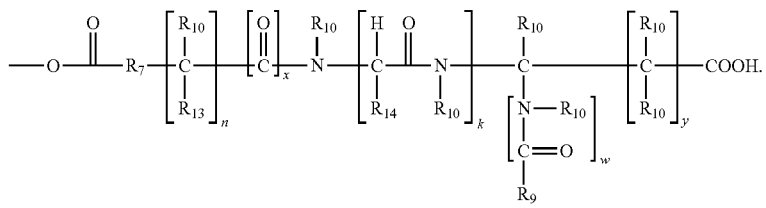

5. The compound of claim 1, wherein linker-HSA binding moiety is:

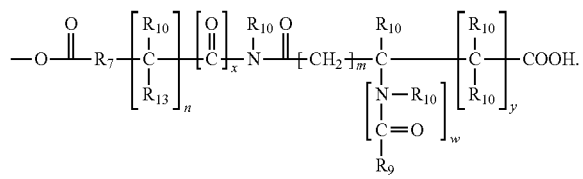

6. The compound of claim 1, wherein linker-HSA binding moiety is:

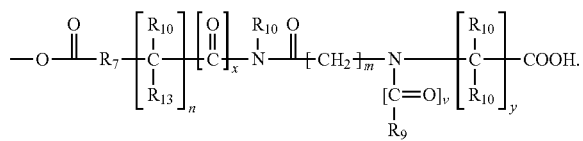

7. The compound of claim 1, wherein linker-HSA binding moiety is:

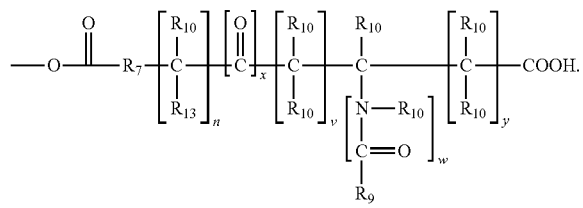

8. The compound of claim 1, wherein linker-HSA binding moiety is:

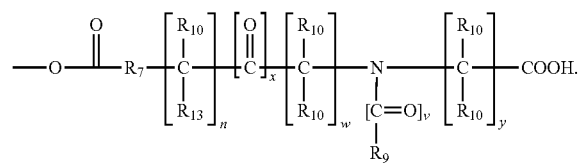

9. The compound of claim 1, wherein linker-HSA binding moiety is:

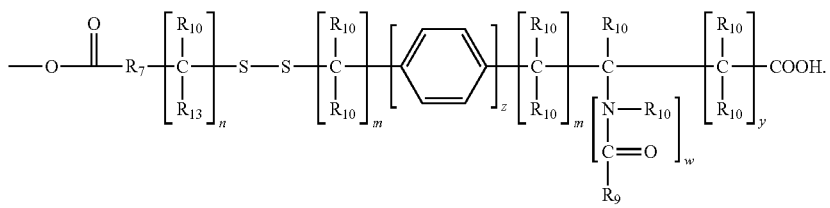

10. The compound of claim 1, wherein linker-HSA binding moiety is:

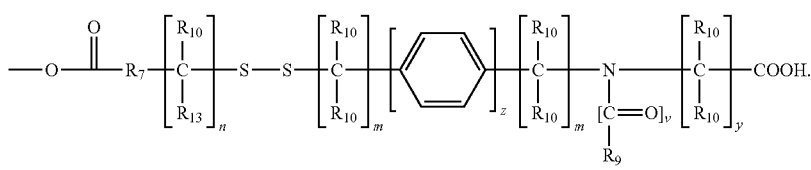

11. The compound of claim 1, wherein $R_7$ is a covalent bond.
12. The compound of claim 1, wherein $R_7$ is O.
13. The compound of claim 1, wherein $R_7$ is NH.
14. The compound of claim 1, wherein $R_2$ is —CH$_2$CH$_3$; $R_3$ is —H, $R_4$ is

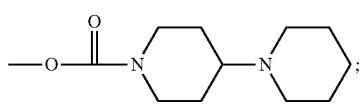

$R_5$ is H; $R_6$ is H and $R_1$ is linker-HSA binding moiety.
15. The compound of claim 1, wherein $R_2$ is H; $R_3$ is H; $R_4$ is H; $R_5$ is H; $R_6$ is H and $R_1$ is linker-HSA binding moiety.
16. The compound of claim 1, wherein $R_2$ is H; $R_3$ is

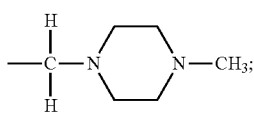

$R_4$ is —OH or linker-HSA binding moiety; $R_5$ is H; $R_6$ is H; $R_1$ is —OH or linker-HSA binding moiety; at least one of $R_1$ and $R_4$ must be linker-HSA binding moiety.
17. The compound of claim 1, wherein $R_2$ is —CH$_2$CH$_3$; $R_3$ is H; $R_4$ is —OH or linker-HSA binding moiety; $R_5$ is H; $R_6$ is H; $R_1$ is —OH or linker-HSA binding moiety; at least one of $R_1$ and $R_4$ must be linker-HSA binding moiety.
18. The compound of claim 4, wherein linker-HSA binding moiety is:

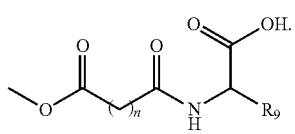

19. The compound of claim 8, wherein linker-HSA binding moiety is:

![structure]

20. The compound of claim 5, wherein linker-HSA binding moiety is:

![structure]

21. The compound of claim 14, wherein linker-HSA binding moiety is:

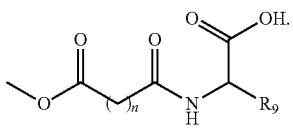

22. The compound of claim 16, wherein linker-HSA binding moiety is:

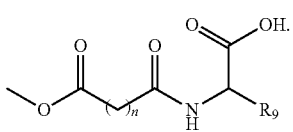

23. The compound of claim 17, wherein linker-HSA binding moiety is:

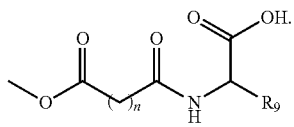

24. A method to inhibit the enzyme topoisomerase I in an animal in need thereof, comprising administering to the animal an effective amount of a composition comprising a compound of claim 1.

25. A method to treat cancer in a patient comprising administering a composition comprising a compound of claim 1 to said patient in an effective amount to treat said cancer.

26. The method of claim 25, wherein said cancer is lung, breast, colon, prostate, melanoma, pancreas, stomach, liver, brain, kidney, uterus, cervix, ovaries, urinary tract, gastrointestinal or leukemia.

27. The method of claim 25, wherein said cancer is solid tumor or blood borne tumor.

28. The method of claim 25, wherein said composition is administered orally, parenterally, intramuscularly, transdermally, intravenously or by an airborne delivery system.

* * * * *